US006841362B1

(12) United States Patent
Fisher et al.

(10) Patent No.: US 6,841,362 B1
(45) Date of Patent: Jan. 11, 2005

(54) MELANOMA DIFFERENTIATION ASSOCIATED GENE-7 PROMOTER AND USES THEREOF

(75) Inventors: Paul B. Fisher, Scardale, NY (US); Malavi T. Madireddi, Lawrenceville, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/515,369

(22) Filed: Feb. 29, 2000

(51) Int. Cl.⁷ .......................... C12P 21/00; C12N 5/10; C12N 15/85; A61K 48/00
(52) U.S. Cl. .................. 435/70.1; 435/320.1; 435/325; 514/44; 536/24.1
(58) Field of Search ............................ 435/70.1, 320.1, 435/325; 514/44; 536/24.1

(56) References Cited

U.S. PATENT DOCUMENTS

| | | | |
|---|---|---|---|
| 5,399,346 A | 3/1995 | Anderson et al. | |
| 5,643,761 A | 7/1997 | Fisher | |
| 5,710,137 A | 1/1998 | Fisher | |
| 5,912,236 A | 6/1999 | Xu et al. | |
| 6,025,127 A | 2/2000 | Sidransky | |
| 6,051,376 A | 4/2000 | Fisher et al. | |
| 6,355,622 B1 | 3/2002 | Fisher | |

FOREIGN PATENT DOCUMENTS

| | | |
|---|---|---|
| WO | WO 90/11092 | 10/1990 |
| WO | WO 93/23034 | 11/1993 |
| WO | WO 65/11986 | 5/1995 |
| WO | WO 98/06441 | 2/1998 |

OTHER PUBLICATIONS

Jiang et al., The melanoma differentiation–associated gene mda–6, which encodes the cyclin–dependent kinase inhibitor p21, is differentially expressed during growth, differentiation and progression in human melanoma cells; Oncogene (1995) 10, 1855, 1864.*
El–Deiry et al., WAF1, a Potential Mediator of p53 Tumor Suppression; Cell, vol. 75, 817–825, Nov. 19, 1993.*
Madireddi MT, Dent P, Fisher PB (2000a). Regulation of mda–7 gene expression during human melanoma differentiation. Oncogene 19:1362–1368.
Madireddi MT, Su ZZ, Young CSH, Goldstein NI, Fisher PB (2000b). Mda–7, a novel melanoma differentiation associated gene with promise for cancer gene therapy: In: Cancer Gene Therapy: Past Achievements and Future Challenges. Publishing Company, New York, NY, vol. 465, Ch. 22, pp. 239–261.
Fontes AM, Ito J, Jacobs–Lorena M (1999). Control of messenger RNA stability during development. Curr. Top. Dev. Biol. 44:171–202.

Patterson A, Harris AL (1999). Molecular chemotherapy for breast cancer. Drugs Aging 14:75–90.

Tamayo P, Slonim D, Mesirov J, Zhu Q, Kitareewan S, Dimitrovsky E, Lander ES, Golub TR (1999). Interpreting patterns of gene expression with self–organizing maps: methods and application to hematopoietic differentiation. Proc. Natl. Acad. Sci. USA 96:907–2912.

Welm AL, Timchenko NA, Darlington GJ (1999). C/EBPalpha regulates generation of C/EBPbeta isoforms through activation of specific proteolytic cleavage. Mol. Cell Biol. 19:1695–704.

Auer KL, Contessa J, Brenz–Verca S, Pirola L, Rusconi S, Cooper G, Abo A, Wymann MP, Davis RJ, Birrer M, Dent P (1998). The Ras/Ras1/Cdc42/SEK/JNK/c–Jun cascade is a key pathway by which agonists stimulate DNA synthesis in primary cultures of rat hepatocytes. Mol. Biol. Cell 9:561–73.

Kang DC, La France R, Su ZZ, Fisher PB (1998a), Reciprocal subtraction differential RNA display (RSDD): an efficient and rapid procedure for isolating differentially expressed gene sequences. Proc. Natl. Acad. Sci. USA 95:13788–13793.

Kang DC, Motwani M, Fisher PB. (1998b). Role of the transcription factor AP–1 in melanoma differentiation (review) Int. J. Oncol. 13:1117–26.

Meier F, Satyamoorthy K, Nesbit M, Hsu MY, Schittek B, Garbe C, Herlyn M (1998). Molecular events in melanoma development and progression. Front. Bioscience 3:D1005–1010.

(List continued on next page.)

Primary Examiner—David Guzo
Assistant Examiner—Daniel M. Sullivan
(74) Attorney, Agent, or Firm—Baker Botts L.L.P.

(57) ABSTRACT

The present invention provides for an isolated Mda-7 promoter capable of directing transcription of a heterologous coding sequence positioned downstream therefrom, wherein the promoter is selected from the group consisting of: (a) a promoter comprising the nucleotide sequence shown in SEQ ID NO:1; (b) a promoter comprising a nucleotide sequence functionally equivalent to the nucleotide sequence shown in SEQ ID NO: 1; and (c) a promoter comprising a nucleotide sequence that hybridizes to a sequence complementary to the promoter of (a) or (b) in a Southern hybridization reaction performed under stringent conditions. The invention provides for a host cell comprising the recombinant expression construct as described herein. The invention provides for a method for expressing foreign DNA in a host cell comprising: introducing into the host cell a gene transfer vector comprising an Mda-7 promoter nucleotide sequence operably linked to a foreign DNA encoding a desired polypeptide or RNA, wherein said foreign DNA is expressed.

15 Claims, 17 Drawing Sheets

OTHER PUBLICATIONS

Spicher A, Guicherit OM, Duret L, Aslanian A, Sanjines EM, Denko NC, Giaccia AJ, Blau HM (1998). Highly conserved RNA sequences that are sensors of environmental stress. Mol. Cell. Biol. 18:7371–7382.

Su ZZ, Madireddi MT, Lin JJ, Young CSH, Kitada S, Reed JC, Goldstein NI, Fisher PB (1998). The cancer growth suppressor gene mda–7 selectively induces apoptosis in human breast cancer cells and inhibits tumor growth in nude mice. Proc. Natl. Acad. Sci. USA 95:14400–14405.

Gant TM, Wilson KL (1997). Nuclear assembly. Annu. Rev. Cell Dev. Biol. 13:669–695.

Myer VE, Fan XC, Steitz JA (1997). Identification of HuR as a protein implicated in AUUUA–mediated mRNA decay. EMBO J. 16:2130–2139.

Rajagopalan LE, Malter JS (1997). Regulation of eukaryotic messenger RNA turnover. Prog. Nucleic Acid Res. Mol. Biol. 56:257–286.

Scott RE (1997). Differentiation, differentiation/gene therapy and cancer. Pharmacol. Ther. 73:51–65.

Su ZZ, Shi Y, Fisher PB (1997). Subtraction hybridization identifies a progression elevated gene PEG–3 with sequence homology to a growth arrest and DNA damage inducible gene. Proc. Natl. Acad. Sci. USA 94:9125–9130.

Wada RK, Pai DS, Huang J, Yamashiro JM, Sidell N (1997). Interferon–gamma and retinoic acid down–regulate N–myc in neuroblastoma through complementary mechanisms of action. Cancer Lett. 121:181–188.

Welch DR, Goldberg SF (1997). Molecular mechanisms controlling human melanoma progression and metastasis. Pathobiology 65:311–330.

Dong Z, Xu RH, Kim J, Zhan SN, Ma WY, Colburn NH, Kung H (1996). AP–1/jun is required for early Xenopus development and mediates mesoderm induction by fibroblast growth factor but not by activin. J. Biol. Chem. 271:9942–9946.

Ross J (1996). Control of messenger RNA stability in higher eukaryotes. Trends Genet. 12:171–175.

Jiang H, Lin J, Young SM, Goldstein NI, Waxman S, Davila V, Chellappan SP, Fisher PB (1995c). Cell cycle gene expression and E2F transcription factor complexes in human melanoma cells induced to terminally differentiate. Oncogene 11:1179–1189.

Kerr LD (1995). Electrophoretic mobility shift assay. Methods Enzymol. 254:619–632.

MacDougald OA, Lane MD (1995). Transcriptional regulation of gene expression during adipocyte differentiation. Annu. Rev. Biochem. 64:345–373.

Su ZZ, Yemul A, Estabrook A, Zimmer SG, Friedman RM, Fisher PB (1995). Transcriptional switching model for the regulation of tumorigenesis and metastasis by the Ha–ras oncogene: transcriptional changes in the Ha–ras tumor suppressor gene lysyl oxidase. Intl. J. Oncology 7:1279–1284.

Algate PA, Steelman LS, Mayo MW, Miyamjima A, McCubrey JA (1994). Regulation of the interleukin–3 (IL–3) receptor by IL–3 in the fetal liver–derived FL5.12 cell line. Blood 83:2459–2468.

Armstrong BK, Kricker A (1994). Cutaneous melanoma. Cancer Surv. 19/20:219–240.

Cluitmans FH, Esendam BH, Landegent JE, Willemze R, Falkenburg JH (1994). IL–4 down–regulates IL–2, IL–3–, and GM–CSF–induced cytokine gene expression in peripheral blood monocytes. Ann Hematol. 68:293–298.

de Wit H, Esselink MT, Halie MR, Vellenga E (1994). Differential regulation of M–CSF and IL–6 gene expression in monocytic cells. Br. J. Hematol. 86:259–264.

Jiang H, Lin J, Fisher PB (1994a). A molecular definition of terminal differentiation in human melanoma cells. Mol. Cell. Different. 2:221–239.

Lagoo AS, Lagoo–Deenadayalan S, Lorenz HM, Byrne J, Barber WH, Hardy KJ (1994). IL–2, IL–4, and IFN–gamma gene expression versus secretion in superantigen–activated T cells. Distinct requirement for costimulatory signals through adhesion molecules. J. Immunol. 152:1641–1652.

Lu C, Kerbel RS (1994). Cytokines, growth factors and the loss of negative growth controls in the progression of human cutaneous malignant melanoma. Curr. Opin. Oncol. 6:212–220.

Pang G, Couch L, Batey R, Clancy R, Cripps A (1994). GM–CSF, IL–1 alpha, IL–1 beta, IL–6, IL–8, IL–10, ICAM–1 and VCAM–1 gene expression and cytokine production in human duodenal fibroblasts stimulated with lipopolysaccharide, IL–1 alpha and TNF–alpha. Clin. Exp. Immunol. 96:437–443.

Shimane M, Tani K, Maruyama K, Takahashi S, Ozawa K, Asano S (1994). Molecular cloning and characterization of G–CSF induced gene cDNA. Biochem. Biophys. Res. Commun. 199:26–32.

Su ZZ, Shen R, O'Brian CA, Fisher PB (1994). Induction of transformation progression in type 5 adenovirus–transformed rat embryo cells by a cloned protein kinase C beta 1 gene and reversal of progression by 5–azacytidine. Oncogene 9:1123–1132.

Jiang H, Fisher PB (1993). Use of a sensitive and efficient subtraction hybridization protocol for the identification of genes differentially regulated during the induction of differentiation in human melanoma cells. Mol. Cell. Different. 1:285–299.

Aharon T, Schneider RJ (1993). Selective destabilization of short–lived mRNAs with the granulocyte–macrophage colony–stimulating factor AU–rich 3' noncoding region is mediated by a contranslational mechanism. Mol. Cell. Biol. 13:1971–1980.

Jiang H, Su ZZ, Boyd J, Fisher PB (1993). Gene expression changes associated with reversible growth suppression and the induction of terminal differentiation in human melanoma cells. Mol. Cell. Different. 1:41–66.

Jiang H, Waxman S, Fisher PB (1993). Regulation of c–fos, c–jun and jun–B gene expression in human malanoma cells induced to terminally differentiate. Mol. Cell. Different. 1:197–214.

Johnson PF (1993). Identification of C/EBP basic region residues involved in DNA sequence recognition and half–site spacing preference. Mol. Cell. Biol. 13: 6919–6930.

Martinez OM, Villanueva JC, Lake J, Roberts JP, Ascher NL, Krams SM (1993). IL–2 and IL–5 gene expression in response to alloantigen in liver allograft recipients 10 and in vitro. Transplantation 55:1159–1166.

Pizarro TT, Malinowska K, Kovacs EJ, Clancy J Jr, Robinson JA, Piccinini LA (1993). Induction of TNF alpha and TNF beta gene expression in rat cardiac transplants during allograft rejection. Transplantation 56:399–404.

Anderson WF (1992). The June RAC meeting. Hum. Gene Ther. 3:459–460.

Berkner KL (1992). Expression of heterologous sequences in adenoviral vectors. Curr. Top. Microbiol. Immunol. 158:39–66.

Breviario F, d'Aniello EM, Golay J, Peri G, Bottazzi B, Bairoch A, Saccone S, Marzella R, Predazzi V, Rocchi M, et al. (1992). Interleukin–1–inducible genes in endothelial cells. Cloning of a new gene related to C–reactive protein and serum amyloid P component. J. Biol. Chem. 267:22190–22197.

Espinoza–Delgado I, Longo DL, Gusella GL, Varesio L (1992). Regulation of IL–2 receptor subunit genes in human monocytes. Differential effects of IL–2 and IFN–gamma. J. Immunol. 149:2961–2968.

Li YP, Stashenko P (1992). Proinflammatory cytokines tumor necrosis factor–alpha and IL–6, but not IL–1, down–regulate the osteocalcin gene promoter. J. Immunol. 148:788–794.

Mauviel A, Reitamo S, Remitz A, Lapierer JC, Ceska M, Baggiolini M, Walz A, Evans CH, Uitto J (1992). Leuko-regulin, a T–cell–derived cytokine, induces IL–8 gene expression and secretion in human skin fibroblasts. Demonstration and secretion in human skin fibroblasts. Demonstration of enhanced NF–kappa B binding and NF–kappa B–driven promoter activity. J. Immunol. 149:2969–2976.

Natsuka S, Akira S, Nishio Y, Hashimoto S, Sugita T, Isshiki H, Kishimoto T (1992). Macrophage differentiation–specific expression of NF–IL6, a transcription factor for interleukin–6. Blood 79:460–466.

Sprecher E, Becker Y (1992). Detection of IL–1 beta, TNF–alpha, and IL–6 gene transcription by the polymerase chain reaction in keratinocytes, Langerhans cells and peritoneal exudate cells during infection with herpes simplex virus–1. Arch. Virol. 126:253–269.

Angel P, Karin M (1991). The role of Jun, Fos and the AP–1 complex in cell–proliferation and transformation. Biochem. Biophys. Acta 1072:129–157.

Canonico AE, Conary JT, Christman BW, Meyrick BO, Brigham KL (1991). Expression of a CMV promoter driven human α–1 antitrypsin gene in cultured lung endothelial cells and the lungs of rabbits. Clin. Res. 39:219A (abstract).

Clark WH (1991). Tumour progression and the nature of cancer. Br. J. Cancer 64:631–644.

Culver KW, Anderson WF, Blaese RM (1991). Lymphocyte gene therapy. Hum. Gene Ther. 2:107–109.

Hazinski TA, Ladd PA, DeMatteo CA (1991). Localization and induced expression of fusion genes in the rat lung. Am. J. Respir. Cell Mol. Biol. 4:206–209.

Kaufman, RJ (1991). Vectors used for expression in mammalian cells. In: Gene Expression Technology, DV Goeddel (ed.), pp. 487–511.

Kay AB, Ying S, Varney V, Gaga M, Durham SR, Moqbel R, Wardlaw AJ, Hamid Q (1991). Messenger RNA expression of the cytokine gene cluster, interleukin 3 (IL–3), IL–4, IL–5, and granulocyte/macrophage colony–stimulating factor, in allergen–induced late–phase cutaneous reactions in atopic subjects. J. Exp. Med. 173:775–778.

Rosenfeld MA, Siegfried W, Yoshimura K, Yoneyama K, Fuklayama M, Stier LE, Paakko PK, Gilardi P, Stratford–Perridcaudet LD, Perricaudet M, et al. (1991). Adenovirus–mediated transfer of a recombinant alpha 1–antitrypsin gene to the lung epithelium in vivo. Science 252:431–434.

Shyu AB, Belasco JG, Greenberg ME (1991). Two distinct destabilizing elements in the c–fos message trigger deadenylation as a first step in rapid mRNA decay. Genes Dev. 2:221–231.

Ulich TR, Guo KZ, Remick D, del Castillo J, Yin SM (1991). Endotoxin–induced cytokine gene expression in vivo. III. IL–6 mRNA and serum protein expression and the in vivo hematologic effects of IL–6. J. Immunol. 146:2316–2323.

Akira S, Isshiki H, Sugita T, Tanabe O, Kinoshita S, Nishio Y, Nakajima T, Hirano T, Kishimoto T (1990). A nuclear factor for IL–6 expression (NF–IL6) is a member of a C/EBP family. EMBO J. 9:1897–1906.

Anderson WF, Blaese RM, Culver K (1990). The ADA human gene therapy clinical protocol: Points to Consider response with clinical protocol, Jul. 6, 1990. Hum. Gene Ther. 1:331–362.

Geller AI, Keyomarsi K, Bryan J, Pardee AB (1990). An efficient deletion mutant packaging system for a defective herpes simplex virus vectors: potential applications to human gene therapy and neuronal physiology. Proc. Natl. Acad. Sci. USA 87:8950–8954.

Herlyn M (1990). Human melanoma: development and progression. Cancer Metastasis Rev. 9:101–112.

Horisberger MA, McMaster GK, Zeller H, Wathelet MG, Dellis J, Content J (1990). Cloning and sequence analyses of cDNAs for interferon–beta and virus–induced human Mx proteins reveal that they contain putative guanine nucleotide–binding sites: functional study of the corresponding gene promoter. J. Virol. 64:1171–1181.

Jonat C, Rahmsdorf HJ, Park KK, Cato AC, Gebel S, Ponta H, Herrlich P (1990). Antitumor promotion and antiinflammation: down–modulation of AP–1 (Fos/Jun) activity by glucocorticoid hormone. Cell 62:1189–1204.

Nabel EG, Plautz G, Nabel GJ (1990). Site–specific gene expression in vivo by direct gene transfer into the arterial wall. Science 249:1285–1288.

Sherman ML, Datta R, Hallahan DE, Weichselbaum RR, Kufe DW (1990). Ionizing radiation regulates expression of the c–jun protooncogene. Proc. Natl. Acad. Sci. USA 87:5663–5666.

Wolff JA, Malone RW, Williams P, Chong W, Ascadi G, Jani A, Felgner PL (1990). Direct gene transfer into mouse muscle in vivo. Science 247:1465–1468.

Yang–Yen HF, Chambard JC, Sun YL, Smeal T, Schmidt TJ, Drouin J, Karin M (1990). Transcriptional interference between c–Jun and the glucocorticoid receptor: mutual inhibition of DNA binding due to direct protein–protein interaction. Cell 62:1205–1215.

Birkenmeier EH, Gwynn B, Howard S, Jerry J, Gordon JI, Landschulz, WH, McKnight SL (1989). Tissue–specific expression, developmental regulation, and genetic mapping of the gene encoding CCAAT/enhancer binding protein. Genes Dev. 3:1146–1156.

Brigham KL, Meyrick B, Christman B, Magnuson M, King G, Berry LC Jr (1989). In vivo transfection of murine lungs with a functioning prokaryotic gene using a liposome vehicle. Am. J. Med. Sci. 298:278–281.

Felgner PL, Holm M, Chan H (1989), Cationic liposome mediated transfection: Proc. West. Pharmacol. Soc. 32: 115–121.

Ishikawa M, Kerbel RS (1989). Characterization of a metastasis–deficient lectin–resistant human melanoma mutant. Int. J. Cancer 43:134–139.

Belasco JG, Higgins CF (1988). Mechanisms of mRNA decay in bacteria: a perspective. Gene 72:15–23.

Berkner KL (1988). Development of adenovirus vectors for the expression of heterologous genes. BioTechniques 6:616–629.

De Pamphilis ML, Herman SA, Martinez–Salas E, Chalifour LE, Wirak DO, Cupo DY, Miranda M (1988). Microinjecting DNA into mouse ova to study DNA replication and gene expression and to produce transgenic animals. BioTechniques 6:662–680.

Guild BC, Finer MH, Houseman DE, Mulligan RC (1988). Development of retrovirus vectors useful for expressing genes in cultured murine embryonic cells and hematopoietic cells in vivo. J. Virol. 62:3795–3801.

McGrory WJ, Bautista DS, Graham FL (1988). A simple technique for the rescue of early region I mutations into infectious human adenovirus type 5, Virology 163(2):614–617.

Felgner PL, Gadek TR, Holm, M, Roman R, Chan HW, Wenz M, Northrop JP, Ringold GM, Danielsen M (1987). Lipofection: a highly efficient, lipid–mediated DNA–transfection procedure. Proc. Natl. Acad. Sci. USA 84:7413–7417.

Ghosh–Choudhury G, Graham FL (1987). Stable transfer of a mouse dihydrofolate reductase gene into a deficient cell line using human adenovirus vector. Biochem. Biophys. Res. Commun. 147(3):964–973.

Rossi P, de Crombrugghe B (1987). Identification of a cell–specific transcriptional enhancer in the first intron of the mouse alpha 2 (type I) collagen gene. Proc. Natl. Acad. Sci. USA 84:5590–5594.

Ghosh–Choudhury G, Haj–Ahmad Y, Brinkley, P, Rudy J, Graham FL (1986). Human adenovirus cloning vectors based on infectious bacterial plasmids. Gene 50:161–171.

Haj–Ahmad Y, Graham FL (1986). Development of a helper–independent human adenovirus vector and its use in the transfer of the herpes simplex thymidine kinase gene. J. Virol. 57:257–274.

Hock RA, Miller AD (1986). Retrovirus mediated transfer and expression of drug resistance genes in human hemopoietic progenitor cells. Nature 320:275–277.

Shaw G, Kamen R. (1986). A conserved AU sequence from the 3' untranslated region of GM–CSF mRNA mediates selective mRNA degradation. Cell 46:659–667.

Stavridis JC, Deliconstantinos G, Psallidopoulos MC, Armenakas NA, Hadjiminas DJ, Hadjiminas J (1986). Construction of trans ferrin–coated liposomes for in vivo transport of exogenous DNA to bone marrow erythroblasts in rabbits. Exp. Cell Res. 164:568–572.

Fisher PB, Prignoli DR, Hermo H Jr, Weinstein IB, Pestka S (1985). Effects of combined treatment with interferon and mezerein on melanogenesis and growth in human melanoma cells. J. Interferon Res. 5:11–22.

Kaufman RJ (1985). Identification of the component necessary for adenovirus translation control and their utilization in cDNA expression vectors. Proc. Natl. Acad. Sci. USA 82:689–693.

Krowczynska A, Yenofsky R, Brawerman G (1985). Regulation of messenger RNA stability in mouse erythroleukemia cells. J. Mol. Biol. 181:231–239.

Linial M, Gunderson N, Groudine M. (1985). Enhanced transcription of c–myc in bursal lymphoma cells requires continuous protein synthesis. Science 230:1126–1132.

Nedwin GE, Svedersky LP, Bringman TS, Palladino MA Jr, Goeddel DV (1985). Effect of interleukin 2, interferon–gamma, and mitogens on the production of tumor necrosis factors alpha and beta. J. Immunol. 135:2492–2497.

Scott RE, Maercklein PB (1985). An initiator of carcinogenesis selectivity and stability inhibits stem cell differentiation: a concept that initiation of carcinogenesis involves multiple phases. Proc. Natl. Acad. Sci. USA 82:2995–2999.

Wong GG, Witek JS, Temple PA, Wilkens KM, Leary AC, Luxenberg DP, Jones SS, Brown EL, Kay RM, Orr EC, Shoemaker C, Golde DW Kaufman RJ, Hewick RM, Wang EA, Clark SC (1985). Human GM–CSF: Molecular cloning of the complementary DNA and purification of the natural and recombinant proteins. Science 228:810–815.

Schmidt A, Setoyama C, de Crombrugghe B (1985). Regulation of a collagen gene promoter by the product of viral mos oncogene. Nature 314:286–289.

Elder PK, Schmidt LJ, Ono T, Getz MJ (1984). Specific stimulation of actin gene transcription by epidermal growth factor and cycloheximide. Proc. Natl. Acad. Sci. USA 81:7476–7480.

Miller AD, Curran T, Verma IM. (1984). Deletion of the gag region from FBR murine osteosarcoma virus does not affect its enhanced transforming activity. Cell 36:51–60.

Van Doren K, Gluzman Y (1984). Efficient transformation of human fibroblasts by adenovirus–simian virus 40 recombinants. Mol. Cell. Biol. 4(8):1653–1656.

Berkner KL, Sharp PA (1983). Generation of adenovirus by transfection of plasmids. Nucleic Acids Res. 11(17):6003–6020.

Dignam JD, Lebovitz RM, Roder RG (1983). Accurate transcription initiation by RNA polymerase II in a soluble extract from isolated mammalian nuclei. Nucleic Acids Res. 11:1475–1489.

Jolly DJ, Esty AC, Subramani S, Friedmann T, Verma IM (1983). Elements in the long terminal repeat of murine retroviruses enhance stable transformation by thymidine kinase gene. Nucleic Acids Res. 11:1855–1872.

Smith GL, Mackett M, Moss B (1983). Infectious vaccinia virus recombinants that express hepatitis B virus surface antigens. Nature 302:490–495.

van Straaten F, Muller R, Curran T, van Beveren C, Verma IM. (1983). Complete nucleotide sequence of a human c–onc gene: deduced amino sequence of the human c–fos protein. Proc. Natl. Acad. Sci. USA 80:3183–3187.

Panicali D, Paoletti E (1983). Construction of poxvirus as cloning vectors: Insertion of the thymidine kinase gene from herpes simplex virus into the DNA of infectious vaccine virus. Proc. Natl. Acad. Sci. USA 79:4927–4931.

Gorman CM, Moffat LF, Howard BH (1982). Recombinant genomes which express chloramphenical acetyltransferase in mammalian cells. Mol. Cell. Biol. 2(9):1044–1051.

Schaefer–Ridder M, Wang Y, Hofschneider PH (1982). Liposomes as gene carriers: Efficient transduction of mouse L cells by thymidine kinase gene. Science 215:166–168.

Banerji J, Rusconi S, Schaffner W (1981). Expression of a beta–globin gene is enhanced by remote SV 40 DNA sequences. Cell 27:299–308.

Breathnach R, Chambon P (1981). Organization and expression of eucaryotic split genes coding for proteins. Ann. Rev. Biochem. 50:349–383.

Colbere–Garapin F, Horodniceanu F, Kourilsky P, Garapin AC (1981) A new dominant hybrid selective marker for higher eukaryotic cells. J. Mol. Biol. 150:1–14.

Goeddel DV, Leung DW, Dull TJ, Gross M, Lawn RM, McCandliss R, Seeburg PH, Ullrich A, Yelverton E, Gray PW (1981). The structure of eight distinct cloned human leukocyte interferon cDNAs. Nature 5:20–26.

Kishan Raj NB, Pitha PM (1981). Analysis of interferon mRNA in human fibroblast cells induced to produce interferon. Proc. Natl. Acad. Sci. USA 78:7426–7430.

Mulligan RC, Berg P (1981). Selection for animal cells that express the *Escherichia coli* gene coding for xanthine–guanine phosphoribosyltransferase. Proc. Natl. Acad. Sci. USA 78:2072–2076.

Ringold G, Dieckmann B, Lee F (1981). Co–expression and amplification of dihydrofolate reductase cDNA and the *Escherichia coli* XGPRT gene in Chinese hamster ovary cells. J. Mol. Appl. Genet. 1:165–175.

Sarver N, Gruss P, Law MF, Khoury G, Howley PM (1981). Bovine papilloma virus DNA: a novel eukaryotic cloning vector. Mol. Cell Biol. 1:486–496.

Corden J, Wasylyk B, Buchwalder A, Sassone–Corsi P, Kedinger C, Chambon P (1980). Promoter sequences of eukaryotic protein–coding genes. Science 209:1406–1414.

Sachs L (1980). Constitutive uncoupling of pathways of gene expression that control growth and differentiation in myeloid leukemia: a model for the origin and progression of malignancy. Proc. Natl. Acad. Sci. USA 77:6152–6156.

Urlaub G, Chasin LA (1980). Isolation of Chinese hamster cell mutants deficient in dihydrofolate reductase activity. Proc. Natl. Acad. Sci. USA 77:4216–4220.

Huberman E, Callaham MF (1979). Induction of terminal differentiation in human promyelocytic leukemia cells by tumor–promoting agents. Proc. Natl. Acad. Sci. USA 76:1293–1297.

Sachs L (1978). Control of normal cell differentiation and the phenotypic reversion of malignancy in myeloid leukaemia. Nature 274:535–539.

Bacchetti S, Graham FL (1977). Transfer of gene for thymidine kinase–deficient human cells by purified herpes simplex viral DNA. Proc. Natl. Acad. Sci. USA 74:1590–1594.

Fowler AV, Zabin I (1977). The amino acid sequence of beta–galactosidase of *Escherichia coli*. Proc. Natl. Acad. Sci. USA 74(4):1507–1510.

Tu SC, Waters CA, Hastings JW (1975). Photoexcited bacterial bioluminescence. Identity and properties of the photoexcitable luciferase. Biochemistry 14(9):1970–1974.

Armelin HA (1973). Pituitary extracts and steroid hormones in the control of 3T3 cell growth. Proc. Natl. Acad. Sci. USA 70:2702–2706.

Graham FL, van der EB AJ (1973). A new technique for the assay of infectivity of human adenovirus 5 DNA. Virology 52:456–467.

Freireich EJ, Gehan EA, Rall DP, Schmidt LH, Skipper HE (1966). Quantitative comparison of toxicity of anticancer agents in mouse, rat, hamster, dog, monkey, and man. Cancer Chemother. Rep. 50 :219–244.

Huang F., Adelman J., Jiang H., Goldstein N.I., and Fisher P.B., Differentiation Induction Subtraction hybridization (DISH): A Strategy For Cloning Genes Displaying Differential Expression During Growth Arrest And Terminal Differentiation, (1999). *Gene,* 236(1):125–131 (Exhibit B).

Huang F., Adelman J., Jiang H., Goldstein N.I., and Fisher P.B., Identification And Temporal Expression Pattern Of Genes Modified During Irreversible Growth Arrest And Terminal Differentiation In Human Melanoma Cells, (1999), *Oncogene,* 18(23):3546–52 (Exhibit C).

Jiang H. et al., The Melanoma Differentiation–Associated Gene mda–6, Which Encodes The Cyclin–Dependent Kinase Inhibitor p21, is Differentially Expressed During Growth Differentiation And Progression In Human Melanoma Cells, (1995) *Oncogene,* 10:1855–1864 (Exhibit D).

Jiang H., and Fisher, P.B., Subtraction Hybridization Identifies a Novel Melanoma Differentiation Associated Gene mda–7, Mediated During Human Melanoma Differentiation, Growth and Progression, (1995) *Oncogene* 11(12):2477–86 (Exhibit E).

Jiang, H., Su, Z–z., Lin, J.J., Goldstein, N.I., Young, C. S.H., and Fisher, P. B. The Melanoma Differentiation Associated Gene mda–7 Suppresses Cancer Cell Growth, (1996) *Proc. Natl. Acad. Sci. USA,* 93:9160–9165 (Exhibit F).

Jiang H., et al., Induction Of Differentiation In Human Promyelocytic HL–60 Leukemia Cells Activates p21, WAF1/C1P1, Expression In The Absence Of p53, (1994) *Oncogene* 9(11):3397–406 (Exhibit G).

Madireddi, M. T., et al., The Cancer Growth Suppressor Gene mda–7 Selectively Induces Apoptosis In Human Breast Cancer Cells And Inhibits Tumor Growth In Nude Mice, (1998) Proc. Natl. Acad. Sci. USA, 95(24):14400–05 (Exhibit H).

Madireddi M. T., Davis M.C. and Allis I. M., Identification Of A Novel Polypeptide Involved In The Formation Of DNA–Containing Vesicles during Macronuclear Development In Tetrahymena, (1994) *Dev. Biol.,* 165(2):418–31 (Exhibit I).

Umek R. M., et al., CCAAT–enhancer Binding Protein: A Component Of A Differentiation Switch (1991) *Science* 251(4991):288–92 (Exhibit J).

\* cited by examiner

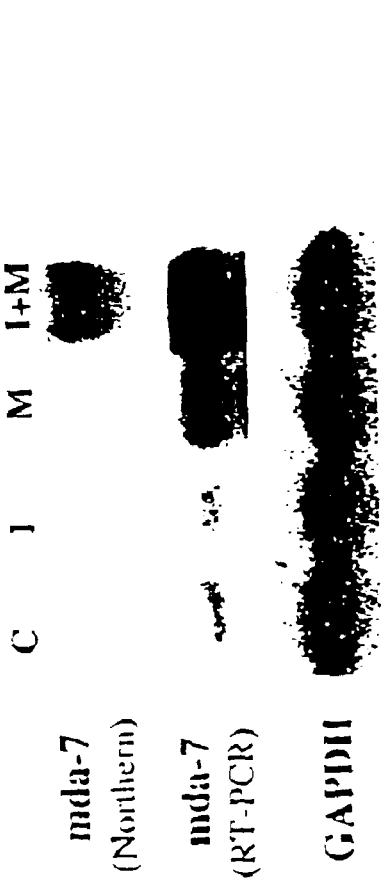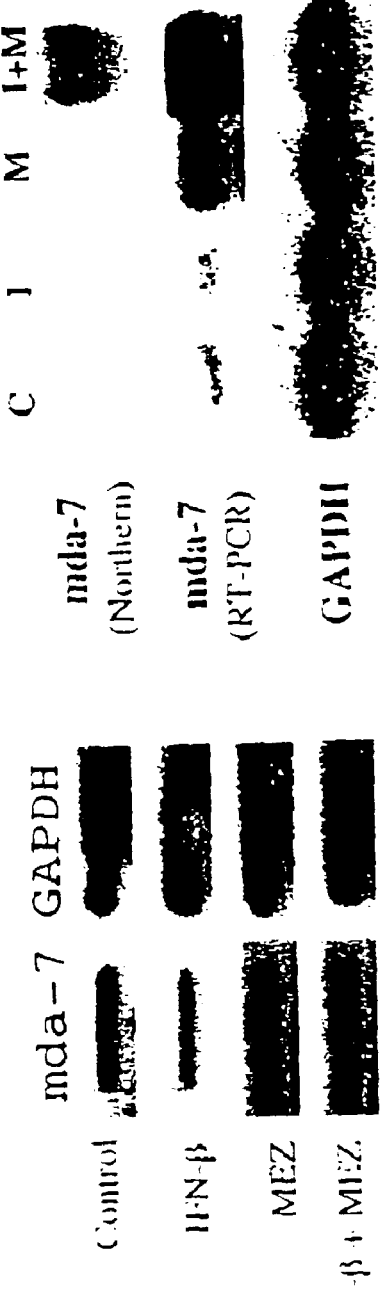
Fig. 2A
Fig. 2B
Fig. 2C
Hu. mda-7   UUGUAUUUAUUACAACUCUAUUUAAUUAAUGUCAGUAUUUCAACUGAAGUUCUAUUUAUUU
Hu. α-IFN   UAUUUAUUUAUUUAA
Hu. GM-CSF  UAAUAUUUAUAUAUAUUUAUAUAUAAAUAUAUUUAUUUAUUUAUUUAUUUAUUUAUUUA
Hu. TNF     AUUAUUUAUUAUUUAUUUAUUUAUUUAUUUA
Hu. cFos    GUUUUUAAUUUAUUAUUAAGAUGGAUUCUCAGAUAUUUAUAUUUUAUUUUUAUUUUAUUU

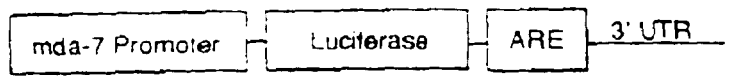
Fig. 3A
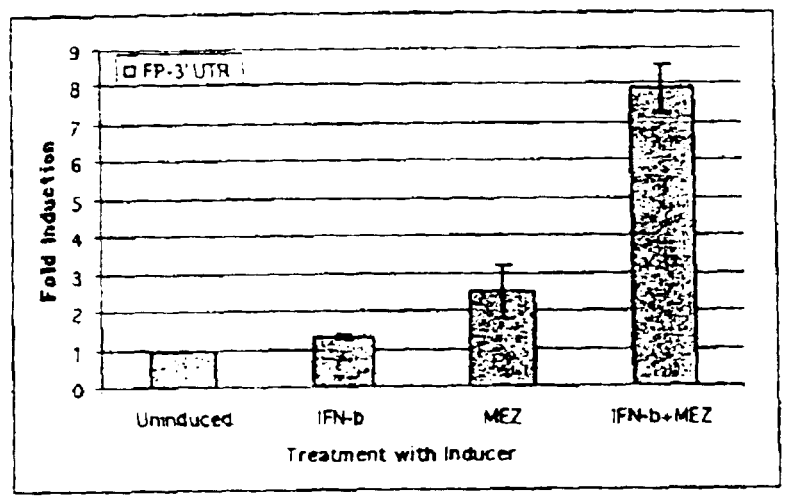
Fig. 3B
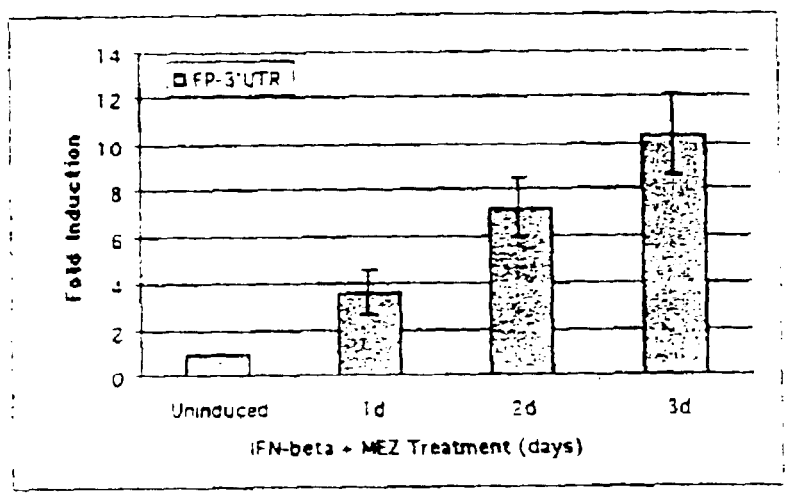

Fig 6

| | |
|---|---|
| TAATACGACTCACTATAGGGCGTCGACTCGATCACCTTTTGAACCCAGGTCTGCCTGCCTCCAAAGCTTGTACTCATAAC | 80 |
| TAGATTCTCAACTGATGTTGGGCCAAGGTTCCTAGGTTCTCTCCTTGACCTTCCTTCTGAAGTAATAATGCTATGATAAG | 160 |
| | C/EBP |
| TTCATCGGAGGCTGAGGCCCAGGCACATGTTTGCCTGAACTATCCATGTTATATGATTCCTTCCTCAGACAGAGTGAGCT | 240 |
| ACTCACGATCCCAGGTGTACCCTGAGGCCAGCCAAGGTGTATCCATGACCTCATGCCTCTGTTCCAGCCTGCCCTTTAAC | 320 |
| AGCTCATCCCACCTGCCTGCCCTCCCCGCCTATCTGCAGACAGTAGTCTAGGATTTCAGCTGCCCTGGGGGCTCATTTTC | 400 |
| CCTCTCAGCTTCCTGCTTTAGCTGTCTCCTGCCTCCCACTCACCTATTACTCCAGCACTCTCACCTGGTCTTCTTTTCTG | 480 |
| | C/EBP |
| TCTCATCACTGCCTCTTGACATCTTTATCTCATAGTAGTTAGTTAGGGGTTCTTGGTAATGCCCTAAATCCACATGGTGG | 560 |
| GAAGGGGGGAGTGGGGGAAGAGAGTGCGCTGTGGGGCTGTGCCTACTTCTGGAGGGTAAGACTCGGGCCCTCCAGGAACA | 640 |
| AAGGATTCAGGCTGGTGGCAGCTATAGCCAAGCAGACTGCTGGCCAGGGATTGCAAAGGAGTATTTTGTTTGCTTAAGAA | 720 |
| AATAAACAACACTGAGTATGAGATGGAGGGAGGGGGTGTTGGTGCCAGAGAGATTGGGAAGAGTCTGCCAAGGGTGTGTT | 800 |
| | C/EBP |
| CTACTCACTCTCCTCTTTTCTTTCATCTCCACTGAGCTGGAGGCAGTTATCCTGTCCCCACGTCACATTCCTACTCCCG | 880 |
| AP1 | |
| TTTCCCATGCCTGGACCCAGGTTGGGCAAACTCTTCCTGTAAAGAACCAGACAGGAACTATTTTAGGCTCTGTGTGCCAT | 960 |
| ATGGTCTCAGTCACAACTACTCATCTCTGCCTCTGTAGCACGAAAGCAATTAGCAACAATATGTCAACAAACATATGTGA | 1040 |
| CCCCATGAAAACTTTATTTATTATGGATACGGAAACCTGAAAATAATGTCTTTCTTTTGATTTTTCCCCAATCATTAAA | 1120 |
| | C/EBP |
| AAACGTAAAAACTACTCTTAGGTCGCAAGGTTAAGCCATTCTCAGCTTAGCAGTGGCAGGCTGGATTTGGCTTGTGACCT | 1200 |
| ACAGTTGGCCAATCCCTGATTCCCAAAATGTATTCCTCAGGGATGTGGGCAAATACTTATGGGAAGTGCTGGATTAAACA | 1280 |
| AP1 C/EBP | |
| GAGTTAAGAAGCATCAGACATTTCCAGGACGGGCTAGCACATGCCAGGGCTCTCTAACTGACCTCATTGGATTCATCTGT | 1360 |
| TTCATGGAGGATCTTGCAAGACAAGAATTCCTCAAACCTAGAGTCTGAGGACTGTGCTTTGGGAAACACTGCTCTGCTTG | 1440 |
| ATGCCCTCACTGGGCACATGGTAGAATCTAGAGCTGAGTGCCTTGCTAGCTGGAGATAGGGTCAGAGCTCTTGACTGCCC | 1520 |
| TGGCAGTCTTGACACATCACGCTGTCTGTGTCCCCTGAGTGGTTCAGAGCCACACAGGCCAAGACTAGCCCACCAGAGCA | 1600 |
| AP1 | |
| CCAGGCCTCCCAGCTTTCTGGGCTTGTCCATGCGTACATTTCCTTATTCTTCCTGGTTTCCAGAACCTAAGGAGAGGCAC | 1680 |
| ATTTTGGTTGAGTGATTATAACCCTAGGGACCATGGGTAGCTGCATGTCAGGAAACACTCCTCAACTTCCTGGCCCTGAT | 1760 |
| GGATTAAAGGAGAGGTACTTACAGGTTATTTCTTCGCTGTGGACTACTGTCCCAGCATGAATAGGGCATCATTATTGAAT | 1840 |
| TATTTTGACAGGAAGGAGACTGGTGTATGCTGCACAGTAATAATGTATTTACATGTGTACAGAGTTTACCAAGCACCTCT | 1920 |
| GTGTTGTTTTTGCCTTTGTTTATTACACTTGGGACAAATTTTTAAAATTTATACATGCAGAGACTGCAGCGCAGAGAAGC | 2000 |
| TAAGAGACTTGCCCCTGCCCACACAGCCAGTGGTAGAGCCTGAACTCAAACCCAGGTCTCATCTCACCTCAGGGGCTGCT | 2080 |
| TTCCCCATCGCTGTATTGTCCTTAAAGTGATGGGTGACTAGGCAATGAAGTAATTCTCTAGGAAAGCATGACCAATTTCC | 2160 |
| AP1 C/EBP | |
| CTTTCTCCACCTCCCTCTTTTTCCTCCACCCCTCCCCCATCAGCCCCATATATTGCCCAAATCTCCACAAAGCCTTGC | 2240 |
| TTGCCTGCAAACCTTTACTTCTGAAATGACTTCCACGGCTGGGACG | 2286 |

FIGURE 8A

| | C | I | M | I+M | TPA |
|---|---|---|---|---|---|
| cJUN/AP-1 | | | | | |
| C/EBP-β | | | | | |

SEQUENCE LISTING

<160> NUMBER OF SEQ ID NOS: 13

<210> SEQ ID NO 1
<211> LENGTH: 2286
<212> TYPE: DNA
<213> ORGANISM: Human

<400> SEQUENCE: 1

```
taatacgact cactataggg cgtcgactcg atcacctttt gaacccaggt ctgcctgcct      60
ccaaagcttg tactcataac tagattctca actgatgttg ggccaaggtt cctaggttct     120
ctccttgacc ttccttctga agtaataatg ctatgataag ctcatcggag gctgaggccc     180
aggcacatgt ttgcctgaac tatccatgtt atatgattcc ttcctcagac agagtgagct     240
actcacgatc ccaggtgtac cctgaggcca gccaaggtgt atccatgacc tcatgcctct     300
gttccagcct gcccctttaac agctcatccc acctgcctgc cctccccgcc tatctgcaga     360
cagtagtcta ggatttcagc tgccctgggg gctcattttc cctctcagct tcctgcttta     420
gctgtctcct gcctcccact cacctattac tccagcactc tcacctggtc ttcttttctg     480
tctcatcact gcctcttgac atctttatct catagtagtt agttaggggt tcttggtaat     540
gccctaaatc cacatggtgg gaaggggga gtgggggaag agagtgcgct gtgggctgt      600 gcctacttct ggagggtaag actcgggccc tccaggaaca aaggattcag gctggtggca     660
gctatagcca agcagactgc tggccaggga ttgcaaagga gtattttgtt tgcttaagaa     720
aataaacaac actgagtatg agatggaggg aggggtgtt ggtgccagag agattgggaa      780
gagtctgcca agggtgtgtt ctactcactc tcctcttttc tttcatctcc actgagctgg     840
aggcagttat cctgtccccc acgtcacatt cctactcccg tttcccatgc ctggacccag     900
```

```
gttgggcaaa ctcttcctgt aaagaaccag acaggaacta ttttaggctc tgtgtgccat      960
atggtctcag tcacaactac tcatctctgc ctctgtagca cgaaagcaat tagcaacaat     1020
atgtcaacaa acatatgtga ccccatgaaa actttattta ttatggatac ggaaacctga     1080
aaataatgtc tttcttttga ttttttcccc aatcattaaa aaacgtaaaa actactctta     1140
ggtcgcaagg ttaagccatt ctcagcttag cagtggcagg ctggatttgg cttgtgacct     1200
acagttggcc aatccctgat tcccaaaatg tattcctcag ggatgtgggc aaatacttat     1260
gggaagtgct ggattaaaca gagttaagaa gcatcagaca tttccaggac gggctagcac     1320
atgccagggc tctctaactg acctcattgg attcatctgt ttcatggagg atcttgcaag     1380
acaagaattc ctcaaaccta gagtctgagg actgtgcttt gggaaacact gctctgcttg     1440
atgccctcac tgggcacatg gtagaatcta gagctgagtg ccttgctagc tggagatagg     1500
gtcagagctc ttgactgccc tggcagtctt gacacatcac gctgtctgtg tccctgagt      1560 ggttcagagc cacacaggcc aagactagcc caccagagca ccaggcctcc cagctttctg     1620
ggcttgtcca tgcgtacatt tccttattct tcctggtttc cagaacctaa ggagaggcac     1680
attttggttg agtgattata acctagggta ccatgggtag ctgcatgtca ggaaacactc     1740
ctcaacttcc tggccctgat ggattaaagg agaggtactt acaggttatt tcttcgctgt     1800
ggactactgt cccagcatga ataggggatc attattgaat tattttgaca ggaaggagac     1860
tggtgtatgc tgcacagtaa taatgtattt acatgtgtac agagtttacc aagcacctct     1920
gtgttgtttt tgcctttgtt tattacactt gggacaaatt tttaaaattt atacatgcag     1980
agactgcagc gcagagaagc taagagactt gcccctgccc acacagccag tggtagagcc     2040
tgaactcaaa cccaggtctc atctcacctc aggggctgct ttccccatcg ctgtattgtc     2100
cttaaagtga tgggtgacta ggcaatgaag taattctcta ggaaagcatg accaatttcc     2160
ctttctccac ctccctcttt ttcctccacc cctcccccat cagcccccat atatatgccc     2220
aaatctccac aaagccttgc ttgcctgcaa acctttactt ctgaaatgac ttccacggct     2280
gggacg                                                                2286

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2
cgtcccagcc gtggaagtca t                                                 21

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 3
aggctggatt tggcttgtga c                                                 21

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer
```

```
<400> SEQUENCE: 4
ctgtttaatc cagcacttcc c                                              21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
cgcttgatga ctcagccgga a                                              21

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
tgcagattgc gcaatctgca                                                20

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide

<400> SEQUENCE: 7
cgcttgatga cttggccgga a                                              21

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
tgcagagact agtctctgca                                                20

<210> SEQ ID NO 9
<211> LENGTH: 61
<212> TYPE: RNA
<213> ORGANISM: Artificial Sequence
<220> FEATURE:
<221> NAME/KEY: misc_feature
<222> LOCATION: (1)...(61)
<223> OTHER INFORMATION: AUUUA consensus sequences from mda-7 3' UTR

<400> SEQUENCE: 9
uuguauuuau uacaacucua uuuaauuaau gucaguauuu caacugaagu ucuauuuauu    60
u                                                                    61

<210> SEQ ID NO 10
<211> LENGTH: 15
<212> TYPE: RNA
<213> ORGANISM: Artificial Sequence
<220> FEATURE:
<221> NAME/KEY: misc_feature
<222> LOCATION: (1)...(15)
<223> OTHER INFORMATION: AUUUA consensus sequences from
      alpha-interferon 3' UTR
```

```
<400> SEQUENCE: 10
uauuuauuua uuuaa                                                15

<210> SEQ ID NO 11
<211> LENGTH: 51
<212> TYPE: RNA
<213> ORGANISM: Artificial Sequence
<220> FEATURE:
<221> NAME/KEY: misc_feature
<222> LOCATION: (1)...(51)
<223> OTHER INFORMATION: AUUUA consensus sequences from
      granulocyte-monocyte colony stimulating factor 3' UTR

<400> SEQUENCE: 11
uaauauuuau auauuuauau uuuuaaaaua uuuauuuauu uauuuauuua a         51

<210> SEQ ID NO 12
<211> LENGTH: 34
<212> TYPE: RNA
<213> ORGANISM: Artificial Sequence
<220> FEATURE:
<221> NAME/KEY: misc_feature
<222> LOCATION: (1)...(34)
<223> OTHER INFORMATION: AUUUA consensus sequences from tumor necrosis
      factor 3' UTR

<400> SEQUENCE: 12
auuauuuauu auuuauuuau uauuuauuua uuua                            34

<210> SEQ ID NO 13
<211> LENGTH: 56
<212> TYPE: RNA
<213> ORGANISM: Artificial Sequence
<220> FEATURE:
<221> NAME/KEY: misc_feature
<222> LOCATION: (1)...(56)
<223> OTHER INFORMATION: AUUUA consensus sequences from fos
      proto-oncogene 3' UTR

<400> SEQUENCE: 13
guuuuuaauu uauuuauuaa gauggauucu cagauauuua uauuuuuauu uuauuu     56
```

US 6,841,362 B1

MELANOMA DIFFERENTIATION ASSOCIATED GENE-7 PROMOTER AND USES THEREOF

The invention disclosed herein was made with Government support under National Cancer Institute Grant CA35675 from the U.S. Department of Health and Human Services. Accordingly, the U.S. Government has certain rights in this invention.

BACKGROUND OF THE INVENTION

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

Conventional cancer therapy often involves surgery followed by repeated rounds of chemotherapy and/or radiation (Patterson and Harris, 1999). Although this approach can in specific instances result in complete cancer remission, in the majority of cases it is associated with severe toxic side effects and often results in only a transient abatement of the disease-state. An alternate approach for treating cancer employs agents that are potentially less toxic and which modulate the differentiation of tumor cells, a process termed "differentiation therapy" (Huberman and Callaham, 1979; Sachs, 1980; Scott and Maercklein, 1985; Waxman et al., 1991; Jiang et al., 1994; Waxman, 1995; Scott, 1997; Tamayo et al., 1999).

SUMMARY OF THE INVENTION

The present invention provides for an isolated Mda-7 promoter capable of directing transcription of a heterologous coding sequence positioned downstream therefrom, wherein the promoter is selected from the group consisting of: (a) a promoter comprising the nucleotide sequence shown in SEQ ID NO:1; (b) a promoter comprising a nucleotide sequence functionally equivalent to the nucleotide sequence shown in SEQ ID NO: 1; and (c) a promoter comprising a nucleotide sequence that hybridizes to a sequence complementary to the promoter of (a) or (b) in a Southern hybridization reaction performed under stringent conditions. The invention provides for a host cell comprising the recombinant expression construct as described herein. The invention provides for a method for expressing foreign DNA in a host cell comprising: introducing into the host cell a gene transfer vector comprising an Mda-7 promoter nucleotide sequence operably linked to a foreign DNA encoding a desired polypeptide or RNA, wherein said foreign DNA is expressed. The invention further provides for a method for treating cancer in a subject suffering therefrom which comprises administering to the subject an effective amount of a pharmaceutical composition which comprises a recombinant expression construct comprising: (a) a nucleic acid molecule that encodes a selected polypeptide; and (b) an Mda-7 promoter nucleotide sequence operably linked to the nucleic acid molecule of element (a), wherein the coding sequence will be transcribed and translated when in a host cell to produce the selected polypeptide, and the Mda-7 promoter is heterologous to the coding sequence and a pharmaceutically acceptable carrier.

BRIEF DESCRIPTION OF THE FIGURES

FIGS. 2A–2C. Determination of mda-7 transcription by nuclear run-on, mda-7 mRNA by Northern blotting and RT-PCR and a comparison of the AU-rich sequences found in the 3'-UTR of several mRNAs. (FIG. 2A) Nuclear run-on assays using nuclei isolated from Control or 24 h after treatment with IFN-β, MEZ or IFN-β+MEZ, the same concentrations as indicated in FIG. 1. GAPDH was used as an internal control. In vitro transcription assays were performed as previously described (Jiang et al., 1993). (FIG. 2B) Mda-7 message expression detected by Northern blotting and RT-PCR followed by Southern blotting. Total RNA from control (FIG. 2C) HO-1 cells and cells treated with IFN-β (I), MEZ (M) or IFN-β+MEZ (I+M) were analyzed by Northern blotting or RT-PCR/Southern using radiolabeled mda-7 cDNA as a probe as previously described (Jiang et al., 1993, 1995a; Kang et al., 1998a). GAPDH was used as an internal loading control. (C) Several cytokine genes and proto-oncogenes that contain the AUUUA consensus sequence in their 3'-UTRs. Abbreviations: Hu=human; mda-7=melanoma differentiation associated gene-7 (Jiang et al., 1995a); α-IFN alpha interferon (Goeddel et al., 1981); GM-CSF=granulocyte-monocyte colony stimulating factor (Wong et al., 1985); TNF=tumor necrosis factor (Nedwin et al., 1985); cFos=fos proto-oncogene (van Straaten et al., 1983). (SEQ ID NOS:9–13).

FIGS. 3A–3B. Posttranscriptional regulation of Luciferase mRNA as a consequence of mda-7-3' UTR addition at its 3'-end. The Luciferase expression plasmid having SV40 polyadenylation signal sequence was replaced with the 3'-UTR region (approximately 900 bp) of mda-7. A schematic representation of this chimeric construct is shown above the data. (FIG. 3A) Mda-7 3'-UTR mediated destabilization of luciferase mRNA was computed as fold induction of luciferase enzyme activity, which is seen only when stable luciferase mRNA, is synthesized. Compare the result shown in FIG. 1A of uninduced and IFN-β and MEZ treated samples. The relative activity is very high as shown in FIGS. 1A–1B as the 3'-UTR used in that assay came from SV40 while the 3'-UTR used in this study was replaced with the mda-7 3'-UTR. Similar results were obtained when an SV40 large T-antigen promoter was used in place of the mda-7 promoter. (FIG. 3B) Kinetic analysis of luciferase activity (as fold-induction) of the mda-7 promoter-luciferase-ARE- 3'-UTR construct as a function of time of treatment with IFN-β+MEZ. Luciferase assays were performed as described by Gopalkrishnan et al. (1999) and briefly in the legend to FIGS. 1A–1B.

(FIG. 4A) Actinomycin D treatment of the cells reveals differences in decay of the mda-7 mRNA as a function of treatment with various differentiation inducing drugs. Northern blotting analyses were performed on total RNA isolated from control (C)HO-1 or cells treated with IFN-β (I), MEZ (M) or IFN-β+MEZ (I+M), at the same concentrations as in FIG. 1. Twenty-four h after exposure to the inducing agent(s), acitnomycin D (Act.D, 5 μg/ml) was added (+Act.D) for 30 minutes (30') or one h (1'). Mda-7 expression was detected using a radiolabeled mda-7 cDNA probe as previously described (Jiang et al., 1995a). rRNA visualized by ethidium bromide was used as a loading control. (FIG. 4B) Effect of cycloheximide treatment on mda-7 mRNA stability relative to p21/mda-6 Untreated control (C)HO-1 cells or cells treated for 24 h with IFN-β (I), MEZ (M) or IFN-β+MEZ at the same concentrations as in FIGS. 1A–1B. After 24 h induction, cells were treated with or without cycloheximide (10 μg/ml) for 3 h and total RNA was isolated and analyzed by Northern blotting. Mda-7 expression was detected using a radiolabeled mda-7 cDNA probe (Jiang et al., 1995a). The blot was allowed to decay for 3 months, and then reprobed using a radiolabeled probe against a p21/mda-6 cDNA (Jiang et al., 1995b). rRNA visualized by ethidium bromide was used as a loading control.

(FIG. 5A) Northern blotting analysis of mda-7 message expression. Total RNA was isolated from HO-1 cells that were uninduced (C) or treated with IFN-β (I), MEZ (M) or IFN-β+MEZ (I+M) and analyzed by Northern blotting. 28S RNA was used as a loading control. Mda-7 message was detected using a random primed [$^{32}$P]-labeled mda-7 cDNA probe (18). (FIG. 5B) Indirect immunofluorescence visualization of MDA-7 protein subcellular localization. Both uninduced HO-i cells (Control; A and S) and terminally differentiated (48 h IFN-β+MEZ treated; C and D) were immuno-labeled using anti-MDA-7 specific monoclonal antibody. Anti-mouse secondary antibodies conjugated with Rhodamine enabled visualization of MDA-7 protein localization (A and C) and the DNA specific dye, DAPI was used to stain nuclei (B and D). With the exception of a cell undergoing mitosis no other cells reveal MDA-7 staining in control cultures (A and B). Terminally differentiated cells in (C) and (D) show strong punctate MDA-7 staining within the nucleus (See enlargement below (C) and (D) of a single nucleus). The arrow points to the punctate bodies to which MDA-7 localizes in the nucleus and their coincidence with DAPI bright staining regions.

FIG. 6. Mda-7 promoter sequence. Positions of specific transcription factor and TATA binding sites are indicated. The FL-mda-7-Prom sequence (SEQ ID NO:1) has been submitted to the GeneBank database, accession number AF217405.

[FIG. 7A] Schematic of the full-length mda-7 promoter and putative transcription factor binding sites. The positions for internal restriction enzyme sites for ApaI, NdeI and NheI used in deletion fragment generation are indicated in this figure. [FIG. 7B] mda-7 promoter deletions analyzed for promoter activity. [FIGS. 7C, 7D, 7E and 7F] Induction of various mda-7 promoter deletions, expressed as units of luciferase activity, in the absence of transcription factor addition (pCMV.Vec) or upon ectopic expression of specific transcription factors (cJun, CEBP/alpha or CEBP/beta) in HO-1 cells.

FIGS. 8A–8C. Protein expression pattern of the transcription factors cJun/AP-1 and C/EBP-β and their ability to transactivat the mda-7 promoter. [FIG. 8A] Whole cell lysates from HO-1 control cells (C) and those treated with IFN-β (I), MEZ (M), IFN-β+MEZ (I+M) or TPA were resolved on a 4–20% SDS-PAGE gel and transblotted onto nitrocellulose filters. Immobilized proteins were then analyzed by Western blotting using commercially available cJun/AP-1 and C/EBP-β specific antibodies. A single immunoreactive band was seen in each case. Equal protein loading was determined by Coomassie blue staining of a parallel gel. [FIG. 8B] Promoter activation using ectopically expressed cJun, C/EBP-α, C/EBP-β (S) and C/EBP-B (AS) expression plasmids in HO-1 melanoma cells. Fold induction is computed relative to control. B-galactosidase was used to normalize for variations in transfection efficiencies. [FIG. 8C] Competition of wild-type and a transactivation domain mutant version of cJun (TAM67) were compared for their ability to activate the mda-7 promoter. HO-1 cells were transfected individually with either wild-type cJun (cJun) or mutant cJun (TAM67) or a combination of wild-type to mutant cJun in different ratios.

[FIGS. 9C and 9D] Gel retardation assays using a 10- or 100-fold excess of either wild type (WT) or mutant (MT) C/EBP-B (left panel, arrow 1) or AP-1 (right panel, arrow 2) oligonucleotides. [FIGS. 9E and 9F] Super-shift assays using anti-C/EBP-B or anti-cJun/AP-1 specific antibodies. Single arrowheads indicate transcription factor DNA interaction complexes while the double arrowheads indicate the super-shifted protein-DNA complex resulting from the binding of specific antibodies to the transcription factors.

DETAILED DESCRIPTION OF THE INVENTION

Figure 1A:
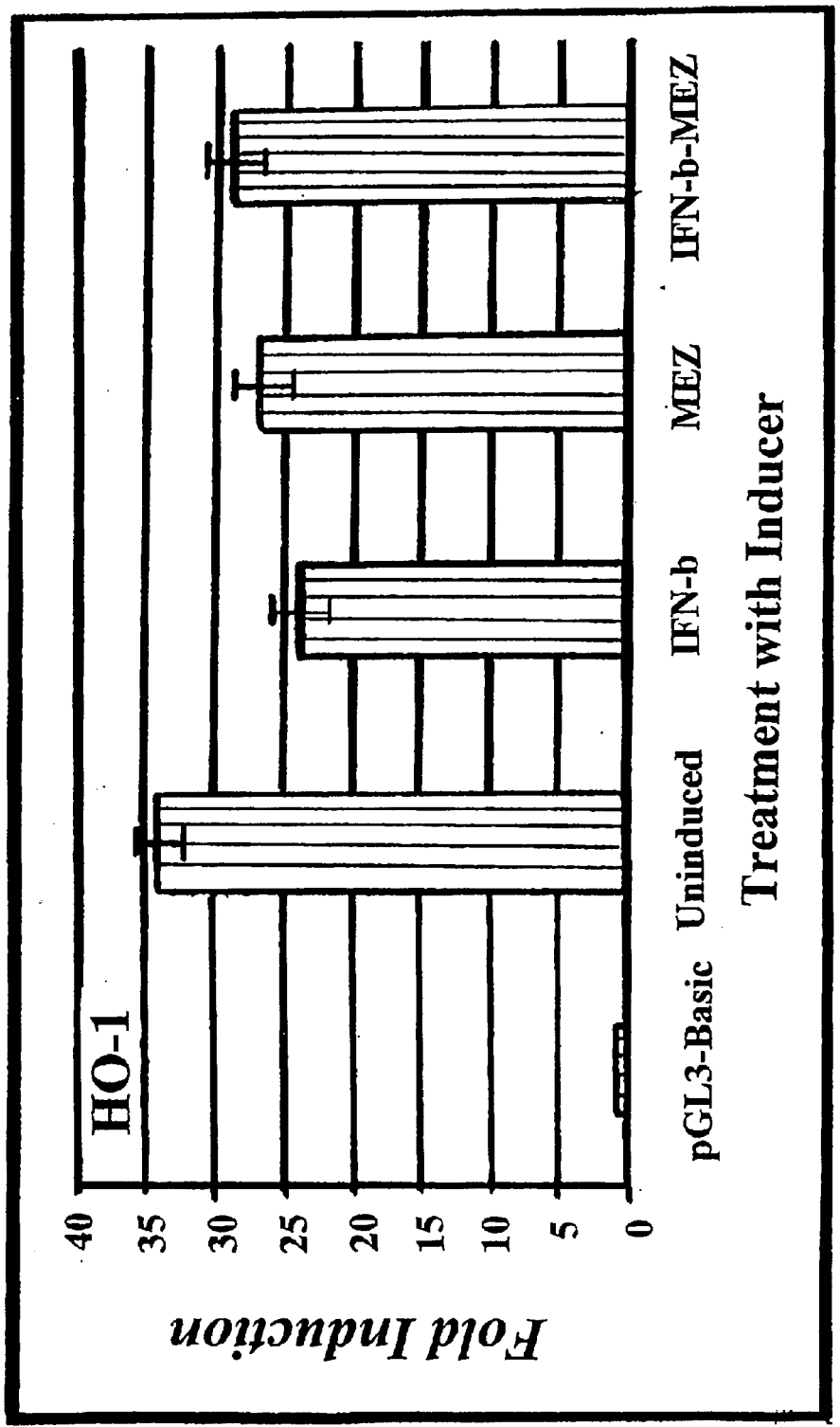
FIGS. 1A–1B. The effect of differentiation inducer drug treatment on full length mda-7 promoter activity. Fold induction of the FL-mda-7 promoter relative to the pGL3-Basic plasmid with or without differentiation inducer drug treatment in HO-1 (FIG. 1A) or MeWo (FIG. 1B) human melanoma cells. Luciferase assays were performed as previously described (Gopalkrishnan et al., 1999). In brief, the promoter-containing plasmids were transiently transfected into the different cell types using Superfect$^R$ (Qiagen) according to the manufacturer's protocol. The cells were treated with differentiation inducers (IFN-β, 2000 units/ml; MEZ, 10 ng/ml; or IFN-β+MEZ, 2000 units/ml+10 ng/ml) for 48 h following transfection and assayed for luciferase activity using the Luc+Assat Kit (Promega). The SV40-p-Galactosidase plasmid was co-transfected with the luciferase constructs and used to normalize for variations in transfection efficiencies between experiments. All experimental points were performed in triplicate and individual experiments were repeated a minimum of two times. A representative experiment is presented and standard deviations are indicated for each sample, which represents the average of triplicate reactions.

The following abbreviations are used herein: Mda-7—Melanoma differentiation associated gene-7, CMV—cytomegalovirus, The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, Molecular Cloning: A Laboratory Manual, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I–IV (D. M. Weir and C. C. Blackwell eds., 1986, Blackwell Scientific Publications).

As used in this specification and the appended claims, the singular forms "a," "an" and "the" include plural references unless the content clearly dictates otherwise.

The present invention provides for an isolated Mda-7 promoter capable of directing transcription of a heterologous coding sequence positioned downstream therefrom, wherein the promoter is selected from the group consisting of: (a) a promoter comprising the nucleotide sequence shown in SEQ ID NO:1; (b) a promoter comprising a nucleotide sequence functionally equivalent to the nucleotide sequence shown in SEQ ID NO: 1; and (c) a promoter comprising a nucleotide sequence that hybridizes to a sequence complementary to the promoter of (a) or (b) in a Southern hybridization reaction performed under stringent conditions.

In one embodiment of the invention, the promoter comprises the nucleotide sequence shown in SEQ ID NO:1.

The present invention also provides for a recombinant expression construct effective in directing the transcription of a selected coding sequence which comprises:

(a) an Mda-7 promoter nucleotide sequence as described herein; and (b) a coding sequence operably linked to the promoter, whereby the coding sequence can be transcribed and translated in a host cell, and the promoter is heterologous to the coding sequence. In another embodiment of the invention, the Mda-7 promoter comprises a human Mda-7 promoter.

In another embodiment of the invention, the human Mda-7 promoter comprises the nucleotide sequence shown in SEQ ID NO: 1 from the thymidine (T) at position 1 to the cytosine (C) at position 2240.

In another embodiment of the invention, the coding sequence encodes a tumor suppressor polypeptide.

In another embodiment of the invention, the tumor suppressor polypeptide is p21, retinoblastoma protein or p53.

The invention provides for a host cell comprising the recombinant expression construct as described herein.

In another embodiment of the invention, the host cell is stably transformed with the recombinant expression construct described herein.

In another embodiment of the invention, the host cell is a tumor cell.

In another embodiment of the invention, the host cell is a melanocyte.

In another embodiment of the invention, the cell is an immortalized cell.

In another embodiment of the invention, the tumor cell is a melanoma cell, a neuroblastoma cell, an astrocytoma cell, a glioblastomoa multifore cell, a cerival cancer cell, a breast cancer cell, a lung cancer cell or a prostate cancer cell.

The invention provides for a method for expressing foreign DNA in a host cell comprising: introducing into the host cell a gene transfer vector comprising an Mda-7 promoter nucleotide sequence operably linked to a foreign DNA encoding a desired polypeptide or RNA, wherein said foreign DNA is expressed.

In another embodiment of the invention, the promoter nucleotide sequence is identical to the sequence from the thymidine (T) at position 1 to the cytosine (C) at position 2240 of SEQ ID NO: 1.

In another embodiment of the invention, the promoter nucleotide sequence is a nucleotide sequence functionally equivalent to the identical to the Mda-7 promoter sequence from position 1 to position 2240 of SEQ ID NO: 1.

In another embodiment of the invention, the gene transfer vector encodes and expresses a reporter molecule.

In another embodiment of the invention, the reporter molecule is selected from the group consisting of beta-galactosidase, luciferase and chloramphenicol acetyltransferase.

In another embodiment of the invention, the "introducing" is carried out by a means selected from the group consisting of adenovirus infection, liposome-mediated transfer, topical application to the cell, and microinjection.

The invention provides for an isolated Mda-7 promoter capable of directing the transcription of a heterologous coding sequence positioned downstream therefrom, wherein the promoter is selected from the group consisting of (a) a promoter comprising the nucleotide sequence from the tymidine at position −2241 to the cytosine at position 0 shown in SEQ ID NO:1; (b) a promoter comprising a nucleotide sequence functionally equivalent to the promoter in element (a); and (c) a promoter comprising a nucleotide sequence that hybridizes to a sequence complementary to the promoter of element (a) or element (b) in a Southern hybridization reaction performed under stringent conditions.

The invention further provides for a method for treating cancer in a subject suffering therefrom which comprises administering to the subject an effective amount of a pharmaceutical composition which comprises a recombinant expression construct comprising: (a) a nucleic acid molecule that encodes a selected polypeptide; and (b) an Mda-7 promoter nucleotide sequence operably linked to the nucleic acid molecule of element (a), wherein the coding sequence will be transcribed and translated when in a host cell to produce the selected polypeptide, and the Mda-7 promoter is heterologous to the coding sequence and a pharmaceutically acceptable carrier.

In another embodiment of the invention, the cancer is melanoma, neuroblastoma, astrocytoma, glioblastoma multiforme, cervical cancer, breast cancer, colon cancer, prostate cancer, osteoscarcoma, or chrondosarcoma.

In another embodiment of the invention, the cancer is a cancer of the central nervous system of the subject.

In another embodiment of the invention, the administering is carried out via injection, oral administration, or topical administration.

In another embodiment of the invention, the carrier is an aqueous carrier, a liposome, or a lipid carrier.

Definitions

As used herein "therapeutic gene" means DNA encoding an amino acid sequence corresponding to a functional protein capable of exerting a therapeutic effect on cancer cells or having a regulatory effect on the expression of a function in cells, especially in skin cells (melanocytes).

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

As used herein "Mda-7 promoter" means the promoter having about 2240 base pairs (bp) derived from the 5' flanking region of the Mda-7 gene as shown in FIG. 6 beginning with (T) thymidine at nucleotide position 1 and ending with (C) cytosine at nucleotide position 2240. See SEQ ID NO: 1 as follows.

SEQ ID NO:1-MDA-7 Promoter

3'-(1)

```
TAATACGACT   CACTATAGGG   CGTCGACTCG   ATCACCTTTT   GAACCCAGGT
CTGCCTGCCT   CCAAAGCTTG   TACTCATAAC   TAGATTCTCA   ACTGATGTTG
GGCCAAGGTT   CCTAGGTTCT   CTCCTTGACC   TTCCTTCTGA   AGTAATAATG
CTATGATAAG   CTCATCGGAG   GCTGAGGCCC   AGGCACATGT   TTGCCTGAAC
TATCCATGTT   ATATGATTCC   TTCCTCAGAC   AGAGTGAGCT   ACTCACGATC
CCAGGTGTAC   CCTGAGGCCA   GCCAAGGTGT   ATCCATGACC   TCATGCCTCT
GTTCCAGCCT   GCCCTTTAAC   AGCTCATCCC   ACCTGCCTGC   CCTCCCCGCC
TATCTGCAGA   CAGTAGTCTA   GGATTTCAGC   TGCCCTGGGG   GCTCATTTTC
CCTCTCAGCT   TCCTGCTTTA   GCTGTCTCCT   GCCTCCCACT   CACCTATTAC
TCCAGCACTC   TCACCTGGTC   TTCTTTTCTG   TCTCATCACT   GCCTCTTGAC
ATCTTTATCT   CATAGTAGTT   AGTTAGGGGT   TCTTGGTAAT   GCCCTAAATC
CACATGGTGG   GAAGGGGGA    GTGGGGAAG    AGAGTGCGCT   GTGGGCTGT
GCCTACTTCT   GGAGGGTAAG   ACTCGGGCCC   TCCAGGAACA   AAGGATTCAG
GCTGGTGGCA   GCTATAGCCA   AGCAGACTGC   TGGCCAGGGA   TTGCAAAGGA
GTATTTTGTT   TGCTTAAGAA   AATAAACAAC   ACTGAGTATG   AGATGGAGGG
AGGGGGTGTT   GGTGCCAGAG   AGATTGGGAA   GAGTCTGCCA   AGGGTGTGTT
CTACTCACTC   TCCTCTTTTC   TTTCATCTCC   ACTGAGCTGG   AGGCAGTTAT
CCTGTCCCCC   ACGTCACATT   CCTACTCCCG   TTTCCCATGC   CTGGACCCAG
GTTGGGCAAA   CTCTTCCTGT   AAAGAACCAG   ACAGGAACTA   TTTTAGGCTC
TGTGTGCCAT   ATGGTCTCAG   TCACAACTAC   TCATCTCTGC   CTCTGTAGCA
CGAAAGCAAT   TAGCAACAAT   ATGTCAACAA   ACATATGTGA   CCCCATGAAA
ACTTTATTTA   TTATGGATAC   GGAAACCTGA   AAATAATGTC   TTTCTTTTGA
TTTTTTCCCC   AATCATTAAA   AAACGTAAAA   ACTACTCTTA   GGTCGCAAGG
TTAAGCCATT   CTCAGCTTAG   CAGTGGCAGG   CTGGATTTGG   CTTGTGACCT
ACAGTTGGCC   AATCCCTGAT   TCCCAAAATG   TATTCCTCAG   GGATGTGGGC
AAATACTTAT   GGGAAGTGCT   GGATTAAACA   GAGTTAAGAA   GCATCAGACA
TTTCCAGGAC   GGGCTAGCAC   ATGCCAGGGC   TCTCTAACTG   ACCTCATTGG
ATTCATCTGT   TTCATGGAGG   ATCTTGCAAG   ACAAGAATTC   CTCAAACCTA
GAGTCTGAGG   ACTGTGCTTT   GGGAAACACT   GCTCTGCTTG   ATGCCCTCAC
TGGGCACATG   GTAGAATCTA   GAGCTGAGTG   CCTTGCTAGC   TGGAGATAGG
GTCAGAGCTC   TTGACTGCCC   TGGCAGTCTT   GACACATCAC   GCTGTCTGTG
TCCCCTGAGT   GGTTCAGAGC   CACACAGGCC   AAGACTAGCC   CACCAGAGCA
CCAGGCCTCC   CAGCTTTCTG   GGCTTGTCCA   TGCGTACATT   TCCTTATTCT
TCCTGGTTTC   CAGAACCTAA   GGAGAGGCAC   ATTTTGGTTG   AGTGATTATA
ACCCTAGGGA   CCATGGGTAG   CTGCATGTCA   GGAAACACTC   CTCAACTTCC
TGGCCCTGAT   GGATTAAAGG   AGAGGTACTT   ACAGGTTATT   TCTTCGCTGT
GGACTACTGT   CCCAGCATGA   ATAGGGCATC   ATTATTGAAT   TATTTTGACA
GGAAGGAGAC   TGGTGTATGC   TGCACAGTAA   TAATGTATTT   ACATGTGTAC
```

-continued

```
AGAGTTTACC  AAGCACCTCT  GTGTTGTTTT  TGCCTTTGTT  TATTACACTT

GGGACAAATT  TTTAAAATTT  ATACATGCAG  AGACTGCAGC  GCAGAGAAGC

TAAGAGACTT  GCCCCTGCCC  ACACAGCCAG  TGGTAGAGCC  TGAACTCAAA

CCCAGGTCTC  ATCTCACCTC  AGGGGCTGCT  TTCCCCATCG  CTGTATTGTC

CTTAAAGTGA  TGGGTGACTA  GGCAATGAAG  TAATTCTCTA  GGAAAGCATG

ACCAATTTCC  CTTTCTCCAC  CTCCCTCTTT  TTCCTCCACC  CCTCCCCCAT

CAGCCCCCAT  ATATATGCCC  AAATCTCCAC  AAAGCCTTGC  TTGCCTGCAA

ACCTTTACTT  CTGAAATGAC  TTCCACGGCT  GGGACG
```

(+2286+45)

As used herein "enhancer element" is a nucleotide sequence that increases the rate of transcription of the therapeutic genes or genes of interest but does not have promoter activity. An enhancer can be moved upstream, downstream, and to the other side of a promoter without significant loss of activity.

Two DNA or polypeptide sequences are "substantially homologous" when at least about 80% (preferably at least about 90%, and most preferably at least about 95%) of the nucleotides or amino acids match over a defined length of the molecule. As used herein, "substantially homologous" also refers to sequences showing identity to the specified DNA or polypeptide sequence. DNA sequences that are substantially homologous can be identified in a Southern hybridization, experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra.

A sequence "functionally equivalent" to a Mda-7 promoter sequence is one which functions in the same manner as the Mda-7 promoter sequence. Thus, a promoter sequence "functionally equivalent" to the Mda-7 promoter described herein is one which is capable of directing transcription of a downstream coding sequence in substantially similiar timeframes of expression and in substantially similar amounts and with substantially similar tissue specificity as the Mda-7 promoter.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, procaryotic sequences, cDNA from eucaryotic mRNA, genomic DNA sequences from eucaryotic (e.g., mammalian) sources, viral RNA or DNA, and even synthetic nucleotide sequences. A transcription termination sequence will usually be located 3' to the coding sequence.

DNA "control sequences" refers collectively to promoter sequences, polyadenylation signals, transcription termination sequences, upstream regulatory domains, enhancers, and the like, untranslated regions, including 5'-UTRs and 3'-UTRs, which collectively provide for the transcription and translation of a coding sequence in a host cell.

"Operably linked" refers to an arrangement of nucleotide sequence elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extra-chromosomal plasmids. This stability is demonstrated by the ability of the eucaryotic cell to establish cell lines or clones comprised of a population of daughter cells containing the exogenous DNA.

A "heterologous" region of a DNA construct is an identifiable segment of DNA within or attached to another DNA molecule that is not found in association with the other molecule in nature. For example, a sequence encoding a protein other than an Mda-7 is considered a heterologous sequence when linked to an Mda-7 promoter. Similarly, a sequence encoding an Mda gene (i.e., Mda-6, Mda-5) will be considered heterologous when linked to an Mda gene promoter with which it is not normally associated. Another example of a heterologous coding sequence is a construct where the coding sequence itself is not found in nature (e.g., synthetic sequences having codons different from the native gene). Likewise, a chimeric sequence, comprising a heterologous structural gene and a gene encoding an mda or a portion of an Mda, linked to an Mda promoter, whether derived from the same or a different Mda gene, will be considered heterologous since such chimeric constructs are not normally found in nature. Allelic variation or naturally occurring mutational events do not give rise to a heterologous region of DNA, as used herein.

Vectors

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses, or phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic.

The gene transfer vector of the present invention may additionally comprise a gene encoding a marker or reporter molecule to more easily trace expression of the vector.

The particular reporter molecule which can be employed in the present invention is not critical thereto. Examples of such reporter molecules which can be employed in the present invention are well-known in the art and include beta-galactosidase (Fowler et al, Proc. Natl. Acad. Sci., USA, 74:1507 (1977)), luciferase (Tu et al, Biochem., 14:1970 (1975)), and chloramphenicol acetyltransferase (Gorman et al, Mol. Cell Biol., 2:1044–1051 (1982)).

The gene transfer vector may contain more than one gene encoding the same or different foreign polypeptides or RNAs.

The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention.

Examples of such plasmids which can be employed in the present invention include pGL3-based plasmids (Promega). An example of such DNA viruses which can be employed in the present invention are adenoviruses.

Adenoviruses have attracted increasing attention as expression vectors, especially for human gene therapy (Berkner, Curr. Top. Microbiol. Immunol., 158:39–66 (1992)).

Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: Adenovirus DNA, Doerfler, Ed., Martinus Nijhoff Publishing, Boston, pp. 408–441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.).

Methods for producing adenovirus vectors are well-known in the art (Berkner et al, Nucleic Acids Res., 11:6003–6020 (1983); van Doren et al, Mol. Cell. Biol., 4:1653–1656 (1984); Ghosh-Choudhury et al, Biochem. Biophys. Res. Commun., 147:964–973 (1987); McGrory et al, Virol., 163:614–617 (1988); and Gluzman et al, In: Eurkaryotic Viral Vectors, Ed. Gluzman, Y. pages 187–192, Cold Spring Harbor Laboratory (1982)).

Derivative Nucleic Acid Molecules

Derivative molecules would retain the functional property of the Mda-7 promoter, namely, the molecule having such substitutions will still permit the tissue specific expression of the gene of interest. Modification is permitted so long as the derivative molecules retain its increased potency compared to Mda-7 promoter alone and its tissue specificity.

Examples of therapeutic genes include suicide genes. These are genes sequences the expression of which produces a protein or agent that inhibits melanoma tumor cell growth or induces melanoma tumor cell death. Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill skin cancer cells or produce cytokines or other cytotoxic agents which directly or indirectly inhibit the growth of or kill the melanoma cancer cell.

Suitable enzymes include thymidine kinase (TK), xanthine-guanine phosphoribosyltransferase (GPT) gene from E. coli or E. coli cytosine deaminase (CD), or hypoxanthine phosphoribosyl transferase (HPRT).

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include Pseudomonas exotoxin A and S; diphtheria toxin (DT); E. coli LT toxins, Shiga toxin, Shiga-like toxins (SLT-1, -2), ricin, abrin, supporin, and gelonin.

Suitable cytokines include interferons, GM-CSF interleukins, tumor necrosis factor (TNF) (Wong G, et al., Human GM-CSF: Molecular cloning of the complementary DNA and purification of the natural and recombinant proteins. Science 1985; 228:810); WO9323034 (1993); Horisberger M. A., et al., Cloning and sequence analyses of cDNAs for interferon-beta and virus-induced human Mx proteins reveal that they contain putative guanine nucleotide-binding sites: functional study of the corresponding gene promoter. Journal of Virology, 1990 Mar, 64(3):1171–81; Li Y P et al., Proinflammatory cytokines tumor necrosis factor-alpha and IL-6, but not IL-1, down-regulate the osteocalcin gene promoter. Journal of Immunology, Feb. 1, 1992, 148(3):788–94; Pizarro T. T., et al. Induction of TNF alpha and TNF beta gene expression in rat cardiac transplants during allograft rejection. Transplantation, 1993 Aug., 56(2):399–404). (Breviario F., et al., Interleukin-1-inducible genes in endothelial cells. Cloning of a new gene related to C-reactive protein and serum amyloid P component. Journal of Biological Chemistry, Nov. 5, 1992, 267 (31):22190–7; Espinoza-Delgado I., et al., Regulation of IL-2 receptor subunit genes in human monocytes. Differential effects of IL-2 and IFN-gamma. Journal of Immunology, Nov. 1, 1992, 149(9):2961–8; Algate P. A., et al., Regulation of the interleukin-3 (IL-3) receptor by IL-3 in the fetal liver-derived FL5.12 cell line. Blood, 1994 May 1, 83(9):2459–68; Cluitmans F. H., et al., IL-4 down-regulates IL-2-, IL-3-, and GM-CSF-induced cytokine gene expression in peripheral blood monocytes. Annals of Hematology, 1994 Jun., 68(6):293–8; Lagoo, A. S., et al., IL-2, IL-4, and IFN-gamma gene expression versus secretion in superantigen-activated T cells. Distinct requirement for costimulatory signals through adhesion molecules. Journal of Immunology, Feb. 15, 1994, 152(4):1641–52; Martinez 0. M., et al., IL-2 and IL-5 gene expression in response to alloantigen in liver allograft recipients and in vitro. Transplantation, 1993 May, 55(5):1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. Clinical and Experimental Immunology, 1994 Jun., 96(3):437–43; Ulich T. R., et al., Endotoxin-induced cytokine gene expression in vivo. III. IL-6 mRNA and serum protein expression and the in vivo hematologic effects of IL-6. Journal of Immunology, Apr. 1, 1991, 146(7):2316–23; Mauviel A., et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. Journal of Immunology, Nov. 1, 1992, 149(9):2969–76).

Growth factors include Transforming Growth Factor-.alpha. (TGF-alpha) and beta (TGF-beta), cytokine colony stimulating factors (Shimane M., et al., Molecular cloning and characterization of G-CSF induced gene cDNA. Biochemical and Biophysical Research Communications, Feb. 28, 1994, 199(1):26–32; Kay A. B., et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. Journal of Experimental Medicine, Mar. 1, 1991, 173(3):775–8; de Wit H, et al., Differential regulation of M-CSF and IL-6 gene expression in monocytic cells. British Journal of Haematology, 1994 Feb., 86(2):259–64; Sprecher E., et al., Detection of IL-1 beta, TNF-alpha, and IL-6 gene transcription by the polymerase chain reaction in keratinocytes, Langerhans cells and peritoneal exudate cells during infection with herpes simplex virus-1. Archives of Virology, 1992, 126(1–4):253–69).

Preferred vectors for use in the methods of the present invention are viral including adenoviruses, retroviral, vectors, adeno-associated viral (AAV) vectors.

The viral vector selected should meet the following criteria: 1) the vector must be able to infect the tumor cells and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. PNAS USA, 1977 74:1590; Berkner, K. L.: Development of adenovirus vectors for expression of heterologous genes. Biotechniques, 1988 6:616; Ghosh-Choudhury G., et al., Human adenovirus cloning vectors based on infectious bacterial plasmids. Gene 1986; 50:161; Hag-Ahmand Y., et al., Development of a helper-independent human adenovirus vector and its use in the transfer of the herpes simplex virus thymidine kinase gene. J Virol 1986; 57:257; Rosenfeld M., et al., Adenovirus-mediated transfer of a recombinant .alpha..sub.1-antitrypsin gene to the lung epithelium in vivo. Science 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. PNAS USA, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. PNAS USA, 1990 87:8950).

Another vector for mammalian gene transfer is the bovine papilloma virus-based vector (Sarver N. et al., Bovine papilloma virus DNA: A novel eukaryotic cloning vector. Mol Cell Biol 1981; 1:486). Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. Proc Natl Acad Sci USA 1982; 79:4927; Smith et al. infectious vaccinia virus recombinants that express hepatitis B virus surface antigens. Nature, 1983 302:490.)

Retroviruses are packages designed to insert viral genes into host cells (Guild B, et al., Development of retrovirus vectors useful for expressing genes in cultured murine embryonic cells and hematopoietic cells in vivo. J Virol 1988; 62:795; Hock R. A., et al., Retrovirus mediated transfer and expression of drug resistance genes in human hemopoietic progenitor cells. Nature 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Markers and amplifiers can also be employed in the subject expression systems. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthine-guanine phosporibosyl transferase gene, which can be selected for in medium containing mycophenolic acid and xanthine (Mulligan et al. (1981) Proc. Natl. Acad. Sci. USA 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) J. Mol. Biol. 150:1–14). Useful markers for other eucaryotic expression systems, are well known to those of skill in the art.

Infection can be carried out in vitro or in vivo. In vitro infection of cells is performed by adding the gene transfer vectors to the cell culture medium. When infection is carried out in vivo, the solution containing the gene transfer vectors may be administered by a variety of modes, depending on the tissue which is to be infected. Examples of such modes of administration include injection of gene transfer vectors into the skin, topical application onto the skin, direct application to a surface of epithelium, or instillation into an organ (e.g., time release patch or capsule below the skin or into a tumor).

Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) Proc. Natl. Acad. Sci. USA 77:4216–4220; Rungold et al. (1981) J. Mol. and Appl. Genet. 1:165–175.

The above-described system can be used to direct the expression of a wide variety of procaryotic, eucaryotic and viral proteins, including, for example, viral glycoproteins suitable for use as vaccine antigens, immunomodulators for regulation of the immune response, hormones, cytokines and growth factors, as well as proteins useful in the production of other biopharmaceuticals.

It may also be desirable to produce mutants or analogs of the proteins of interest. Mutants or analogs may be prepared by the deletion of a portion of the sequence encoding the protein, by as insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

For purposes of the present invention, it is particularly desirable to further engineer the coding sequence to effect secretion of the polypeptide from the host organism. This enhances clone stability and prevents the toxic build up of proteins in the host cell so that expression can proceed more efficiently. Homologous signal sequences can be used for this purpose with proteins normally found in association with a signal sequence. Additionally, heterologous leader sequences which provide for secretion of the protein can be added to the constructs. Preferably, processing sites will be included such that the leader fragment can be cleaved from the protein expressed therewith. (See, e.g., U.S. Pat. No. 4,336,246 for a discussion of how such cleavage sites can be introduced). The leader sequence fragment typically encodes a signal peptide comprised of hydrophobic amino acids.

In one embodiment of the invention, a heterologous gene sequence, i.e., a therapeutic gene, is inserted into the nucleic acid molecule of the invention. Other embodiments of the isolated nucleic acid molecule of the invention include the addition of a single enhancer element or multiple enhancer elements which amplify the expression of the heterologous therapeutic gene without compromising tissue specificity.

The transformation procedure used depends upon the host to be transformed. Mammalian cells can conveniently be transformed using, for example, DEERE-dextran based procedures, calcium phosphate precipitation (Graham, F. L. and Van der Eb, A. J. (1973) Virology 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) Science 247:1465–1468). Liposome-mediated gene transfer can also be accomplished using known methods. See, e.g., Hazinski et al., (1991) Am. J. Respir. Cell Mol. Biol. 4:206–209; Brigham et al. (1989) Am. J. Med. Sci. 298:278–281; Canonico et al. (1991) Clin. Res. 39:219A; and Nabel et al. (1990) Science 249:1285–1288. Targeting agents, such as antibodies directed against surface antigens expressed on specific cell types, can be covalently conjugated to the liposomal surface so that the nucleic acid can be delivered to specific tissues and cells for local administration.

Human Gene Therapy and Diagnostic Use of Vector

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991). In addition, U.S. Pat. No. 5,399,346 (Anderson, W. F. et al., Mar. 21, 1995, U.S. Ser. No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 910 days before reinfusion (Culver et al., 1991). As the length of time the target cells are left in culture increases, the possibility of contamination also increases, therefore a shorter protocol would be more beneficial.

This invention provides for the construction of retrovirus vectors containing the mda-7 promoter linked to a gene of interest for use in gene therapy or for diagonistic uses. The efficiency of transduction of these vectors can be tested in cell culture systems.

Uses of the Compositions of the Invention

This invention involves targeting a gene-of-interest to a cancer cell so that the protein encoded by the gene is expressed and directly or indirectly ameliorate the diseased state.

After infecting a susceptible cell, the transgene driven by a specific promoter in the vector expresses the protein encoded by the gene. The use of the highly specific gene vector will allow selective expression of the specific genes in cancer cells.

The present invention relates to a process for administering modified vectors into the skin to treat skin cancer or disorders associated with the skin. More particularly, the invention relates to the use of vectors carrying functional therapeutic genes to produce molecules that are capable of directly or indirectly affecting cells in the skin to repair damage sustained by the cells from defects, disease or trauma.

Preferably, for treating defects, disease or damage of cells in the skin, vectors of the invention include a therapeutic gene or transgenes, for example a gene encoding TK. The genetically modified vectors are administered into the skin to treat defects, disease such as skin cancer by introducing a therapeutic gene product or products into the skin that enhance the production of endogenous molecules that have ameliorative effects in vivo.

The basic tasks in the present method of the invention are isolating the gene of interest, selecting the proper vector vehicle to deliver the gene of interest to the body, administering the vector having the gene of interest into the body, and achieving appropriate expression of the gene of interest. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

In one embodiment of the invention, the gene of interest (desired coding sequence) is a tumor suppressor gene. The tumor suppressor gene may be p21, RB (retinoblastoma) or p53. One of skill in the art would know of other tumor suppressor genes. Recent U.S. Pat. Nos. 6,025,127 and 5,912,236 are hereby incorporated by reference to more explicitly describe the state of the art as to tumor suppressor genes.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

The methods described below to modify vectors and administering such modified vectors into the skin are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 µg of plasmid or DNA sequences is cleaved by one unit of enzyme in about 20 µl of buffer solution. Typically, an excess of restriction enzyme is used to insure complete digestion of the DNA substrate.

Incubation times of about one hour to two hours at about 37 degree. C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980). Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20.degree. C. to 25.degree. C. in 50 mM Tris (pH 7.6) 50 mM NaCl, 6 mM MgCl.sub.2, 6 mM DTT and 5–10.mu.M dNTPs. The Klenow fragment fills in at 5' sticky ends but chews back protruding 31 single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with sl nuclease or Bal-31 results in hydrolysis of any single-stranded portion.

Ligations are performed in 10–50 µl volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in Gene Expression Technology, edited by D. V. Goeddel (1991).

Many methods for inserting functional DNA transgenes into cells are known in the art. For example, non-vector methods include nonviral physical transfection of DNA into cells; for example, microinjection (DePamphilis et al., BioTechnique 6:662–680 (1988)); liposomal mediated transfection (Felgner et al., Proc. Natl. Acad. Sci. USA, 84:7413–7417 (1987), Felgner and Holm, Focus 11:21–25 (1989) and Felgner et al., Proc. West. Pharmacol. Soc. 32: 115–121 (1989)) and other methods known in the art.

Administration of Modified Vectors Into Subject

One way to get DNA into a target cell is to put it inside a membrane bound sac or vesicle such as a spheroplast or liposome, or by calcium phosphate precipitation (CaPO.sub.4) (Graham F. and Van der Eb, A., Virology 52:456 1973; Schaefer-Ridder M., et al., a Liposomes as gene carriers: Efficient transduction of mouse L cells by thymidine kinase gene. Science 1982; 215:166; Stavridis J. C., et al., Construction of transferrin-coated liposomes for in vivo transport of exogenous DNA to bone marrow erythroblasts in rabbits. Exp Cell Res 1986; 164:568–572).

A vesicle can be constructed in such a way that its membrane will fuse with the outer membrane of a target cell. The vector of the invention in vesicles can home into the cancer cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation. Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, allows multiple administrations simultaneously in several different sites or the same site using the same viral suspension. Multiple injections may consist of a mixture of therapeutic genes.

Survival of the Modified Vectors so Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)).

For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)).

Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)).

The present invention provides methods for maintaining and increasing expression of therapeutic genes using a skin specific promoter.

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor, Proc. Natl. Acad. Sci. USA 70:2702 (1973)).

For example, in the present invention, CMV enhancer sequences are used with the Mda-7 promoter to increase therapeutic gene expression. Therapeutic gene expression may also be increased for long term stable expression after injection using cytokines to modulate promoter activity.

The methods of the invention are exemplified by preferred embodiments in which modified vectors carrying a therapeutic gene are injected intracerebrally into a subject.

The most effective mode of administration and dosage regimen for the molecules of the present invention depends upon the exact location of the melanoma being treated, the severity and course of the cancer, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on mg/m.sup.2 of surface area is described by Freireich, E. J., et al. Cancer Chemother., Rep. 50 (4):219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve cures may be further reduced with schedule optimization.

Advantages of the Invention

The Mda-7 promoter of the invention exhibits melanocyte tissue specificity. Since the Mda-7 promoter of the invention is tissue-specific it can only be activated in the targeted tissue, i.e., the skin. Therefore, the genes of interest driven by the Mda-7 promoter will be differentially expressed in these cells, minimizing systemic toxicity.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Regulation of Mda-7 Gene Expression During Human Melanoma Differentiation

Induction of irreversible growth arrest and terminal differentiation in human melanoma cells following treatment with recombinant human fibroblast interferon (IFN-β) and mezerein (MEZ) results in elevated expression of a specific melanoma differentiation associated gene, mda-7. Experiments were conducted to define the mechanism involved in the regulation of mda-7 expression in differentiating human melanoma cells. The mda-7 gene is actively transcribed in uninduced HO-1 human melanoma cells and the rate of transcription of mda-7 is not significantly enhanced by treatment with IFN-β, MEZ or IFN-β+MEZ. The high basal activity of the mda-7 promoter in uninduced melanoma cells and the absence of enhancing effect upon treatment with differentiation inducers is corroborated by transfection studies using the promoter region of mda-7 linked to a luciferase reporter gene containing the SV40 polyadenylation signal sequence. RT-PCR analysis detects the presence of low levels of mda-7 transcripts in uninduced and concomitant increases in differentiation inducer treated HO-1 cells. However, steady-state mda-7 mRNA is detected only in IFN-β+MEZ and to a lesser degree in MEZ treated cells. We show that induction of terminal differentiation of HO-1 cells with IFN-β+MEZ dramatically increases the half-life of mda-7 mRNA while treatment with cycloheximide results in detectable mda-7 mRNA in control and inducer treated cells. These observations confirm constitutive activity of the mda-7 promoter in HO-1 cells irrespective of differentiation status suggesting posttranscriptional processes as important determinants of MDA-7 expression during terminal differentiation. The 3'UTR region of mda-7 contains AU-rich elements (ARE) that contribute to rapid mda-7 mRNA turnover during proliferation and reversible differentiation, a process controlled by a labile protein factor(s). Substitution of the SV40 polyadenylation signal sequence in the luciferase reporter plasmid with the mda-7-ARE-3'-UTR renders the Luciferase message unstable when expressed in proliferating and reversibly differentiated melanoma cells. In contrast, the luciferase message is stabilized when the mda-7-ARE-3'-UTR construct is expressed in terminally differentiated HO-1 cells. These, results provide compelling evidence that mda-7 expression during terminal differentiation in human melanoma cells is regulated predominantly at a posttranscriptional level.

In many instances, neoplastic growth results from the failure of cancer cells to undergo normal programs of differentiation. It is hypothesized that this deficiency to respond to the appropriate cell growth and differentiation signals is a consequence of lack of expression or reduced expression of genes necessary for maintaining these processes in cancer cells, rather than mutation and loss of function of these genetic elements. This hypothesis is supported by the observation that specific differentiation inducers can reprogram gene expression in cancer cells to that of more normal cells resulting in a concomitant loss of proliferation ability and induction of terminal differentiation (Waxman et al., 1991; Jiang and Fisher, 1993; Jiang et al., 1994; Waxman, 1995; Wada et al., 1997). Lack of proper gene expression in cancer cells may be a consequence of defects in transcriptional and/or posttranscriptional events that result in the loss of threshold levels of functional gene products required to induce terminal cell differentiation. In the case of human melanoma cells, a combinatorial treatment protocol comprising IFN-β plus MEZ results in a rapid and irreversible loss of growth potential and terminal differentiation (Fisher et al., 1985; Jiang and Fisher, 1994; Jiang et al., 1994). To define the gene expression changes associated with and potentially controlling growth and differentiation in human melanoma cells a modified subtraction hybridization scheme is being used (Jiang and Fisher, 1994). This strategy has resulted in the identification and cloning of a series of melanoma differentiation associated (mda) genes implicated in growth control, differentiation and apoptosis (Jiang and Fisher, 1993; Jiang et al., 1994, 1995a,b, 1996; Su et al., 1998; Huang et al., 1999a, b; Madireddi et al., 1999).

One of the mda genes, mda-7, is a novel gene whose expression correlates with the induction of terminal differentiation in human melanoma cells (Jiang et al., 1995a). This gene is expressed at high levels in actively proliferating normal human melanocytes, whereas its expression is reduced during disease progression to metastasis (Jiang et al., 1995a). The mda-7 cDNA encodes a polypeptide of 23.8-kDa and when ectopically expressed in tumor cells of various origins induces growth suppression and apoptosis (Jiang et al., 1995a, 1996; Su et al., 1998; Madireddi et al., 1999). The cellular function of mda-7 remains to be defined, however recent findings suggest a potential involvement of this gene in chromatin remodeling during mitosis and differentiation (data not shown). On the basis of mda-718 significant functions in mitosis, differentiation and induction of programmed cell death in diverse cancer cell types, analysis of its gene expression controls is warranted. Foremost in this analysis is the fundamental premise of the "differentiation therapy" hypothesis, i.e., differentiation drug induced transcriptional and/or posttransriptional changes may directly influence the production of stable and functional gene products involved in terminal cell differentiation.

A general mechanism by which diverse organisms regulate gene expression is by controlling the cytoplasmic concentration of individual gene transcripts (Rajagopalan and Malter, 1997). Cellular RNA levels are generally altered by changes in transcription, RNA processing and mRNA decay (Ross, 1996; Fontes et al., 1999). Although the process of mRNA synthesis is well understood, the cellular mechanisms controlling RNA degradation are less clear. Nonetheless, recent studies indicate that gene expression can be regulated through changes in mRNA stability as a consequence of altering physiological conditions (Belasco and Higgins, 1988; Spicher et al., 1998). A growing inventory of genes, including growth factors (Shaw and Kamen, 1986), cytokines (Aharon and Schneider, 1993), and proto-oncogenes (Shyu et al., 1991), are regulated by posttranscriptional decay of their messages. The magnitude of change in gene expression due to posttranscriptional mechanisms is often relatively small, yet even a two- to three-fold increase or decrease in mRNA or protein abundance can have a significant biological impact (Spicher et al., 1998). With specific oncogenes and their normal cellular homologues, such as v-fos and c-fos, respectively, changes in the 3'-untranslated region (UTR) can profoundly affect phenotypic properties. V-fos is capable of transforming normal rat fibroblast cells, whereas c-fos is impaired in this function. However, deletions in the 3'-UTR region of c-fos convert this proto-oncogene into a transforming oncogene (Miller et al., 1984). It is postulated that the specific deletions of the 31-UTR result in the stabilization of the c-fos mRNA, thereby inducing an abnormal level of c-FOS protein and oncogenic properties.

Little is currently known about expression control and regulation of the mda-7 gene during proliferation and terminal differentiation. To understand potential transcription and posttransciptional regulatory factor(s) determining mda-7 gene expression, we have cloned and characterized the promoter of this gene. The mda-7 gene is transcribed and its promoter is operative in uninduced HO-1 human melanoma cells, whereas stable mRNA is only detected in HO-1 cells treated with IFN-β+MEZ and to a much lower extent in MEZ treated cells. The half-life of mda-7 mRNA increases in terminally differentiated HO-1 cells and cycloheximide treatment results in discernible mda-7 mRNA in uninduced and inducer treated HO-1 cells. An important aspect of mda-7 gene expression regulation is posttranscriptional control by message destabilization regulated by the presence of AUUUA destabilization consensus sequences found in its 3'-UTR. During terminal differentiation the mda-7 message is stabilized. The present experiments indicate that a major level of mda-7 gene expression regulation occurs posttranscriptionally by altering mRNA stability thereby insuring a precise regulation of gene expression and its functional consequences during human melanoma terminal differentiation.

Cloning of the mda-7 Promoter and Activity of the Promoter in Uninduced and Differentiation Inducer Treated Human Melanoma Cells Expression of mda-7 corresponds with induction of terminal differentiation in human melanoma cells (Jiang et al., 1995a). Northern blotting reveals a significant amount of stable mda-7 message when human melanoma cells (HO-1) are induced to terminally differentiate after a 24 or 96 h treatment with a combination of IFN-β plus the PKC activator MEZ (Jiang et al., 1995a). Quantitatively less mda-7 mRNA is also apparent in HO-1 cells treated only with MEZ for 96 h (Jiang et al., 1995a). However, unlike IFN-β+MEZ which induce irreversible growth arrest and terminal differentiation in HO-1 cells, MEZ induced growth suppression and differentiation are reversible (Fisher et al., 1985; Jiang et al., 1993, 1995a; Jiang et al., 1994). Removal of MEZ from HO-1 cells followed by replacement with fresh growth medium (DMEM, 5% FCS) results in a loss of differentiated properties and a return to control growth rates (Fisher et al., 1985; Jiang et al., 1993, 1995a; Jiang et al., 1994). In this reversible differentiation process, removal of MEZ results in abrogation of mda-7 expression. This finding suggests that mda-7 A gene expression is directly responsive to MEZ treatment and may be activated by a PKC-mediated pathway. The significant difference in the accumulation of mda-7 message following induction of terminal differentiation versus induction of reversible differentiation implicates posttranscriptional processes, such as mRNA processing and/or stabilization, in sustaining steady state mda-7 message levels in terminally differentiated HO-1 cells.

To define the mechanism of mda-7 gene regulation and to establish a possible role for transcriptional activation of the mda-7 gene during melanoma terminal differentiation, the promoter region of this gene was isolated from human genomic DNA and characterized. A 2.2 Kbp genomic fragment upstream of the human mda-7 cDNA was isolated from a human placental genomic library (Stratagene) using a PCR-based method, cloned into pBluescript and the DNA sequence was determined. The full-length presumptive mda-7 promoter nucleotide sequence was searched using the GCG FINDPATTERN program to determine putative transcription factor (TF) binding sites. The transcription start site was determined by primer extension and mapped to a position 274 bp upstream from the open reading frame of the human mda-7 cDNA. The GCG promoter search results reveal a putative TATA homology element located between positions −25 to −31 and the area flanking this region is GC rich as is the case for TATA box domains. Some of the transcription factor binding sites that may be relevant to mda-7 gene expression are, AP1 and AP2 (PKC activated TF) and C/EBP (growth arrest and terminal differentiation associated TF). Several additional transcription factor binding sites, such as SP1, CREB, CBP, Elk1 and p53, are also identified by the above-described analysis.

Figure 1B:
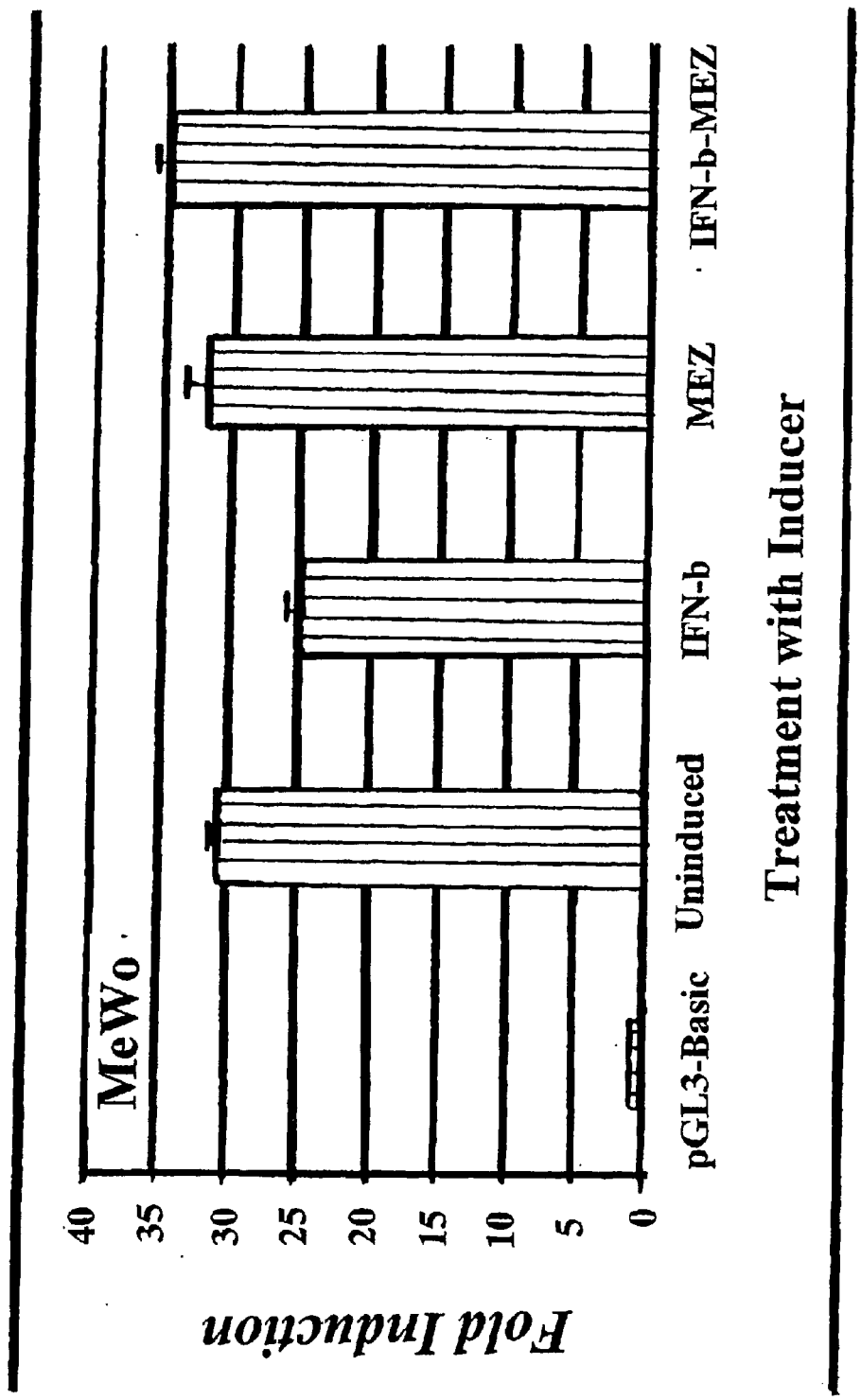

The presumptive promoter fragment was assayed for promoter activity using a heterologous gene reporter system (pGL3-Basic, luciferase assay system, Promega). The full-length promoter-luciferase construct (FL-mda-7 promoter) was transiently transfected into HO-1 and MeWo human melanoma cells using Superfect$^R$ reagent (Qiagen) and untreated or treated with IFN-β, MEZ or a combination of IFN-β+MEZ, and assayed for luciferase expression 48 h later (Promega Luc$^+$ assay kit). The transfection efficiency was determined by cotransfection with RSV-β-galactosidase (Tropics β-Gal assay kit) and the relative luciferase activity was computed after correction for variations in transfection efficiencies. As shown in FIGS. 1A–1B, the putative FL-mda-7 promoter construct displays high levels of basal activation in uninduced HO-1 and MeWo cells in comparison with the pGL3-Basic control plasmid. When treated with IFN-β for 48 hr the activity of the FL-mda-7 promoter decreases relative to uninduced HO-1 and MeWo cells (FIGS. 1A–1B). In several studies, treatment of HO-1 or MeWo with MEZ or IFN-β+MEZ for 48 hr results in only small changes in mda-7 promoter activity. Similar modest changes in mda-7 promoter activity were observed following differentiation inducer treatment in another human melanoma cell line 3S5, a derivative of the MeWo cell line (Ishikawa and Kerbel, 1989), stably expressing luciferase under the control of the FL-mda-7 promoter.

In summary, promoter assays indicate that modulation of mda-7 gene expression during differentiation in human melanoma cells may not be controlled at the level of transcription. Instead, they suggest an alternate mechanism for regulating mda-7 mRNA levels in terminally differentiated melanoma cells. One possible mechanism is posttranscriptional regulation of mRNA stability. Experiments described below were designed to determine if mRNA stability/instability contributes to the differential regulation of mda-7 gene expression during human melanoma terminal differentiation.

Mda-7 m/RNA is Unstable in Uninduced and Single Differentiation Inducer Treated Human Melanoma Cells and is Regulated by AU-rich Elements Present in the 3'-UTR Based on the Northern blotting results it appears that mda-7 mRNA is present during IFN-β+MEZ treatment and to a significantly lesser extent during treatment with only MEZ (Jiang et al., 1995a). However, the promoter is active in undifferentiated melanoma cultures and remains active during differentiation inducer treatment of human melanoma cells (FIGS. 1A–1B). To confirm that the mda-7 gene is transcriptionally active in uninduced and differentiation inducer treated HO-1 cells, nuclear run-on experiments were performed. Transcription of the housekeeping gene, GAPDH served as an internal control. The results shown in FIG. 2A indicate that, the polymerase densities and presumably, therefore, the rates of transcription are the same for uninduced control and MEZ and IFN-β+MEZ treated HO-1 cells. Only in the case of IFN-β alone does the rate of transcription appear to be reduced relative to the other three conditions. These results suggest that the decreased steady-state level of mda-7 mRNA in MEZ treated cells and the undetectable levels by Northern blotting in uninduced and IFN-β treated cells are most probably the result of posttranscriptional events that regulate message stability. To determine the possible presence of trace amounts of mda-7 mRNA in response to differentiation inducer treatment (IFN-β) and in the absence of treatment, a more sensitive method of message detection was employed, i.e., RT-PCR followed by Southern blotting. As shown in FIG. 2B, mda-7 mRNA (by RT-PCR) is present in uninduced, IFN-β and MEZ treated cells, albeit at lower levels, compared to IFN-β+MEZ treated samples.

Having demonstrated the presence of mda-7 mRNA in uninduced and IFN-β, MEZ and IFN-β+MEZ treated samples, experiments were performed to determine the mechanism regulating steady state mRNA levels. Analysis of the complete mda-7 cDNA sequence reveals the presence of AU-rich sequences in its 3'-UTR (FIG. 2C). Many transiently expressed genes, including lymphokine and other cytokine genes and the proto-oncogenes c-myc and c-fds, contain AU-rich sequences in their 3'-UTRs (Shaw and Kamen, 1986). Several studies demonstrate that the presence of AU-rich elements (ARE) in eukaryotic mRNAs correlate with rapid mRNA turnover and posttranslational control (Shaw and Kamen, 1986; Aharon and Schneider, 1993; Rajagopalan andmalter, 1997). The ARE consists of multiple AUUUA motifs or sequences resembling it. Comparison of mda-7 ARE with several cytokine and lymphokine mRNAs is shown in FIG. 2C. Mda-7 has three AUUUA elements and the area between these elements is also AU-rich.

To examine the posttranscriptional regulation of mda-7 mRNA specifically during terminal differentiation of human melanoma cells, we constructed a Luciferease-mda-7-ARE-3'UTR plasmid under transcriptional control of either the FL-mda-7 promoter (FIG. 3) or the SV40 large T-antigen promoter. These plasmids were co-transfected into HO-1 cells and treated with differentiation inducers. In uninduced cells the luciferase activity is minimal as is the case when HO-1 cells are treated with IFN-β or MEZ alone (FIG. 3A). In contrast, luciferase enzyme activity is increased in terminally differentiated (FNβ+MEZ treated) HO-1 cells (compare the results shown in FIG. 1A with FIG. 3A). Kinetic analyses of luciferase activity using this modified construct over a three-day period document a significant temporal increase in activity (FIG. 3B). Similar results were obtained with a plasmid construct containing an SV40 large T-antigen promoter instead of the mda-7 promoter plus the mda-7 ARE 3' UTR sequence. Based on these observations we conclude that the steady state level of mda-7 mRNA is determined by posttranslational decay of the message, which is apparent in uninduced and in HO-1 cells treated singularly with IFN-β or MEZ. However, in IFN-β+MEZ treated cells that are terminally differentiated, the mda-7 message does not undergo rapid degradation.

Figure 4A:
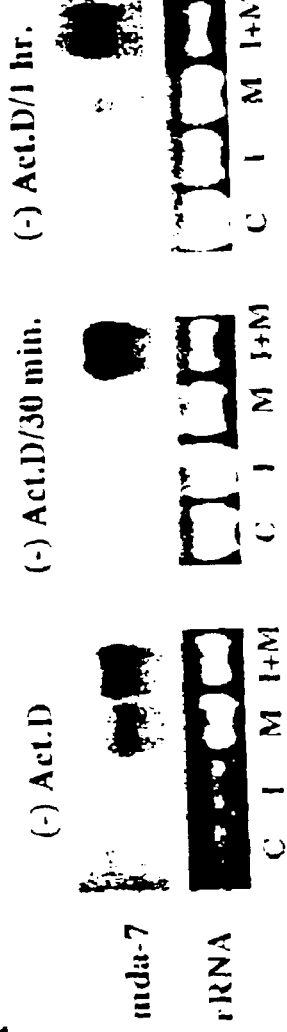
FIGS. 4A–4B. Effect of actinomycin D and cycloheximide on th half-life and stability of the mda-7 message.

To demonstrate enhanced message stability of mda-7 specifically in terminally differentiated cells, the rate of mRNA decay was determined. HO-1 cells were treated with differentiation inducers followed by incubation with actinomycin D for 30 and 60 min. Northern blotting results reveal that the mda-7 message has a very short half-life, approximately 1 h in terminally differentiated HO1 cells (FIG. 4A). However, its half-life is significantly less in control, IFN-β and MEZ alone treatment conditions (less than 15 min). The lability of such messages which decay with a half-life of approximately 30 to 60 minutes distinguishes them from most mammalian messages, which typically are more stable, with half-life's ranging from hours to days (Krowczynska et al., 1985). These results suggest that stable expression of mda-7 mRNA during HO-1 terminal differentiation results from posttranscriptional enhancement of message stability.

Figure 4B:
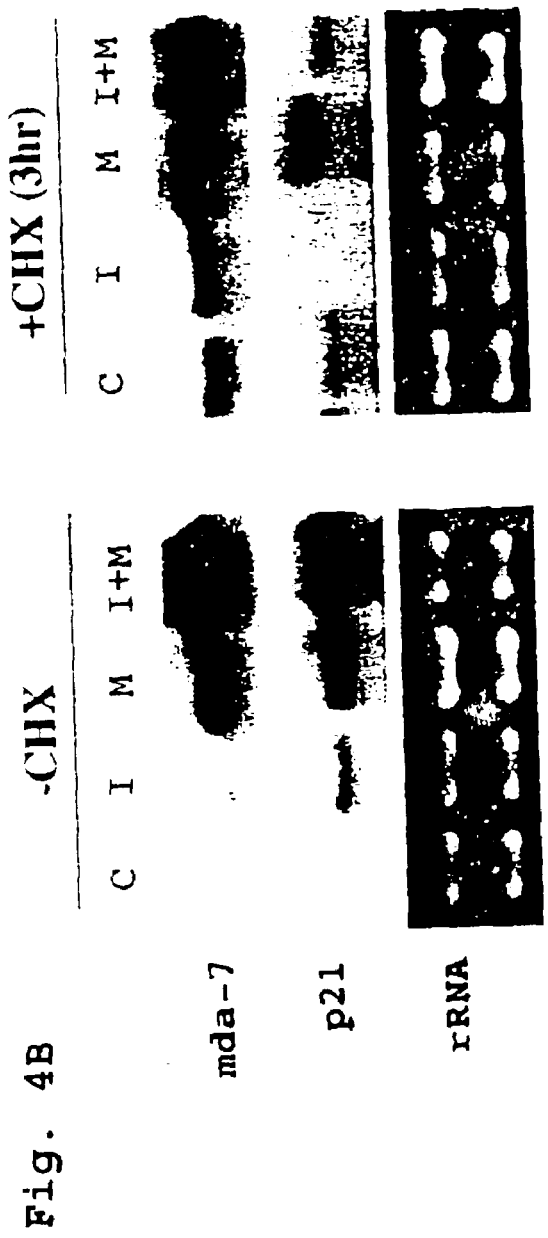

Several studies on intrinsically unstable mRNAs demonstrate that drugs, which inhibit protein synthesis, increase their stability (Raj and Pitha, 1981; Elder et al., 1984; Linial et al., 1985). The effect of protein synthesis inhibitors was tested using cycloheximide, a compound that inhibits peptide bond formation. The accumulation of mda-7 is visibly increased with cycloheximide treatment in MEZ treated samples and to a lesser extent in control and IFN-β treated samples (FIG. 4B). In contrast, the cyclin-dependent kinase inhibitor p21/Waf1/Cip1/mda-6, a gene that is upregulated during HO-1 terminal differentiation (Jiang and Fisher, 1993; Jiang et al., 1994, 1995b) does not show message accumulation in the presence of cycloheximide. Based on these observations we conclude that inhibition of protein synthesis enhances the stability of mda-7 mRNA, and this effect may be a consequence of inhibition of the de novo synthesis of specific labile factor(s) that target the ARE sequences in the mda-7 3'-UTR for rapid mRNA degradation.

Treatment of human melanoma cells with IFN-β+MEZ results in irreversible growth suppression and terminal differentiation (Fisher et al., 1985; Jiang and Fisher, 1993; Jiang et al., 1993, 1994). These processes correlate with profound changes in cellular physiology, including morphological alterations with the development of dendrite-like processes, enhanced melanin synthesis, modulation of the antigenic phenotype and a loss of tumorigenic potential in athymic nude mice. In addition, gene expression programs are dramatically altered during growth suppression and terminal differentiation, including the modified expression of genes regulating cell cycle progression, transcriptional control, cytoskeletal architecture and novel genetic elements with undefined functions (Jiang and Fisher, 1993; Jiang et al., 1993, 1994, 1995a, b, 1996; Kang et al., 1998b; Huang et al., 1999a, b). A potentially relevant gene whose expression corresponds with induction of irreversible growth arrest and terminal differentiation in human melanoma cells is the novel gene mda-7 (Jiang et al., 1994, 1995a). During melanoma progression, mda-7 levels are elevated in normal melanocytes, nevi and radial growth phase primary melanomas, whereas expression of this gene is reduced or undetected in late vertical growth phase primary melanomas and metastatic melanomas (Jiang et al., 1995a). The ability of IFN-β+MEZ to induce a reversion in gene expression to a more normal melanocytic state and induce terminal differentiation in human melanoma cells that coincides with renewed expression of mda-7 provides support for the "differentiation therapy" hypothesis. In this context, understanding the role of mda-7 in the differentiation process should provide relevant insights into growth control and terminal differentiation in human melanoma cells.

Although mda-7 is not detected by Northern blotting in proliferating HO-1 cells, treatment with IFN-β+MEZ for 24 h results in induction of this gene (Jiang et al., 1994, 1995a). To define the mechanism underlying mda-7 induction and maintenance during differentiation in human melanoma cells we have isolated the promoter region of this gene and determined the relationship between transcriptional and posttranscriptional processes in controlling mda-7 gene expression in human melanoma cells. These studies emphasize that a major component of mda-7 gene expression during terminal differentiation involves alterations in the stability of mda-7 mRNA. In uninduced and reversible differentiation induced (IFN-β or MEZ treatment) HO-1 cells the mda-7 message is produced (as indicated by RT-PCR) but it is unstable, whereas in terminally differentiated (IFN-β+MEZ) treated HO-1 cells mda-7 mRNA is stabilized resulting in production of MDA-7 protein.

In the present study we document that mda-7 gene expression is regulated posttranscriptionally, i.e., by altering message stability. Domain swapping mRNA stability analyses using the luciferase gene reporter system and the mda-7 mRNA destabilization domain (3'-UTR-AUUUA) relative to the SV40 polyadenylation signal sequence were performed. These studies document that the AU-rich a sequences in the 3'-UTR of mda-7 function at the posttranscriptional level and specifically decrease the accumulation of the mda-7 transcript. This effect is caused by a marked reduction in reporter gene (luciferase) activity, and hence mRNA stability. Posttranscriptional regulation is particularly important for short-lived proteins such as cytokines and regulators of cell proliferation. The sequences responsible for the posttranscriptional regulation of mRNAs are often found within the 3'-UTR of the transcript. It has been documented that deletion and point mutation alterations of the ARE consensus results in altered mRNA stability (Shaw and Kamen, 1986). The mRNAs of transiently expressed genes frequently contain an AU-rich sequence in the 3' untranslated region. The synthetic introduction of G's and C's in the AU-rich sequence of the human GM-CSF 3' UTR results in a significant alteration in the level of mRNA accumulation (Shaw and Kamen, 1986). The mRNA level for the wild-type AU-rich sequence is drastically reduced (to less than 3%) in comparison to the mutant GC-rich sequence (Shaw and Kamen, 1986). Measurement of the half-lives of the AU-rich versus the GC-rich sequence revealed that the AU-rich mRNA decays with a half-life of less that 30 min to a nearly undetectable level by 1 hr, whereas the GC-rich sequence remained stable for over 2 hr (Shaw and Kamen, 1986). Uridine pulse-chase experiments indicate that the AU-mRNA decays at a more rapid rate (t½ less than or equal to 30 min) than the stable GC-mRNA (Shaw and Kamen, 1986). These observations suggest that the presence of the AU sequence in the 3' UTR specifically confer instability to mRNAs. The magnitude of this effect is sufficient to explain the lack of accumulation of the mda-7 gene in proliferating cells and those treated singularly with IFN-β and MEZ.

A recent report (Spicher et al., 1998) documents the existence of at least ten different highly conserved regions (HCRs) within the 3'-UTRs that are capable of altering gene expression at the posttranscriptional level. The presence of multiple repeats of one such mRNA destabilization motif in the 3'-UTR of the mda-7 message lends itself to further regulation of its gene expression. It is unclear at this time if the increase in mda-7 mRNA is the result of selective stabilization during melanoma terminal differentiation or differential destabilization during proliferation. The field of mRNA stability is expanding at an accelerated rate with numerous reports of proteins implicated in the ARE mediated mRNA decay process. One such protein is the HuR protein that selectively binds ARE sequences in vitro and causes their selective destabilization (Myer et al., 1997). One theme that is common among all of these reports is that addition of protein synthesis inhibitors alleviates message instability, and mda-7 mRNA is no exception to this rule. Cycloheximide addition reverses the instability of the mda-7 message in control and MEZ alone treated cells. This finding demonstrates the requirement for protein translation for the destabilization event and implicates a labile factor(s) in this process.

In summary, mda-7 gene expression in human melanoma cells is regulated posttranscriptionally by regulation of its message stability by unknown mRNA degradation factor(s) during terminal differentiation in melanoma cells. In this respect, the alterations observed in mda-7 gene expression with melanoma disease progression provide support for the aberrant differentiation/gene expression model of melanoma development (Jiang et al., 1994) and provide a scientific basis for the successful application of 'differentiation therapy' (IFN-β+MEZ) in this cancer model system. The evolution and progression of cancer cells from normal cells may be a direct consequence of changes in transcriptional and/or posttranscriptional events resulting in a loss or decrease in the amount of gene products that control normal cell growth and differentiation. In this context, mda-7 may represent an important gene product that functions as a negative regulator of human melanoma progression.

Example 2

AP-1 and C/EBP Transcription Factors Contribute to Mda-7 Gene Promoter Activity During Human Melanoma Differentiation Treatment of human melanoma cells with a combination of recombinant fibroblast interferon (IFN-β) and the protein kinase C (PKC) activator mezerein (MEZ) causes a rapid and irreversible suppression in growth and terminal cell differentiation. Temporal subtraction hybridization combined with random clone selection, reverse Northern hybridization, high throughput microchip cDNA array screening and serial cDNA library arrays are permitting the identification and cloning of genes that are differentially expressed during proliferative arrest and terminal differentiation in human melanoma cells. A specific melanoma differentiation associated (mda) gene; mda-7, exhibits reduced expression as a function of melanoma progression from melanocyte to metastatic melanoma. In contrast, treatment of metastatic melanoma cells with IFN-β+MEZ results in expression of mda-7 mRNA and protein. To evaluate the mechanism underlying the differential expression of mda-7 as a function of melanoma progression and induction of growth arrest and differentiation in human melanoma cells the promoter region of this gene has been isolated from a human placental genomic library and characterized. Sequence analysis by GCG identifies multiple recognition sites for the AP-1 and C/EBP transcription factors. Employing a heterologous mda-7 luciferase gene reporter system we demonstrate that ectopic expression of either AP-1/cJun or C/EBP can significantly enhance expression of the mda-7 promoter in melanoma cells. In contrast, a dominant negative mutant of cJun, TAM67, is devoid of promoter enhancing ability. Western blot analyses reveals that cJun and the C/EBP family member C/EBP-β are physiologically relevant transcription factors whose expression corresponds with mda-7 mRNA expression. Electrophoretic mobility shift assays (EMSA) performed using nuclear protein extracts from terminally differentiated human melanoma cells document binding to regions of the mda-7 promoter that correspond to consensus binding sites for AP-1 and C/EBP. These results provide further mechanistic insights into the regulation of the mda-7 gene during induction of terminal cell differentiation in human melanoma cells. Defining the explicit molecular events underlying melanoma development and progression represent areas of intensive investigation (1–4). A precise understanding of this disease process offers promise for providing novel opportunities for therapeutic intervention (5). One view of melanoma development proposes a progressive series of alterations in which a melanocyte develops into a nevus, a dysplastic nevus, a primary melanoma (radial growth phase followed by early and late vertical growth phase) and finally a metastatic melanoma (1, 2, 6, 7). Although highly effective treatments, primarily surgery, are available if the cancer is identified early, even in melanoma patients with vertical growth phase lesions ≦0.76 mm thick, current treatment modalities are often ineffectual (<20% survival) in altering the prognosis of late stage metastatic disease (3, 4, 6, 7). These statistics emphasize the need for improved approaches for the therapy of this prevalent and often fatal cancer.

A hallmark of many cancers, including melanoma, is their inability to undergo normal programs of differentiation (8–11). A therapeutic approach to cancer therapy that is receiving a high level of interest, 'differentiation therapy', involves the use of single or multiple agents that can reprogram cancer cells to revert to a more differentiated state and lose their tumorigenic potential (5, 8–11)., The underlying premise of 'differentiation therapy' is that cancer cells do not contain or synthesize sub-threshold levels of gene products that are necessary for insuring normal growth and differentiation. Threshold levels of growth and differentiation modulating gene products are produced upon appropriate treatment resulting in a reversion of phenotype in the cancer cell to a more normal state. Support for this hypothesis comes from studies employing human melanoma cells as an experimental model (5, 9, 12). Treatment of metastatic human melanoma cells with IFN-B+MEZ results in an irreversible loss in proliferative and tumorigenic potential and a concurrent induction of terminal differentiation (5, 9, 12, 13). These cellular changes result in profound alterations in gene expression, including the induction, enhanced expression or suppressed expression of both novel and known genes (5, 14–17).

Using subtraction hybridization, a novel cDNA, mda-7, has been isolated as a gene responsive to differentiation therapy in human melanoma cells (5, 14, 18). Expression of mda-7 is low or absent in metastatic melanoma cells and treatment with IFN-B+MEZ results in an irreversible loss in growth capacity that correlates with a rapid and sustained induction of mda-7 (18). When transfected into human melanoma cells, mda-7 suppresses growth without inducing terminal cell differentiation (18). This growth inhibitory effect is not restricted to human melanoma cells, since ectopic expression of mda-7 causes growth suppression in diverse human cancers, including glioblastoma multiforme, osteosarcoma and carcinomas of the breast, cervix, colon, nasopharynx and prostate (19). Moreover, forced expression of mda-7 in human cancers, by means of a recombinant adenovirus (Ad.mda-7 S), results in a reduction in colony forming ability and in many cases induces programmed cell death (apoptosis) (20, 21). In contrast, infection of normal epithelial or fibroblast cells with Ad.mda-7 S does not elicit significant growth suppression or overt deleterious biological effects (20, 21). In these contexts, mda-7 represents an important gene with potential utility in cancer therapy (19–21). Defining the mechanism of action and mode of regulation of mda-7 will contribute to the successful use of this gene for translational applications.

To understand the transcription regulatory factor(s) contributing to mda-7 gene expression, we have cloned and begun to characterize the promoter of this gene. The mda-7 promoter is responsive to agents inducing terminal differentiation in human melanoma cells and the kinetics of promoter activation corresponds with the temporal expression of its mRNA (22). Transfection studies using a full-length mda-7 promoter luciferase construct (FL-mda-7-Prom) and various promoter deletion mutants demonstrate a requirement for two AP1 sites and three C/EBP sites upstream of the TATA box for maximum mda-7 promoter activity in melanoma cells. Additional experiments, including Western blotting, transfection with various expression vectors and EMSA implicate the PKC activated transcription factor AP-1 and the growth arrest and terminal differentiation specific transcription factor C/EBP in the regulation of mda-7 promoter activity.

Materials and Methods

Cell culture and induction of terminal cell differentiation. HO-1 is a melanotic melanoma cell line established from a metastatic inguinal lymph node lesion from a 49 year-old female and was used between passage 135 and 175 (9). The cells were maintained in Dulbecco's Modified Eagle's medium (DMEM) (Life Technologies, Inc.) supplemented with 10% fetal bovine serum (Hyclone), 100 units/ml penicillin and 100 µg/ml streptomycin at 37° C. in a 95% air 5% $CO_2$ humidified incubator. Terminal differentiation was induced in HO-1 cells by treatment with IFN-β (2000 units/ml) plus MEZ (10 ng/ml) for a period of 24 h or as indicated in the figure legends.

Isolation and cloning of the mda-7 promoter. A human placental genomic 1 library (Stratagene) was screened using the mda-7 cDNA (18) labeled by random priming (Life Technologies, Inc.) using $\alpha$-$^{32}$P[dCTP]. Three 1 phage clones were identified and isolated to homogeneity. An anti-sense primer, 5'-CGTCCCAGCCGTGGAAGTCAT-3' (SEQ ID NO:2) corresponding to the region 40–50 bp from the 5' terminal end of the mda-7 cDNA was used with the T3 or T7 primer in a polymerase chain reaction to amplify the region upstream of the mda-7 cDNA from the three 1 phage clones. The proof reading polymerase, Tth polymerase (Clonetech) was employed for this purpose. One of the 1 phage clones yielded a 2.2 Kbp amplification product that was cloned into pBluescript and sequenced (ABI sequencing).

H terologous promoter construction, and transient transfection and promoter assays. A set of reporter gene constructs was prepared using the luciferase vector pGL3-Basic (Promega Corp.). The full-length mda-7 promoter fragment was cloned into the pGL3-Basic (Promega) vector containing the luciferase reporter gene. Promoter deletions from the 5' end were produced using internal restriction sites (ApaI, NdeI and NheI) and the fragments were cloned into the pGL3-Basic vector. The various promoter-containing plasmids were transiently transfected into HO-1 cells using Superfect$^R$ (Qiagen) according to the manufacturer's protocol. The cells were treated with differentiation inducers for 24–48 h following transfection and assayed for luciferase activity using the Luc$^+$ Assay kit (Promega). The SV40-β-Galactosidase plasmid was co-transfected with the luciferase constructs and used to normalize for variations in transfection efficiencies between experiments. All experimental points were performed in triplicate and individual experiments were repeated a minimum of two times. Transcription factor expression plasmids, cJun, C/EBP-α and C/EBP-β, were regulated by the CMV promoter.

Indirect immunofluorescence analysis. Cells were grown on sterile cover slips, washed 2× in PBS (phosphate buffered saline, pH 7.5) and fixed in cold methanol for 5 min at −20° C. (23). The fixed cells were air dried for 30 minutes and permeabilized in PBS+0.5% Triton X-100 for 30 min at RT. Primary anti-MDA-7 monoclonal antibody was incubated with the coverslips at 37° C. for 1 h in a humid chamber followed by washing in PBS. Commercially prepared secondary anti-mouse antibody conjugated with Rhodamine (Pierce) was used to detect MDA-7 localization. The cells were washed in PBS and counter stained with the DNA dye 4'6-diamidino-2-phenylindone (DAPI) at a concentration of 2 mg/ml. The coverslips were sealed using nail polish. Microscopic analysis was performed using an Olympus fluorescence microscope.

Electrophoresis and immunoblotting. Equal amounts of whole cell proteins were analyzed by sodium dodecylsulfate-polyacrylamide gel electrophoresis (SDS-PAGE, 4–20% gradient gel; Novex) and electrotransferred onto ECL grade nitrocellulose (Amersham) as described previously (24). Commercial antibodies against cJun/AP-1 (1:1000), C/EBP-α (1:500) and C/EBP-β (1:500) (Santa Cruz Biotechnology) were used. Immunoreactive bands were visualized by HRP-conjugated secondary antibodies (Pierce), using ECL detection reagents (Amersham) according to the manufacturer's protocols.

Electrophoretic Mobility Shift Assay (EMSA). Nuclear extracts were prepared as described (25). Briefly, binding reactions were performed in 10 or 20 ml reaction mixtures containing 1–3 mg of nuclear extracts from control or differentiation inducer treated HO-1 cells. The binding buffer contained 12 mM HEPES (pH 7.9), 5 MM $MgCl_2$, 60 mM KCl, 0.6 mM EDTA, 0.5 mM dithiothreitol, 1 mg of poly (dI-dC), 10% glycerol. The region corresponding to the putative AP-1 and C/EBP binding sites present between NdeI and NheI restriction enzyme sites was PCR amplified using flanking primers, 5'-AGGCTGGATTTG GCTTGTGAC-3' (Sense) (SEQ ID NO:3) and 5'-CTGTTTAATCCAGCACTTCCC-3' (Antisense) (SEQ ID NO:4). The PCR product was column purified (Qiagen), end labeled with $\gamma$-$^{32}$P [ATP] and 1500 cpm of double stranded DNA were used per binding reaction. Binding reactions were performed at RT for 30 min. Reactions were then loaded onto a 4% polyacrylamide gel and electrophoresed at 4° C. at 100 V in 0.25× Tris-borate-EDTA as described (26, 27). Competition and supershift reactions were identical to those described above, except a 10–100 fold excess of AP-1 or C/EBP wild type or mutant oligonucleotides (AP-1/WT; 5'-CGCTTGATGACTCAGCCGGAA-3'), (SEQ ID NO: 5), (C/EBP/WT; 5'-TGCAGATTGCGCAATCTGC A-3'), (SEQ ID NO. 6), (AP-1/MT; 5'-CGCTTGATGACTTGGCCGGAA-3') (SEQ ID NO:7) and C/EBP (C/EBP/MT; 5'-TGCAGAGACTAGTCTCTGCA-3') (SEQ ID NO:8) or 1–5 μg of either anti-cJun/AP-1 or anti-C/EBP-β antibody (Santa Cruz) were added to the binding reactions along with the labeled probe and reactions were incubated for 30 min at RT prior to electrophoresis. The gels were then dried and exposed to X-ray film.

Nucleic acid analysed. Total cytoplasmic RNA was prepared by the guanidinium-HCL extraction method followed by Northern blotting or RT-PCR analysis using previously published protocols (12, 18, 22). For Northern blots, 15 mg of RNA was denatured with glyoxal/DMSO, electrophoresed on 1% agarose gels, transferred to nylon membranes and hybridized with $^{32}$P-dCTP labeled cDNA probes.

Results

Figure 5A:
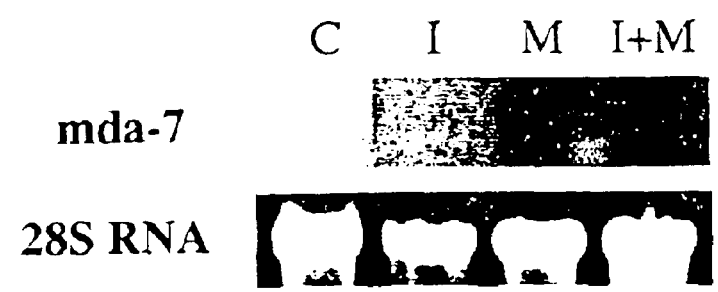
FIGS. 5A–5B. Message and protein expression analyses of mda-7 during melanoma terminal differentiation.

Message and protein expression of mda-7 correlates specifically with induction of terminal differentiation in human melanoma cells. Expression of mda-7 corresponds with induction of terminal differentiation in human melanoma cells (18). Northern blotting reveals a significant amount of stable mda-7 message when human melanoma cells (HO-1) are induced to terminally differentiate after a 24 h treatment with a combination of IFN-β plus the PKC activator MEZ (FIG. 5A). Quantitatively less mda-7 mRNA is also apparent in HO-1 cells treated only with MEZ for 24 h. However, unlike IFN-B+MEZ which induce irreversible growth arrest and terminal differentiation in HO-1 cells, MEZ induced growth suppression and differentiation are reversible (5, 9, 12). Removal of MEZ from HO-1 cells followed by replacement with fresh growth medium (DMEM, 5% FCS) results in a loss of differentiated properties and a return to control growth rates (5, 9, 12). In this reversible differentiation process, removal of MEZ results in abrogation of mda-7 expression.

This finding suggests that mda-7 gene expression is directly responsive to MEZ treatment and may be activated by a PKC-mediated pathway. The significant difference in the accumulation of mda-7 message following induction of terminal differentiation versus induction of reversible differentiation implicates posttranscriptional processes, such as mRNA processing and/or stabilization, in sustaining steady state mda-7 message levels in terminally differentiated HO-1 cells (22).

Figure 5B:
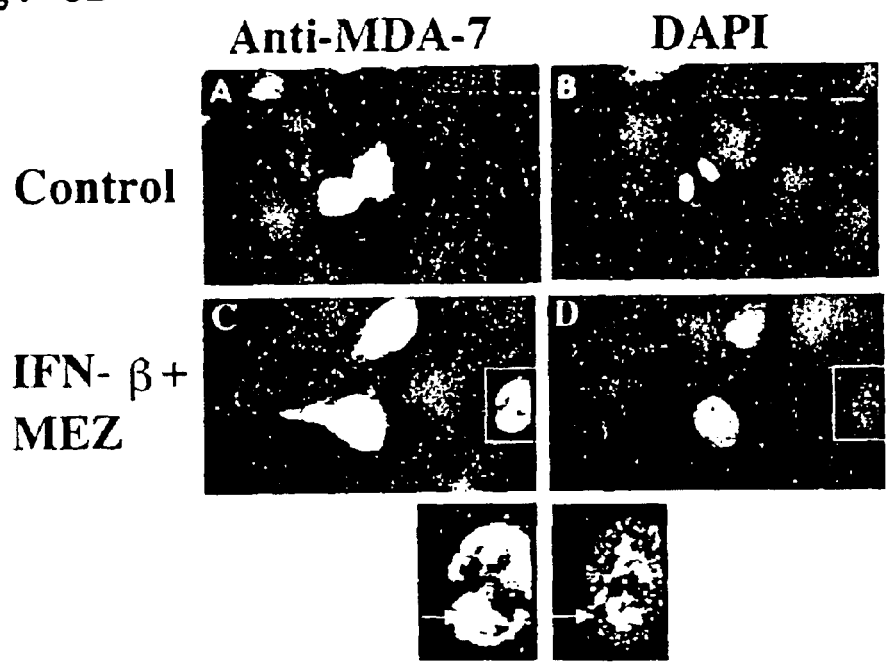

To demonstrate MDA-7 protein expression during melanoma terminal differentiation, indirect immunolocalization using monoclonal antiserum generated against a synthetic MDA-7, C-terminal peptide was employed. The immune serum was previously tested for MDA-7 specificity in immunoprecipitation experiments (18). An ⁻24 KDa protein that corresponds in size to the mature MDA-7 protein was precipitated in immune complexes from IFN-β+MEZ treated human melanoma cells. The immuno-staining pattern observed in undifferentiated (control, A and B) and terminally differentiated (IFN-β+MEZ, C and D) melanoma cells is shown in FIG. 5B. Localization of the anti-MDA-7 antibodies was detected using commercially available (Pierce) Rhodamine conjugated secondary antibodies (see, Materials and Methods). This analysis reveals that the MDA-7 protein (anti-MDA-7) is localized to the nucleus in terminally differentiated melanoma cells (FIG. 5B, panel C) and is not detectable in undifferentiated cells (FIG. 5B, panel A), except in those cells undergoing mitosis. The localization of MDA-7 within the nucleus of terminally differentiated cells appears to be in patches (see enlargement of single nucleus shown below), and this punctate pattern corresponds with dense chromatin regions revealed by the DAPI bright staining (FIG. 5B, panel D) and coincides with the MDA-7 staining pattern. The nuclear margin in terminally differentiated cells is also very brightly stained, and represents an area where the nuclear matrix interacts with the nuclear scaffold and other structural components of the nucleus, such as the nuclear lamins (28). Moreover, the region immediately surrounding the nucleus, on the cytoplasm side, is brightly stained with the anti-MDA-7 antiserum. These observations demonstrate that the MDA-7 protein is localized primarily in the nucleus and more so in condensed chromatin regions in terminally differentiated cells. Present results and earlier studies (18, 22) indicate that the message and protein expression pattern of mda-7 appears to be under tight control during terminal differentiation, with the exception of mitosis. Taken together these findings suggest that transcription activation of the mda-7 promoter may be evident during cellular mitosis and differentiation. Interestingly, the finding of low levels of mda-7 message in MEZ alone treated samples suggests that, its promoter may be transcriptionally responsive to PKC activators. However, message accumulation under MEZ alone treatment conditions is relatively low when compared to IFN-β+MEZ treatment, and is suggestive of secondary message regulation that may be posttranscriptional, such as, mRNA processing and message stabilization/destabilization observed for many cytokines, lymphokines and proto-oncogenes (22).

Cloning of the mda-7 promoter and induction by transcription factors. To define the mechanism of mda-7 gene regulation and to establish a role for PKC activation in transcription regulation of mda-7 gene expression during melanoma terminal differentiation, the promoter region of this gene was isolated from human genomic DNA and characterized. A 2.2 Kbp genomic fragment upstream of the human mda-7 cDNA was isolated from a human placental genomic library (Stratagene) using a PCR-based method, cloned into pBluescript and the DNA sequence was determined. The full-length presumptive mda-7 promoter (FL-mda-7-Prom) nucleotide sequence was searched using the GCG FINDPATTERN program to determine putative transcription factor (TF) binding sites (FIG. 6). The transcription start site was determined by primer extension and mapped to a position 274 bp upstream from the open reading frame of the human mda-7 cDNA (data not shown). The GCG promoter search results reveal a putative TATA homology element located between positions −25 to −31 and the area flanking this region is GC rich as is the case for TATA box domains. Some of the transcription factor binding sites indicated in FIG. 6 are relevant to mda-7 gene expression, such as AP-1 (PKC activated TF) and C/EBP (growth arrest and terminal differentiation associated TF).

Figure 7A:
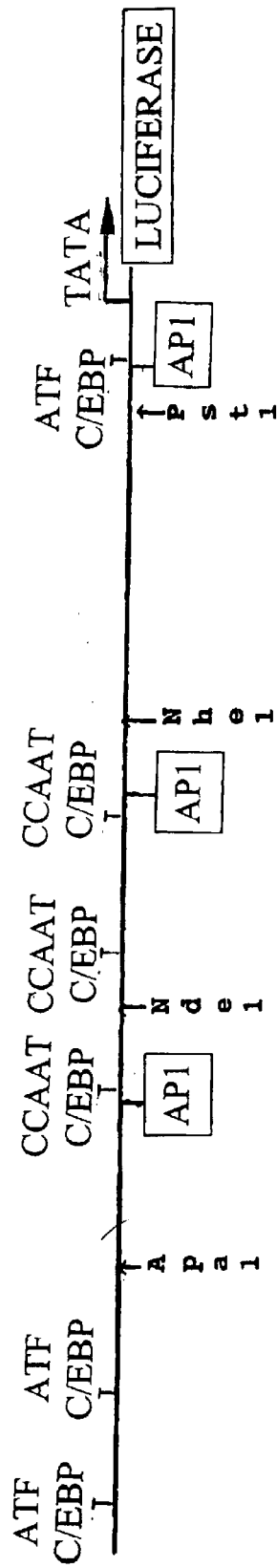
FIGS. 7A–7F. Schematic of the mda-7 promoter and various deletion constructs and promoter activation by differentiation transcription factors.
Figure 7B:
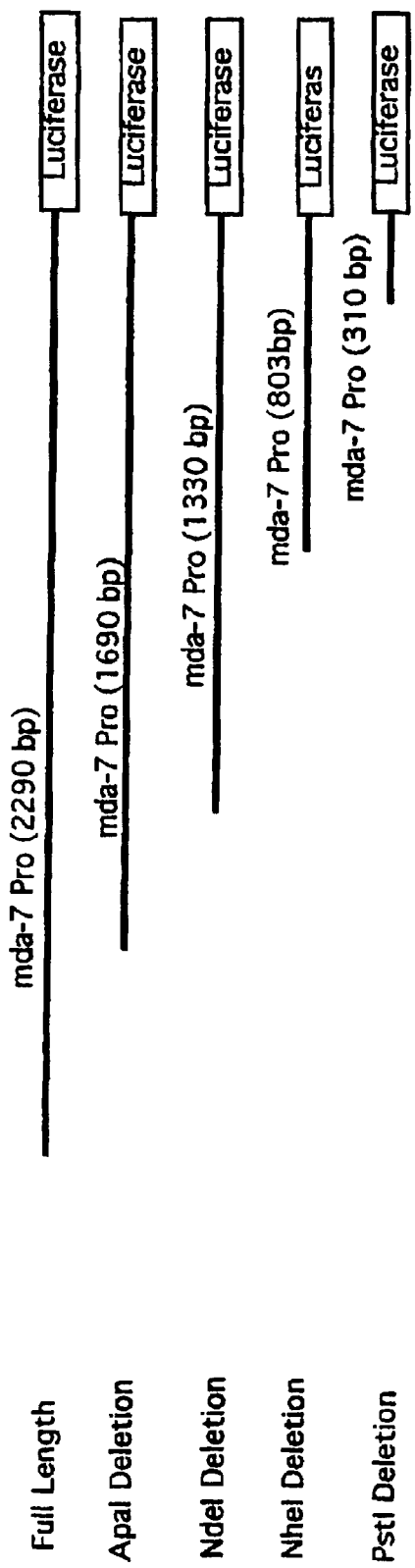
Figure 7C:
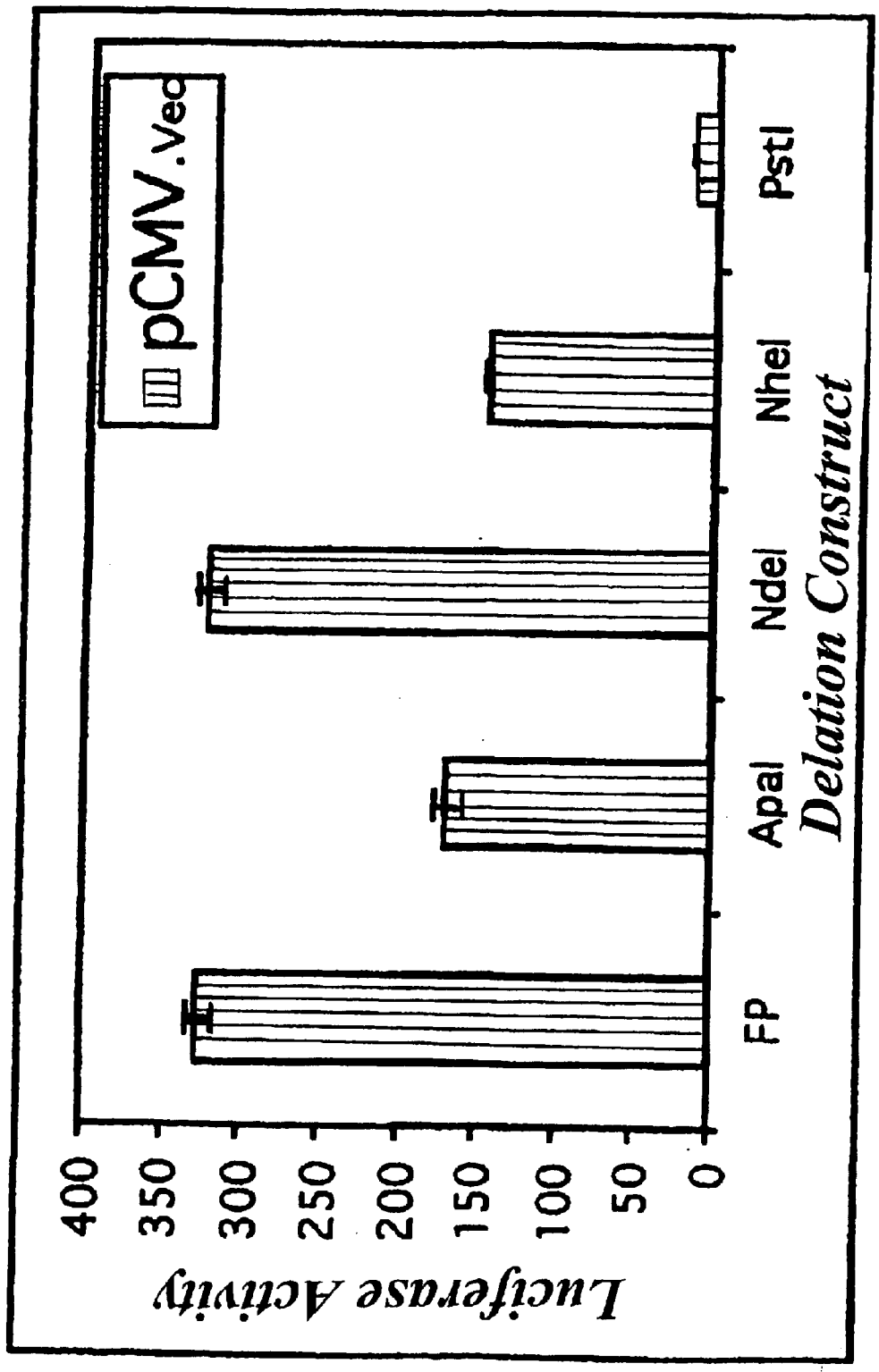
Figure 7D:
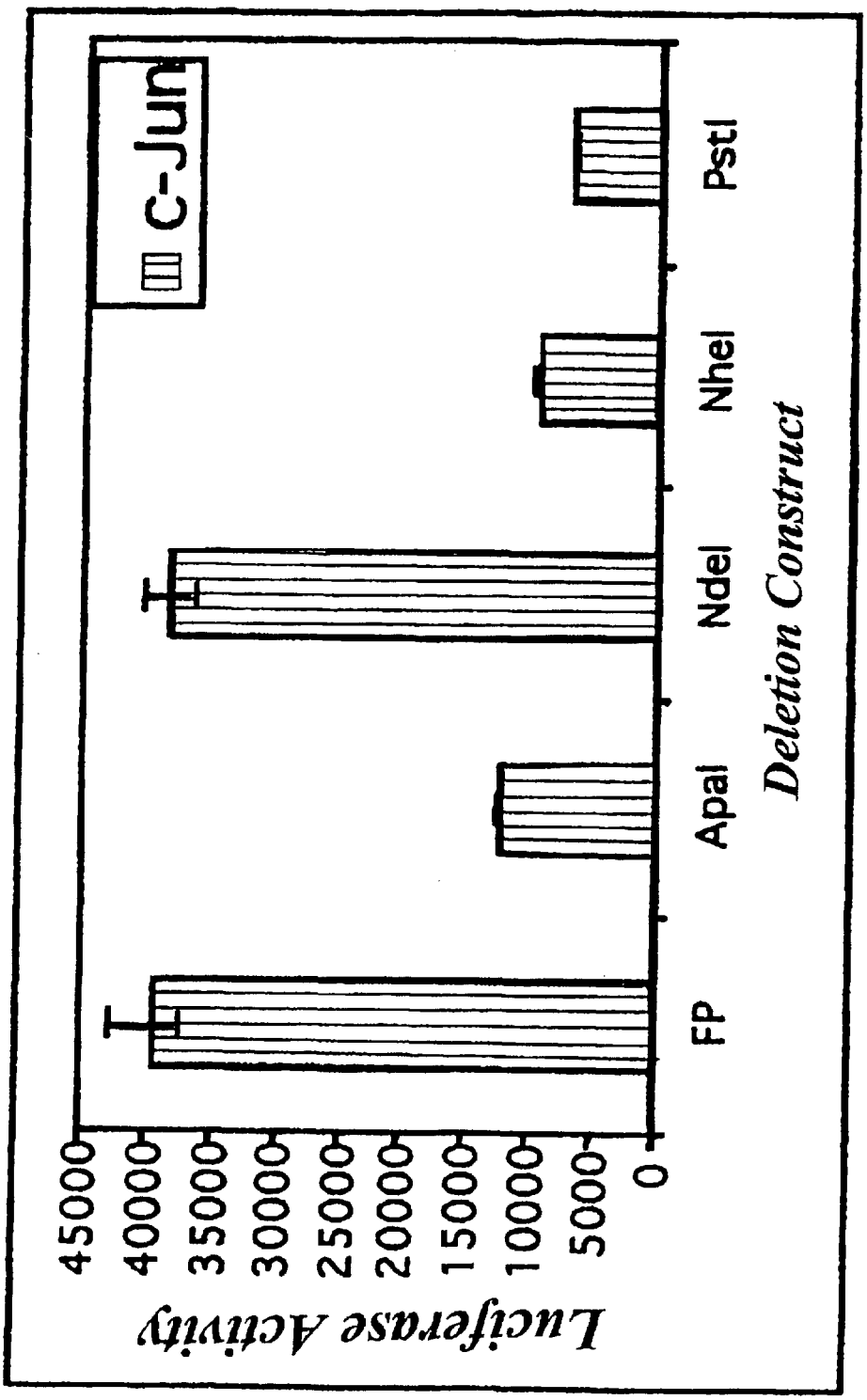
Figure 7E:
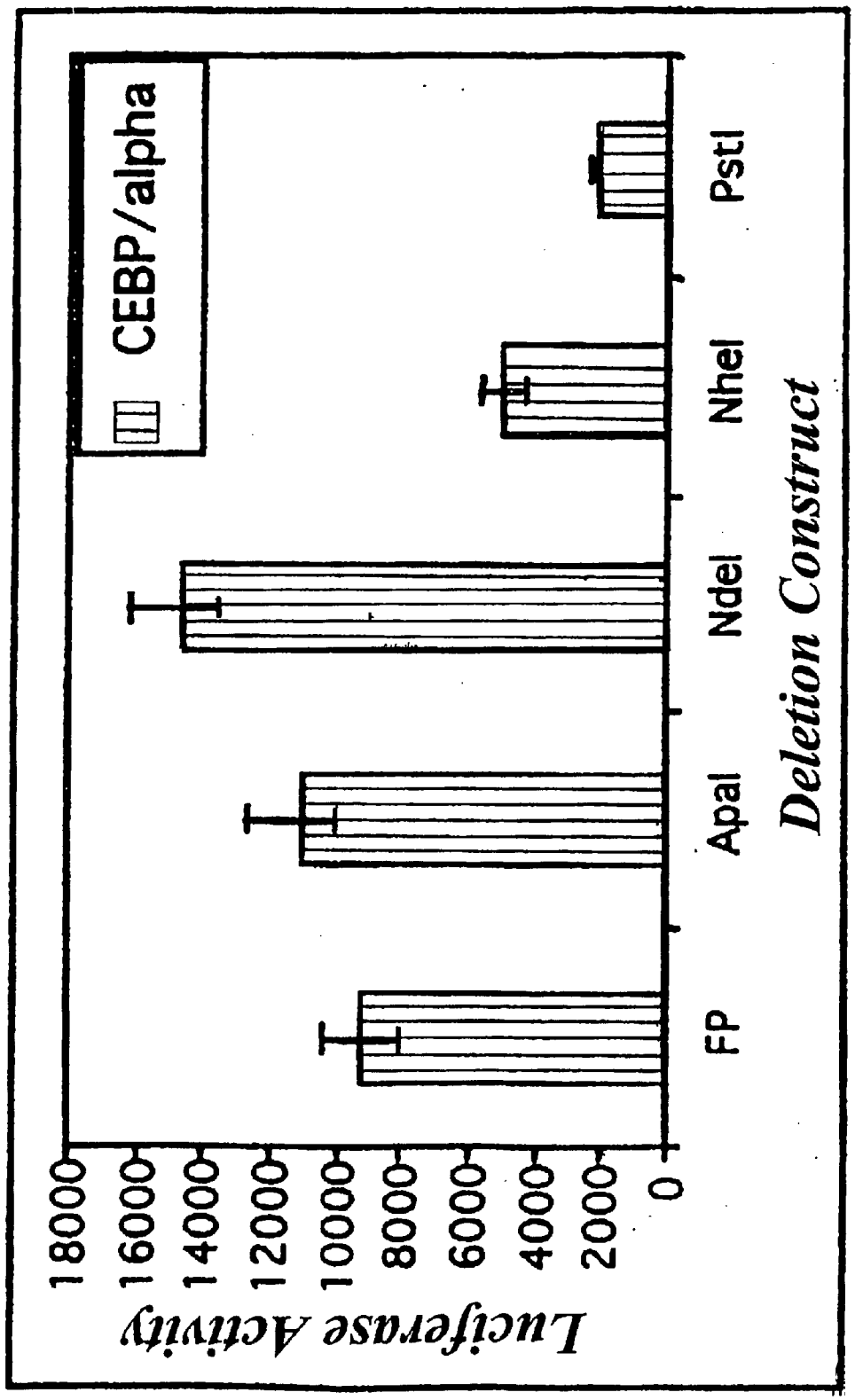
Figure 7F:
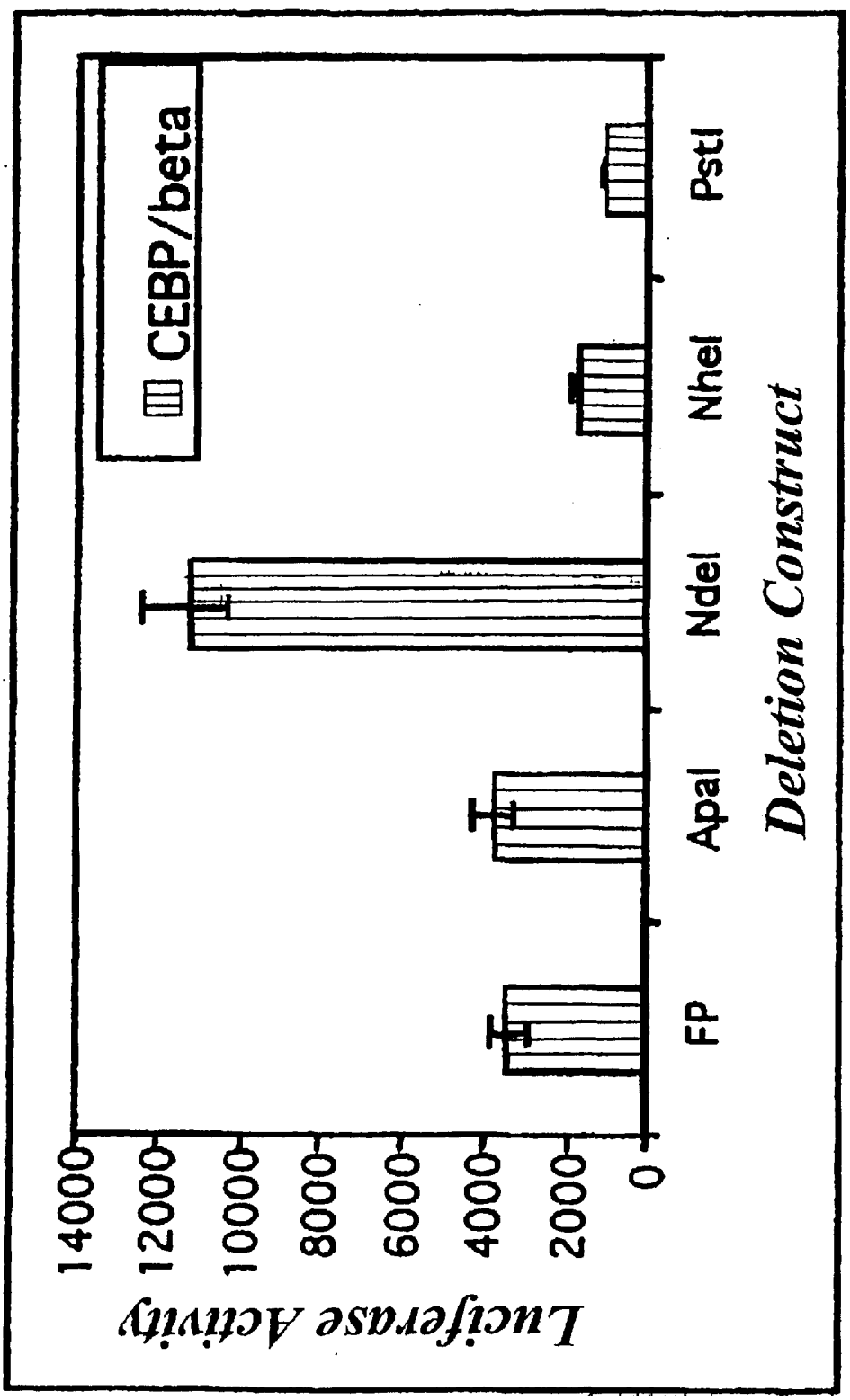

Transcription factor binding sites distant from the TATA box are responsible for transactivation of the mda-7 promoter during differentiation. To begin to delineate the regions within the mda-7 promoter responsible for transactivation, deletion fragment analyses were performed. Five prime deletions of the mda-7 promoter at various endogenous restriction enzyme sites (ApaI, NdeI, NheI and PstI) were generated and cloned into the pGL3-Basic luciferase vector (see cartoon, FIGS. 7A and 7B). The deletion constructs were verified for nucleotide sequence at the deletion junction by ABI sequencing. The various constructs were transfected into HO-1 cells along with plasmids expressing either cJun/AP-1, C/EBP-α, C/EBP-β or pCM-V.Vec (plasmid minus insert). Twenty-four h after transfection cellular lysates were analyzed for luciferase activity. The results are shown in FIG. 7 (expressed as relative units of luciferase activity). Co-transfection of individual transcription factors with the mda-7 promoter documents an enhancement in promoter activity. Of the various deletions analyzed, the NdeI deletion construct is responsive to each of the transcription factors, i.e., cJun/AP-1, C/EBP-α and C/EBP-β (FIGS. 7D, 7E and 7F, respectively). Moreover, all of the deletion constructs display a basal level of activity in HO-1 cells and this pattern is similar to that observed with the FL-mda-7-Prom following transfection with a cJun construct (compare FIGS. 7C and 7D). Deletion at the NheI site results in a significant reduction in basal promoter activity in control HO-1 cells and decreased activation following expression of the different transcription factors. These observations suggest that sites within this region of the mda-7 promoter (between NdeI and NheI) are major contributors to de novo promoter activity in HO-1 melanoma cells and they are responsive to activation by the transcription factors cJun/AP-1, C/EBP-α and C/EBP-β.

Figure 8A:
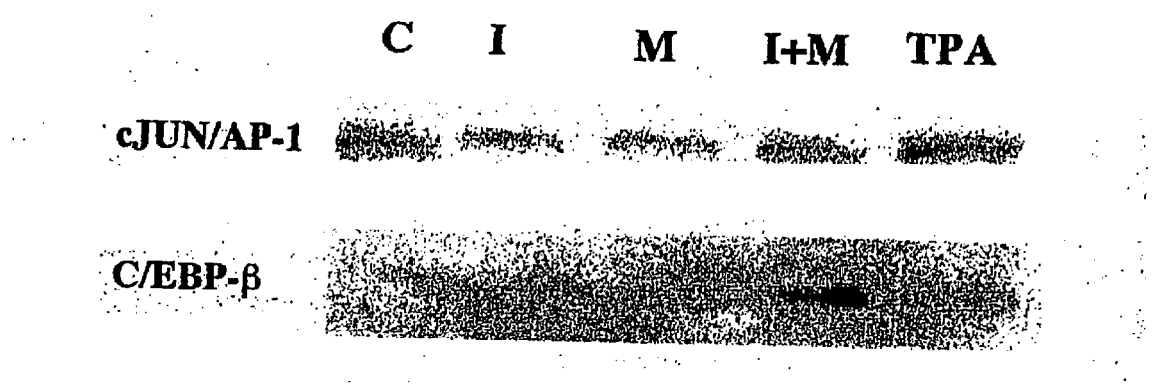

AP-1 and C/EBP families of transcription factors are responsible for mda-7 promoter activation during human melanoma differentiation. To ascertain the relevance and potential involvement of the AP-1 and C/EBP family of transcription factors during melanoma differentiation, Western blotting analyses were performed to determine the protein expression levels of cJun/AP-1 and C/EBP, and their temporal appearance during the process of human melanoma terminal differentiation. Western blot analyses of whole cell lysates (equal protein loading was verified by Coomassie blue staining of a parallel gel, data not shown) from uninduced HO1 cells and cultures treated for 24 h with IFN-β, MEZ, IFN-β+MEZ or TPA were analyzed using anti-cJun/AP-1, anti-C/EBP-α or anti-C/EBP-β antibodies. The results of these analyses are shown in FIG. 8A and reveal that both cJun/AP-1 and C/EBP-β/LAP proteins are highly expressed in terminally differentiated human melanoma cells. The expression of C/EBP-β/LAP protein is very specific to differentiation inducer treatment relative to cJun/AP-1, which is expressed in uninduced control HO-1 samples. In contrast, C/EBP-α was not detected in the lysates prepared from untreated or differentiation inducer treated HO-1 cells. As shown in FIG. 8A, cJun/AP-1 protein levels are relatively high in control HO-1 cells compared to C/EBP-β/LAP protein and the level of cJun/AP-1 is only marginally increased upon treatment with IFN-β+MEZ and TPA compared to uninduced controls. The high levels of C/EBP-β/LAP protein on the other hand in MEZ (approximately 3-fold) and IFN-β+MEZ (approximately 5- to 10-fold) treated HO-1 cells coincides, specifically with the drug induced expression of mda-7 message in differentiated cells (FIG. 5A). These findings indirectly implicate the C/EBP gene family members and specifically C/EBP-β/LAP in the transactivation of the mda-7 promoter during terminal differentiation of human melanoma cells. Based on these observations, further experiments were performed to establish direct binding of C/EBP-β and cJun within specific regions of the mda-7 promoter (see below).

The growth arrest and differentiation specific transcription factor, C/EBP, regulates mda-7 promoter activity. The CCAAT/enhancer-binding protein (C/EBP) family of transcription factors plays an important role in regulating the expression of various genes controlling growth and differentiation, and is considered to be a master regulator of adipocyte and liver development (29). C/EBP-like proteins are expressed in a cell type-restricted manner and also during terminal differentiation. The C/EBP family of transcription factors can bind to two types of sequences, (i) the motif that is present in viral enhancers, like the ATF site (adenovirus activation transcription factor), TGAAGTAA; and (ii) a large number of cellular promoters that contain the consensus sequence, CCAAT. Comparison of the nucleotide sequence for the C/EBP binding sites along the full-length mda-7 promoter reveal the presence of six putative C/EBP binding sites of which three sites resemble the ATF consensus motif, present in the adenovirus E4 promoter (TGAAGTAA; 30). The remaining three C/EBP sites display the CCAAT consensus sequence. Similar ATF and C/EBP sites are present in the rat somatostatin gene, adenoviral E3 promoter and fibronectin gene (31).

Figure 8B:
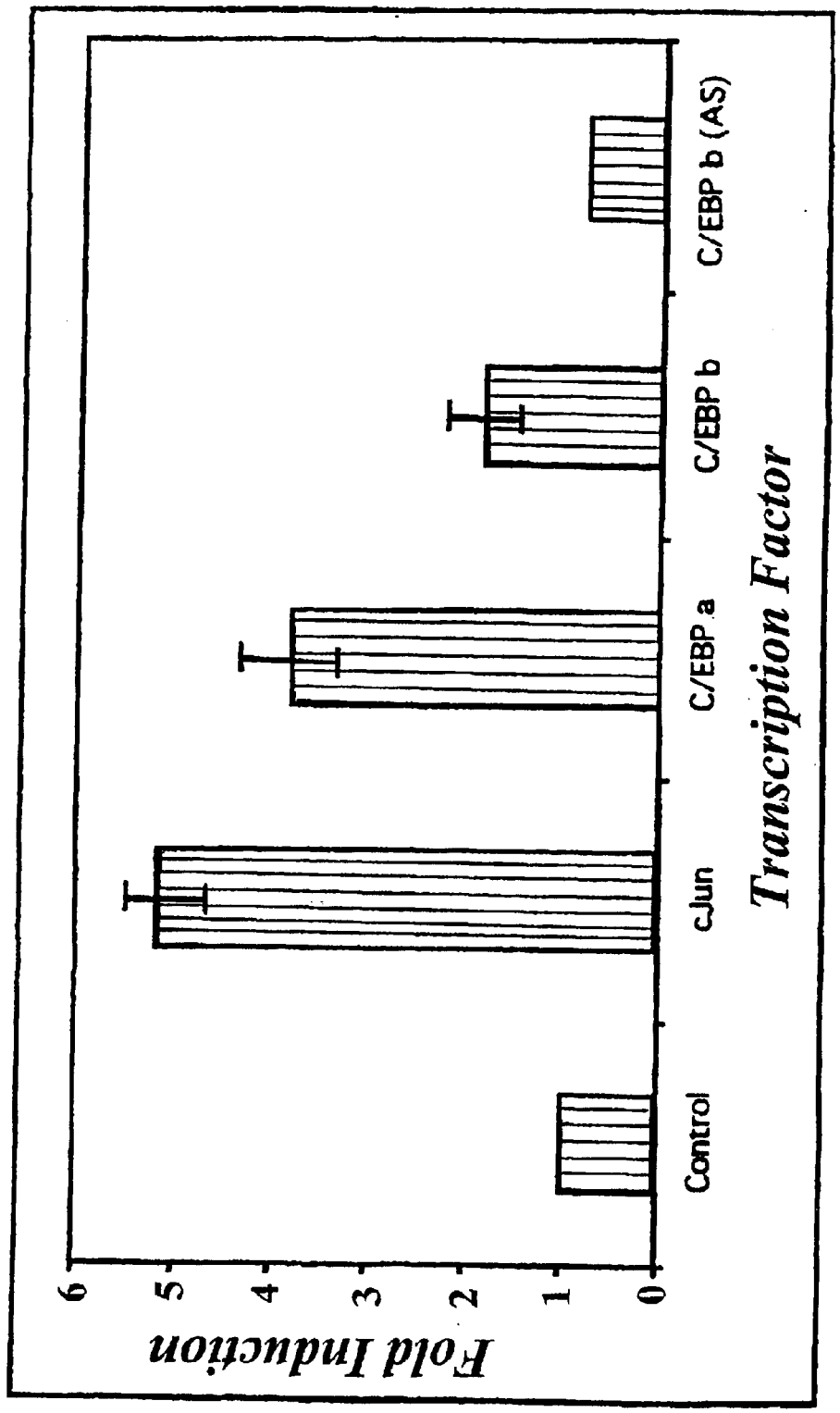

Since the mda-7 gene is highly expressed in terminally differentiated human melanoma cells, the influence of ectopic expression of two variants of C/EBP transcription factors, −α and −β (sense and antisense), on mda-7 promoter activation was evaluated. Experiments also determined the net contribution of each of the transcription factors on the mda-7 promoter in HO-1 cells. HO-1 cells were co-transfected with the FL-mda-7-Prom and a CMV driven C/EBP-α, C/EBP-β/LAP (S), C/EBP-B/LAP (AS), or cJun expression plasmid and assayed for luciferase activity 24 h later (FIG. 8B). These experiments indicate that of the three transcription factors, cJun (5.2-fold) mediated activation of the mda-7 promoter to be the greatest extent followed by C/EBP-α (3.8-fold) and C/EBP-β/LAP (1.8-fold). C/EBP-β/LAP (AS) had no effect on FL-mda-7-Prom activity. However, considering the protein expression results (FIG. 8A), it appears that cJun and C/EBP-β/LAP may be more physiologically relevant transcription factors responsible for mda-7 promoter activation during melanoma differentiation than C/EBP-a.

Figure 8C:
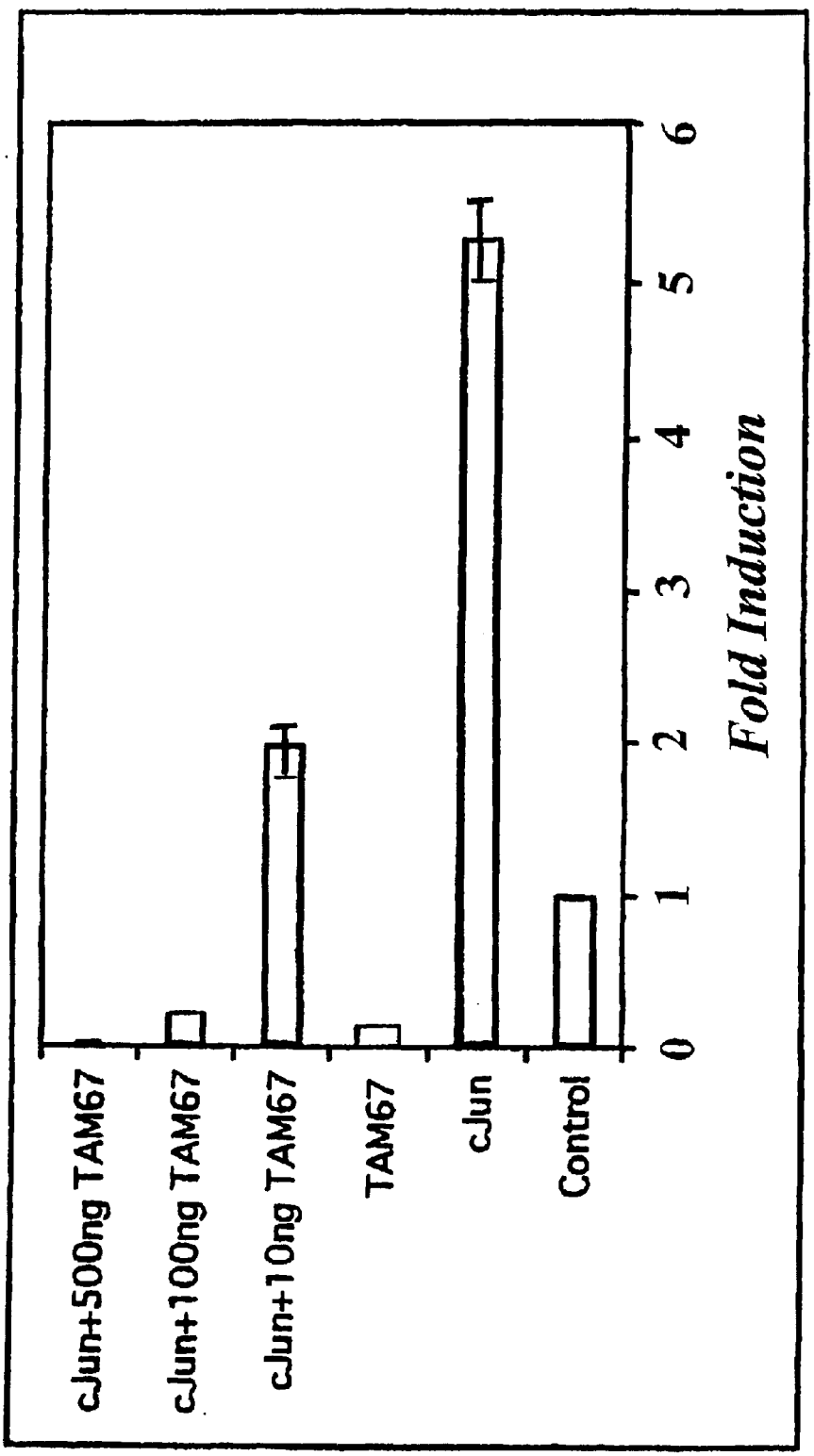
Figure 9A:
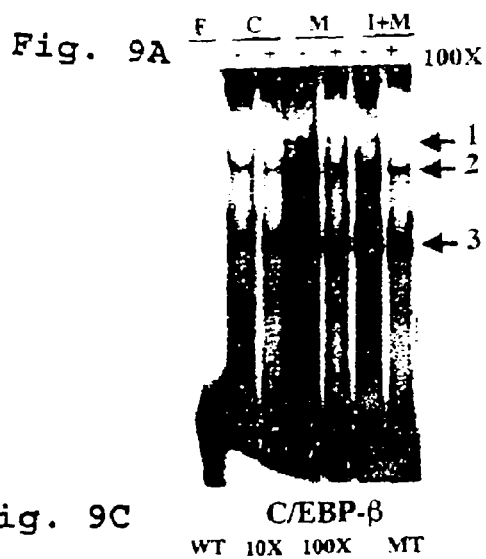
FIGS. 9A–9F. Electrophoretic mobility shift assay (EMSA) of a 350-bp DNA fragment generated by NdeI and NheI restriction enzyme digestion. The radiolabeled DNA fragment was incubated with whole cell lysates [FIG. 9A] or nuclear lysates [FIGS. 9B, 9C, 9D, 9E, 9F] from Control (C), MEZ (M), IFN-β+MEZ (I+M) or TPA treated HO-1 cells. –/+indicate the absence or addition, respectively, of a 100-fold excess of unlabeled competitor DNA [FIGS. 9A and 9B]. Arrows indicate the putative AP-1 (arrow 2) and C/EBP-β (arrow 1) DNA bound complexes.
Figure 9B:
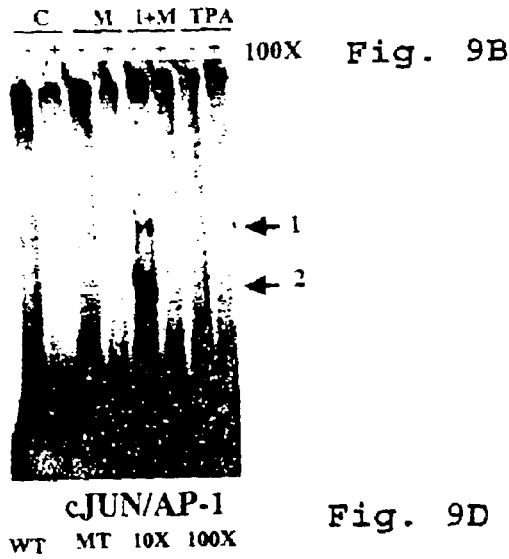
Figure 9C:
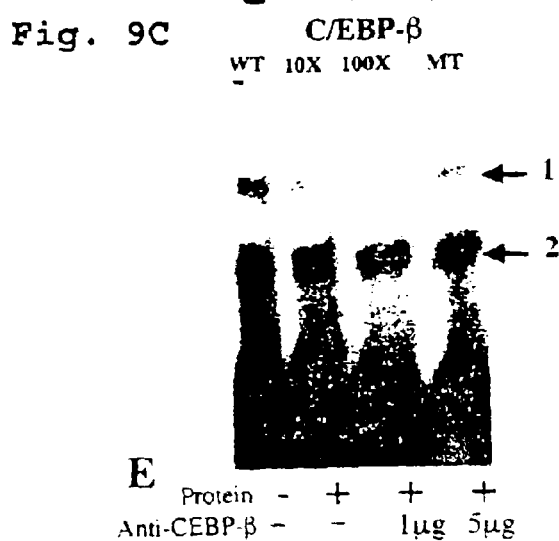

To establish further the specificity of cJun mediated activation of the mda-7 promoter a competition experiment was performed using different ratios of wild-type and mutant cJun plasmid, pCMV-TAM67 (provided by Dr. Michael J. Birrer, National Cancer Institute, MD). TAM67 is a deletion mutant of the cJun gene that lacks the NH2-terminal transactivation domain (amino acids 3–122). Expression of TAM67 has been shown to abolish cJun/AP-1 activity in a variety of cell types (32, 33). HO-1 cells were co-tansfected with either wild-type cJun, TAM67 or varying ratios of cJun:TAM67 in conjunction with the mda-7 promoter. The cells were assayed for luciferase reporter activity 48 h after transfection (FIG. 8C). These experiments indicate that wild-type cJun (5.25-fold) mediated activation was significantly higher than control (1-fold) FL-mda-7-Prom activity. As anticipated, introduction of the TAM67 mutant singly (0.12-fold) did not transactivate the mda-7 promoter because the transactivation domain is mutated in this gene. Since cJun forms homodimers (cJun:cJun) we determined the effect of addition of increasing amounts of TAM67 on wild-type cJun mediated induction of the mda-7 promoter (FIG. 8C). With increasing amounts of TAM67 (10, 100 and 500 ng) the ability of wild-type cJun to enhance FL-mda-7-Prom activity was compromised. This effect is due to the formation of cJun:TAM67 and TAM67:TAM67 dimers that are capable of binding the AP-1 consensus site without inducing transactivation, thereby resulting in reduced promoter induction with increasing levels of TAM67.

cJUN/AP-1 and C/RBP-β transcription factors bind to defined sites within the mda-7 promoter. Gel retardation assays (EMSA) were performed to determine if specific transcription factors bind to the mda-7 promoter during the process of terminal differentiation (FIGS. 9A–F). The region corresponding to the putative cJUN/AP-1 and C/EBP-β transcription factor binding sites, located between the NdeI and NheI promoter region (FIG. 7A), was amplified using PCR-based methods. High-speed supernatants were prepared from whole cell lysates of control or HO-1 cells treated with MEZ or IFN-β+MEZ. The supernatants were then incubated with $^{32}$[p]-labeled double stranded NdeI-NheI promoter region DNA and assayed by EMSA for the presence of DNA-protein complexes (FIG. 9A–9F). A distinct DNA-protein complex was apparent that was common to the different treatment conditions and was not competed by the addition of excess unlabelled primer (FIG. 9A, arrow 3). A second DNA-protein complex was also evident in control and following MEZ or IFN-B+MEZ treatment which displayed a small reduction following incubation with competitor DNA (FIG. 9A, arrow 2). In contrast, a DNA-protein complex was apparent that was specific to cellular lysates prepared from MEZ and IFN-β+MEZ treated cells (FIG. 9A, arrow 1). In order to establish nuclear protein-DNA interaction as well as specificity, nuclei from untreated control HO-1 cells as well as differentiation inducer treated HO-1 cells were isolated. Purity of nuclear preparations was determined by microscopic examination and purified nuclei were then used to prepare nuclear lysates. $^{32}$[p]-labeled double stranded DNA corresponding to the mda-7 promoter (NdeI-NheI region) was subjected to EMSA using these nuclear lysates. To verify specificity of DNA-protein interactions a 100-fold excess of unlabelled double stranded DNA was used in competition assays. The results of one such assay are shown in FIG. 9B. Interesting differences were observed between EMSA performed using whole cell lysates versus nuclear lysates. As seen in FIGS. 9A and 5B, only IFNβ+MEZ treated nuclear lysates contain two DNA-protein complexes (FIG. 9B, arrows indicate complex 1 and 2). In contrast to nuclear lysates, in whole cell lysates complex number 2 was present under all treatment conditions and was also present in untreated control HO-1 cells (FIG. 9A). These results suggest that there may be a high level of this DNA binding protein present in the cytoplasm of HO-1 cells. Addition of a 100-fold excess of unlabeled double stranded DNA eliminated both protein-DNA complexes in IFN-B+MEZ nuclear lysates (FIG. 9B, compare I+M−/+).

Figure 9D:
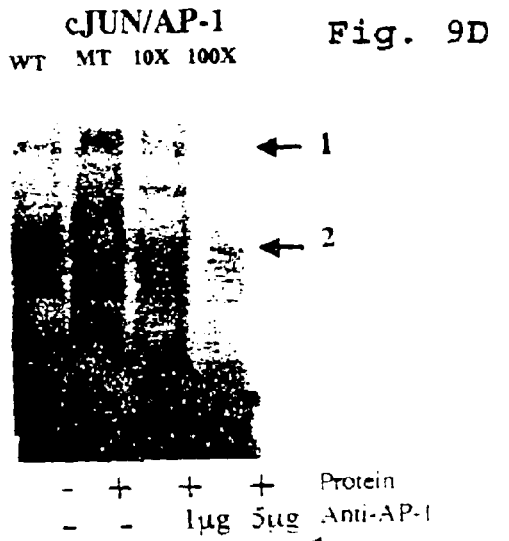
Figure 9E:
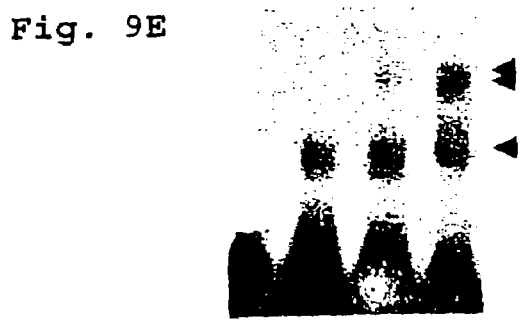
Figure 9F:
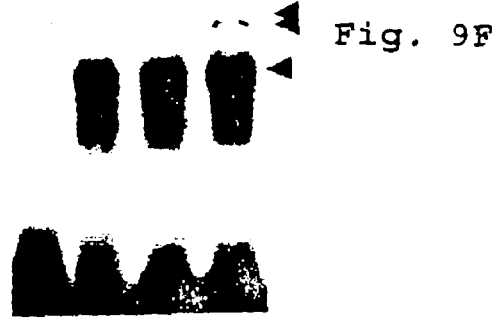

To demonstrate that C/EBP-β and cJUN/AP-1 proteins were responsible for DNA-protein complex formation, nuclear lysates from IFN-β+MEZ treated samples were incubated with $^{32}$[p]-labeled double stranded DNA sequences corresponding to this region of the mda-7 promoter and evaluated by EMSA. Reactions were performed using a wild-type, a mutant or a wild-type plus a 10- or 100-fold excess of canonical C/EBP-β (FIG. 9C left panel) or cJUN/AP-1 (FIG. 9D right panel) oligonucleotides. As shown in FIG. 9D, complex 1 results as a consequence of C/EBP-β binding to the mda-7 promoter and this interaction is reduced upon the addition of a 100-fold excess of canonical C/EBP binding double stranded synthetic oligonucleotides. The binding is not abolished when mutant oligonucleotides are used in place of the wild-type oligonucleotides. A reduction in complex 2, representing cJUN/AP-1 binding, is observed in the presence of an excess of sequence specific competitor oligonucleotides. To establish direct binding of C/EBP-β and cJUN/AP-1 to the NdeI-NheI region in the mda-7 promoter, supershift assays were performed using commercially available antibodies (SantaCruz). The results of the supershift assays, i.e., the presence of a slower migrating DNA-protein complex in the presence of antisera, document that both C/EBP-β and cJUN/AP-1 are capable of directly binding to the mda-7 promoter (FIGS. 9E and 9F). Increasing amounts of antiserum (1 mg and 5 mg) reacting with C/EBP-β or cJUN/AP-1, respectively, results in an increase in the amount of the retarded DNA-protein-antibody complex (FIGS. 9E and 9F, double arrowhead). Taken together, these findings indicate that both C/EBP-β and cJUN/AP-1 proteins specifically bind to the mda-7 promoter between the NdeI and NheI restriction enzyme recognition sites and enhance mda-7 gene expression by transcriptional activation.

Discussion

A proposed model of how human melanomas develop is the altered differentiation-modified gene expression hypothesis (5). This scheme suggests that melanoma cells display defects in normal programs of differentiation which correlate with a failure to express adequate levels of appropriate gene products required for maintaining normal cell growth and differentiated properties. In this model, specific regulatory genes are purported to be expressed in melanocytes and nevi, and perhaps even in primary radial and vertical growth phase melanomas, but expression is reduced or absent in metastatic melanoma. To define the repertoire of gene expression changes associated with induction of loss of growth potential and terminal differentiation in human melanoma cells we are using subtraction hybridization in combination with several standard and novel screening approaches (14, 16, 17). These include, random cDNA isolation and evaluation, reverse Northern screening of cDNA clones, high throughput microchip cDNA analyses of clones and the serial cDNA library array (SCLA) technology (14, 16, 17 and unpublished data). Mda-7 was identified by subtraction hybridization initially by random cDNA evaluation (5, 14) and subsequently by microchip cDNA analyses (17) and found to display elevated expression in melanocytes and nevi with a progressive reduction in expression as melanomas develop and progress (18). Terminal differentiation in human melanoma cells resulting from treatment with IFN-B+MEZ results in an elevation in the level of mda-7 mRNA and protein (18). Forced expression of mda-7 in human melanoma cells at physiological levels results in growth suppression and at high (non-physiological) levels culminates in programmed cell death (apoptosis) (18, 21). In these contexts, mda-7 may function as a negative regulator of melanoma growth and progression.

Previous studies have demonstrated that posttranscriptional regulation is an important determinant of mda-7 gene expression during terminal cell differentiation (22). The present studies provide documentation of a role for specific transcription factors and regions of the mda-7 promoter in regulating mda-7 gene expression in melanoma cells and during melanoma cell differentiation. Promoter deletion analysis identified regions of the mda-7 promoter responsible for immediate induction by the PKC activator, MEZ. These studies support an association between the transcription factor families cJun/AP-1 and C/EBP, and the expression and maintenance of mda-7 transcription during and subsequent to HO-1 terminal differentiation. Experimental evidence indicates that C/EBP-B/LAP mediates a terminal differentiation specific, transcriptional activation of the mda-7 promoter in HO-1 melanoma cells. Based on these cumulative findings, mda-7 expression during induction and maintenance of terminal differentiation in human melanoma cells is controlled by both transcriptional and posttranscriptional processes.

Transient transfection and cotransfection assays with the mda-7 promoter in proliferating and differentiating melanoma cells suggests that the AP-1 binding site is a key regulatory element kit necessary for rapid and full stimulation of gene transcription. This site also appears to be important in mediating mda-7 promoter activity in additional cell types, including HeLa. AP-1 consists of a family of transcription factors that bind specifically to the TPA-response element (TRE: TGAG/CTCA) and regulate transcription of genes containing the TRE by acting on their promoter (31, 34). Typically cJun/cFos heterodimers or cJun/cJun homodimers stimulate transcription by binding to the AP-1 binding domain in the promoter when cells are treated with PKC activators (31). Treatment of HO-1 cells with MEZ or IFN-B+MEZ results in a minimal induction of cJun message, although expression is quantitatively greater in combination treated cells (35). Additionally, it has been demonstrated that PKC-induced dephosphorylation of cJun could be one of the primary events leading to increased AP-1 activity in cells which contain low but significant basal levels of cJun protein (31). Western blotting data demonstrates that proliferating HO-1 cells contain significant basal levels of cJun protein and treatment with MEZ (or IFN-B+MEZ), but not IFN-B, may trigger a PKC dependent protein kinase cascade that results in the activation of DNA-binding activity of preexisting cJun by altering its phosphorylation state. In contrast to the low level induction of cJun, cFos and JunB messages are significantly induced by 24 h treatment with IFN-B, MEZ or a combination of IFN-B+MEZ (35). Taken together these observations suggest that increases in the amount of "active" cJun and newly synthesized cFos and Jun3 proteins during the first 24 h of IFN-B+MEZ treatment of HO-1 cells may contribute to the terminal differentiation phenotype. The mda-7 promoter is among the gene pool that is activated during melanoma terminal differentiation, and consistent with the kinetics of cJun and cFos expression, it is shown here that the AP-1 complex of transcription factors is required for sustained expression of the mda-7 message.

Preliminary studies in HeLa cells treated with MEZ or TPA provide further support for a role of AP-1 in activating the mda-7 promoter. Up-regulation of mda-7 promoter activity in HeLa cells by PKC activation is antagonized by the addition of the glucocorticoid, dexamethasone (unpublished data). The ability of the glucocorticoid receptor to repress TPA induction involves an interaction with the DNA binding domain of cJun (36) and is specific for AP-1 since other transcription factors involved in gene regulation by TPA, e.g., SRF, are not affected (37). Ectopic expression of the cJun plasmid can significantly activate the mda-7 promoter by itself in HeLa cells, and cJun in conjunction with JNK can markedly stimulate the mda-7 promoter (unpublished data). We presently demonstrate that AP-1 activity is necessary for induction of human melanoma terminal differentiation. Similar changes in expression of AP-1 transcription factors are evident in murine melanoma cells when treated with differentiation inducers such as, retinoic acid and cAMP (review, 34). Changes in cJun and JunB levels occur during monocytic differentiation of HL 60 promyelocytic leukemia cells and U937 histiocytic lymphoma cells following treatment with TPA and Vitamin D3 (38). Taken together these observations implicate cJun/AP-1 transcription factor complexes as a key regulator of mda-7 gene expression during proliferation and terminal differentiation.

While the AP-1 transcription factor is necessary for the rapid and sustained induction of the mda-7 promoter, during proliferation and differentiation, our data also suggests that a second transcription factor, C/EBP-B/LAP is responsible for terminal differentiation specific maintenance of mda-7 gene expression. It appears that C/EBP-B/LAP binding sites at a distance from the TATA element are responsible for mda-7 expression in terminally differentiated human melanoma cells. Another line of evidence supporting the involvement of the C/EBP gene family in melanoma terminal differentiation is apparent from increased levels of C/EBP-B/LAP protein in HO-1 cells as early as 24 h after treatment with IFN-β+MEZ when compared to cells treated with IFN-β, MEZ or TPA. The transcription factor C/EBP is a heat-stable, sequence-specific DNA-binding protein first purified from rat liver nuclei (39). C/EBP regulates gene expression in a variety of tissues including liver, adipose, lung and intestine (40). This transcription factor appears to function exclusively in differentiated and growth-arrested cells (40). Recent studies suggest that the cellular levels of C/EBP-B/LAP are regulated by translation and secondly as a result of C/EBP-a dependent proteolytic cleavage of C/EBP-B/LAP into LAP (35 kDa; transcription activator) and LIP (21 and 14 kDa; transcription inhibitor) (41). It is the ratio of LIP/LAP that is important in C/EBP-mediated gene expression. In the case of terminally differentiated HO-1 melanoma cells, we were unable to detect any LIP protein. The present studies provide evidence that the C/EBP gene family members, C/EBP-B/LAP in particular, play a major role during melanoma terminal differentiation. C/EBP-a and -B can both directly induce the mda-7 promoter as shown by ectopic expression analyses. Another line of evidence pointing to the importance of C/EBP in mda-7 promoter activation is the finding that promoter activity is induced when cells are treated with IL-6 (unpublished data). IL-6 is a potent inducer of NF-IL6, a DNA binding protein that is highly homologous to the C/EBP-B (LAP) gene family members (42). NF-IL6 transcription factor is up-regulated during macrophage differentiation and is responsible for the regulation of genes expressed in mature macrophages, indicating that NF-IL6 is an important transcription factor for macrophage activation and/or differentiation (43). Progressive deletions of the mda-7 promoter from the 5'-end lead to increased and sustained levels of promoter induction with IL-6. Based on these observations, it is apparent that the various recombinant C/EBP gene family members such as C/EBP-a, C/EBP-B and NF-IL6 can activate the C/EBP binding sites present in the mda-7 promoter. Future studies will address the specific roles of C/EBP and its extended gene family in mda-7 gene regulation and more importantly in terminal differentiation of human melanoma cells. These investigations should provide relevant insights into the regulation of an important, growth, differentiation and apoptosis associated gene, mda-7.

REFERENCES FOR EXAMPLE 1

Aharon T and Schneider R J. (1993). *Mol. Cell. Biol.,* 13, 1971–1980.
Belasco J G and Higgins C F. (1988). *Gene,* 72, 15–23.
Elder P K, Schmidt L J, Ono T and Getz M J. (1984). *Proc. Natl. Acad. Sci. USA,* 81, 7476–7480.
Fisher P B, Prignoli D R, Hermo H Jr, Weinstein I B and Pestka S. (1985). *Interferon Res.,* 5, 11–22.
Fontes A M, Ito J and Jacobs-Lorena M. (1999). *Curr. Top. Dev. Biol.,* 44, 171–202.
Goeddel D V, Leung D W, Dull T J, Gross M, Lawn R M, McCandliss R, Seeburg P H, Ullrich A, Yelverton E and Gray P W. (1981). *Nature,* 5, 20–26.
Huang F, Adelman J, Jiang H, Goldstein N I and Fisher P B. (1999a). *Oncogene,* 18, 3546–3552.
Huang F, Adelman J, Jiang H, Goldstein N I and Fisher P B. (1999b). *Gene,* 236, 125–131.
Huberman E and Callaham M F. (1979). *Proc. Natl. Acad. Sci. USA,* 76, 1293–1297.
Ishikawa M, and Kerbel R S. (1989). *Int. J. Cancer,* 43, 134–139.
Jiang H, Waxman S and Fisher, P B. (1993). *Mol Cell. Different.,* 1, 197–214.
Jiang H and Fisher P B. (1993). *Mol. Cell. Different.,* 1, 285–299.
Jiang H, Lin J and Fisher P B. (1994). *Mol. Cell. Different.,* 2, 221–239.
Jiang H, Lin J J, Su Z-z, Goldstein N I and Fisher P B. (1995a). *Oncogene,* 11, 2477–2486.
Jiang H, Lin J, Su Z-z, Kerbel R S, Herlyn M, Weissman R B, Welch D and Fisher P B. (1995b) *Oncogene,* 10, 1855–1864.
Jiang H, Lin J J, Su Z-z, Goldstein N I and Fisher P B. (1996). *Proc. Natl. Acad. Sci. USA,* 93, 9160–9165.
Kang D-c, LaFrance R, Su Z-z and Fisher P B. (1998a). *Proc. Natl. Acad. Sci. USA,* 95, 13788–13793.
Kang D-c, Motwani M and Fisher P B. (1998b). *Int. J. Oncol.* 13, 1117–1126.
Krowczynska A, Yenofsky R and Brawerman G. (1985). *J. Mol. Biol.,* 181, 231–239.
Linial M, Gunderson N and Groudine M. (1985). *Science,* 230, 1126–1132.
Madireddi M T, Davis M C and Allis C D. (1994). *Dev. Biol.,* 165: 418–431.
Miller A D, Curran T and Verma I M. (1984). *Cell,* 36, 51–60.
Myer V E, Fan X C and Steitz J A. (1997). *EMBO J.,* 16, 2130–2139.
Nedwin G E, Svedersky L P, Bringman T S, Palladino M A Jr and Goeddel D V. (1985). *J. Immunol.,* 135, 2492–2497.
Patterson A and Harris A L. (1999). *Drugs Aging,* 14, 75–90.
Raj N B and Pitha P-M. (1981). *Proc. Natl. Acad. Sci. USA,* 78, 7426–7430.
Rajagopalan L E and Malter J S. (1997). *Prog. Nucleic Acid Res. Mol. Biol.,* 56, 257–286.
Ross J. (1996). *Trends Genet.,* 12, 171–175.
Sachs L. (1980). *Proc. Natl. Acad. Sci. USA,* 77, 6152–6156.
Scott R E and Maercklein P B. (1985). *Proc. Natl. Acad. Sci. USA,* 82, 2995–2999.
Scott R E. (1997). *Pharmacol. Ther.,* 73, 51–65.
Shaw G and Kamen R. (1986). *Cell* 46: 659–667.
Shyu A B, Belasco J G and Greenberg M E. (1991). *Genes & Dev.,* 2, 221–231.
Spicher A, Guicherit O M, Duret L, Aslanian A, Sanjines E M, Denko N C, Giaccia A J and Blau H M. (1998). *Mol. Cell. Biol.,* 12, 7371–7382.
Su Z-z, Madireddi M T, Lin J J, Young C S H, Kitada S, Reed J C, L I Goldstein N I and Fisher P B. (1998). *Proc. Natl. Acad. Sci. USA,* 95, 14400–14405.
Tamayo P, Slonim D, Mesirov J, Zhu Q, Kitareewan S, Dimitrovsky E, Lander E S and Golub T R. (1999). *Proc. Natl. Acad. Sci. USA,* 96, 2907–2912.
van Straaten F, Muller R, Curran T, van Beveren C and Verma I M. (1983). *Proc. Natl. Acad. Sci. USA,* 80, 3183–3187.
Wada R K, Pai D S, Huang J, Yamashiro J M and Sidell N. (1997). *Cancer Lett.,* 121, 181–188.
Waxman S, Rossi G B and Takaku F. (1991). *The Status of Differentiation Therapy of Cancer,* Waxman S, Rossi G B and Takaku F (eds). Serono Symposia Pubs., Raven Press, New York.
Waxman S (1995). *Differentiation Therapy.* Waxman S (ed). Serono Symposium Publications, Rome, Italy.
Wong G G, Witek J S, Temple P A, Wilkens K M, Leary A C, Luxenberg D P, Jones S S, Brown E L, Kay R M, Orr E C, Shoemaker C, Golde D W, Kaufman R J, Hewick R M, Wang E A and Clark S. C. (1985). *Science,* 228, 810–815.

REFERENCES FOR EXAMPLE 2

1. Herlyn, M. (1990) *Cancer Metastasis Rev* 9, 101–112.
2. Lu, C., and Kerbel, R. S. (1994) *Curr. Opin. Oncol.* 6, 212–220.
3. Welch, D. R., and Goldberg, S. F. (1997) *Pathobiology* 65, 311–330.
4. Meier, F., Satyamoorthy, K., Nesbit, M., Hsu, M. Y., Schittek, B., Garbe, C., and Herlyn, M. (1998) *Front. Bioscience* 3, D1005–1010.
5. Jiang, H., Lin, J., and Fisher, P. B. (1994) *Mol. Cell. Different.* 2, 221–239.
6. Clark, W. (1991) *Br. J. Cancer* 64, 631–644.
7. Armstrong, B. K., and Kricker, A. (1994) *Cancer Surv.* 19/20, 219–240.
8. Sachs, L. (1978) *Nature* 274, 535–539.
9. Fisher, P. B., Prignoli, D. R., Hermo, H., Jr., Weinstein, I. B., and Pestka, S. (1985) *J. Interferon Res.* 5, 11–22.
10. Waxman, S., Rossi, G. B., and Takaku, F., Eds. (1991) The Status of Differentiation Therapy, Vol. 2, Raven Press, New York.
11. Waxman, S., Ed. (1995) Differentiation Therapy. Serono Symposium Publications, Rome, Italy.
12. Jiang, H., Su, Z.-z., Boyd, J., and Fisher, P. B. (1993) *Mol. Cell. Different.* 1, 41–66.
13. Jiang, H., Lin, J., Young, S.-m., Goldstein, N. I., Waxman, S., Davila V., Chellappan, S. P., and Fisher, P. B. (1995) *Oncogene* 11, 1179–1189.
14. Jiang, H., and Fisher, P. B. (1993) *Mol. Cell. Different.* 1, 285–299.
15. Jiang, H., Lin, J., Su, Z.-z., Kerbel, R. S., Herlyn, M., Weissman, R. B., Welch, D., and Fisher, P. B. (1995) *Oncogene* 10, 1855–1864.
16. Huang, P., Adelman, J., Jiang, H., Goldstein, N. I., and Fisher, P. B. (1999) *Gene* 236, 125–131.
17. Huang, F., Adelman, J., Jiang, H., Goldstein, N. I., and Fisher, P. B. (1999) *Oncogene* 18, 3546–3552.
18. Jiang, H., Lin, J. J., Su, Z.-z., Goldstein, N. I., and Fisher, P. B. (1995) *Oncogene* 11, 2477–2486.
19. Jiang, H., Su, Z.-z., Lin, J. J., Goldstein, N. I., Young, C. S. H., and Fisher, P. B. (1996) *Proc. Natl. Acad. Sci. USA* 93, 9160–9165.

20. Su, Z.-z., Madireddi, M. T., Lin, J. J., Young, C. S. H., Kitada, S., Reed, J. C., Goldstein, N. I., and Fisher, P. B. (1998) *Proc. Natl. Acad. Sci. USA* 95, 14400–14405.
21. Madireddi, M. T., Su, Z.-z., Young, C. S. H., Goldstein, N. I., and Fisher, P. B. (2000) Cancer Gene Therapy: Past Achievements and. Future Challenges, N. Habib, Ed., Plenum Publishing Company, New York, in press.
22. Madireddi, M. T., Dent, P., and Fisher, P. B. (2000) *Oncogene, in press*.
23. Madireddi, M. T., Davis, M. C., and Allis, C. D. (1994) Dev. Biol. 165, 418–431.
24. Su, Z.-z., Yemul, A., Estabrook, A., Zimmer, S. G., Friedman, R. M., and Fisher, P. B. (1995) *Intl. J. Oncology* 7, 1279–1284.
25. Dignam, J. M., Lebovitz, R. M., and Roeder, R. G. (1983) *Nucl. Acids. Res.* 11, 1475–1489.
26. Su, Z.-z., Shen, R., O'Brian, C. A., and Fisher, P. B. (1994) *Oncogene* 9, 1123–1132.
27. Kerr, L. D. (1995) *Methods Enzymol.* 254, 619–632.
28. Gant, T. M., and Wilson, K. L. (1997) *Annu. Rev. Cell Dev. Biol.* 13, 669–695.
29. MacDougald, O. A., and Lane, M. D. (1995) *Annu. Rev. Biochem.* 64, 345–373.
30. Umek, R. M., Friedman, A. D., and McKnight, S. L. (1991) *Science* 251, 288–292.
31. Angel, P., and Karin, M. (1991) *Biochem. Biophys. Acta* 1072, 129–157.
32. Auer, K. L., Contessa, J., Brenz-Verca, S., Pirola, L., Rusconi, S., Cooper, G., Abo, A., Wymann, M. P., Davis, R. J., Birrer, M., and Dent, P. (1998) *Mol. Biol. Cell* 9, 561–573.
33. Dong, Z., Xu, R. H, Kim, J., Zhan, S. N., Ma, W. Y., Colburn, N. H., and Kung, H. (1996) *J. Biol. Chem.* 26, 9942–9946.
34. Kang, D.-c., Motwani, M., and Fisher, P. B. (1998) *Int. J. Oncol.* 13, 1117–1126.
35. Jiang, H., Waxman, S., and Fisher, P. B. (1993) *Mol. Cell. Different.* 1, 197–214.
36. Yang-Yen, H. F., Chambard, J. C., Sun, Y. L., Smeal, T., Schmidt, T. J., Drouin, J., and Karin, M. (1990) *Cell* 62, 1205–1215.
37. Jonat, C., Rahmsdorf, H. J., Park, K. K., Cato, A. C., Gebel, S., Ponta, H., and Herrlich, P. (1990) *Cell* 62, 1189–1204.
38. Sherman, M. L., Datta, R., Hallahan, D. E., Weichselbaum, R. R., and Kufe, D. W. (1990) *Proc. Natl. Acad. Sci. USA* 87, 5663–5666.
39. Johnson, P. F. (1993) *Mol. Cell Biol.* 13. 6919–6930.
40. Birkenmeier, E. H., Gwynn, B., Howard, S., Jerry, J., Gordon, J. I., Landschulz, W. H., and McKnight, S. L. (1989) *Genes & Dev.* 3, 1146–1156.
41. Welm A. L, Timchenko, N. A, and Darlington, G. J. (1999) *Mol. Cell Biol.* 19, 1695–1704.
42. Akira, S., Isshiki, R., Sugita, T., Tanabe, O., and Kinoshita, S. (1990) *EMBO J.* 9, 1897–1906.
43. Natsuka, S., Akira, S., Nishio, Y., Hashimoto, S., Sugita, T., Isshiki, H., and Kishimoto, T. (1992) *Blood* 79, 460–466.

What is claimed is:

1. An isolated nucleic acid transcription promoter molecule having transcriptional promoter activity and at least 95 percent sequence identity to the nucleic acid sequence set forth in SEQ ID NO: 1 from the thymidine at position 1 to the cytosine at position 2240.

2. An isolated nucleic acid transcription promoter molecule which comprises the nucleotide sequence shown in SEQ ID NO: 1 from the thymidine at position 1 to the cytosine at position 2240.

3. A recombinant expression construct effective in directing the transcription of a selected coding sequence which comprises:
   (a) a promoter molecule according to claim 1 or claim 2; and
   (b) a coding sequence operably linked downstream to the promoter molecule, wherein the promoter is heterologous to the coding sequence.

4. The recombinant expression construct of claim 3, wherein the promoter molecule is a human Mda-7 promoter.

5. The recombinant expression construct of claim 3, wherein the promoter comprises the nucleotide sequence shown in SEQ ID NO: 1 from the thymidine (T) at position 1 to the cytosine (C) at position 2240.

6. The recombinant expression construct of claim 3, wherein the coding sequence encodes a tumor suppressor polypeptide.

7. The recombinant expression construct of claim 6, wherein the tumor suppressor polypeptide is selected from the group consisting of p21 retinoblastoma protein and p53.

8. An isolated host cell comprising the recombinant expression construct of claim 3.

9. The isolated host cell of claim 8, wherein the host cell is stably transformed with the recombinant expression construct of claim 3.

10. A method for expressing foreign DNA in an isolated host cell comprising introducing into the host cell a gene transfer vector comprising an isolated nucleic acid transcription promoter molecule having transcriptional promoter activity and at least 95 percent sequence identity to the nucleic acid sequence set forth in SEQ ID NO: 1 from the thymidine at position 1 to the cytosine at position 2240, wherein the promoter is operably linked to a foreign DNA molecule such that the foreign DNA molecule is downstream of the promoter, so that the foreign DNA is transcribed and expressed in the host cell.

11. The method of claim 10, wherein the nucleic acid sequence of the promoter is identical to the sequence from position 1 to position 2240 of SEQ ID NO: 1.

12. The method of claim 10, wherein the nucleic acid sequence of the promoter is as set forth in SEQ ID NO:1.

13. The method of claim 10, wherein the gene transfer vector encodes and expresses a reporter molecule.

14. The method of claim 13, wherein the reporter molecule is selected from the group consisting of beta-galactosidase, luciferase and chloramphenicol acetyltransferase.

15. The method of claim 10, wherein the introducing is carried out by a means selected from the group consisting of adenovirus infection, liposome-mediated gene transfer, and microinjection.

* * * * *